US011156617B2

(12) United States Patent
Sahin et al.

(10) Patent No.: US 11,156,617 B2
(45) Date of Patent: Oct. 26, 2021

(54) PREDICTING T CELL EPITOPES USEFUL FOR VACCINATION

(71) Applicants: BioNTech RNA Pharmaceuticals GmbH, Mainz (DE); TRON-Translationale Onkologie an der Universitätsmedizin der Johannes Gutenberg-Universität Mainz gGmbH, Mainz (DE)

(72) Inventors: Ugur Sahin, Mainz (DE); Martin Löwer, Mainz (DE); Arbel D. Tadmor, Bodenheim (DE); Sebastian Boegel, Obermoschel (DE); Barbara Schrörs, Mainz (DE); Mathias Vormehr, Mainz (DE); Sebastian Kreiter, Mainz (DE)

(73) Assignees: BioNTech RNA Pharmaceuticals GbmH, Mainz (DE); TRON-Translationale Onkologie an der Universitätsmedzin der Johannes Gutenberg-Universität Mainz gGmbH, Mainz (DE)

( * ) Notice: Subject to any disclaimer, the term of this patent is extended or adjusted under 35 U.S.C. 154(b) by 346 days.

(21) Appl. No.: 15/550,286

(22) PCT Filed: Feb. 9, 2016

(86) PCT No.: PCT/EP2016/052684
§ 371 (c)(1),
(2) Date: Aug. 10, 2017

(87) PCT Pub. No.: WO2016/128376
PCT Pub. Date: Aug. 18, 2016

(65) Prior Publication Data
US 2019/0250166 A1    Aug. 15, 2019

(30) Foreign Application Priority Data
Feb. 12, 2015   (WO) ................. PCT/EP2015/053021

(51) Int. Cl.
*G01N 33/68*   (2006.01)
*G01N 33/50*   (2006.01)
*A61K 39/00*   (2006.01)

(52) U.S. Cl.
CPC ...... *G01N 33/6845* (2013.01); *A61K 39/0011* (2013.01); *G01N 33/505* (2013.01); *G01N 2333/70539* (2013.01); *G01N 2500/04* (2013.01)

(58) Field of Classification Search
None
See application file for complete search history.

(56) References Cited

U.S. PATENT DOCUMENTS

| 4,897,355 A | 1/1990 | Eppstein et al. |
|---|---|---|
| 5,264,618 A | 11/1993 | Felgner et al. |
| 5,703,055 A | 12/1997 | Felgner et al. |
| 6,251,399 B1 | 6/2001 | Diamond et al. |
| 6,472,176 B2 | 10/2002 | Kovesdi et al. |
| 6,500,641 B1 | 12/2002 | Chen et al. |
| 6,586,410 B1 | 7/2003 | Wheeler et al. |
| 7,303,881 B2 | 12/2007 | Huang et al. |
| 7,462,354 B2 | 12/2008 | Sette et al. |
| 7,790,696 B2 | 9/2010 | Gregoriadis |
| 8,140,270 B2 | 3/2012 | Kingsmore et al. |
| 8,217,016 B2 | 7/2012 | Hoerr et al. |
| 8,349,558 B2 | 1/2013 | Fatho et al. |
| 8,703,142 B2 | 4/2014 | Diamond et al. |
| 8,853,283 B2 | 10/2014 | Platscher et al. |
| 8,877,206 B2 | 11/2014 | Chen et al. |
| 9,115,402 B2 | 8/2015 | Hacohen et al. |
| 10,055,540 B2 | 8/2018 | Yelensky et al. |
| 10,738,355 B2 | 8/2020 | Sahin et al. |
| 2007/0025968 A1 | 2/2007 | Van Der Burg et al. |
| 2009/0055944 A1 | 2/2009 | Korman et al. |
| 2009/0217401 A1 | 8/2009 | Korman et al. |
| 2009/0298056 A1 | 12/2009 | Mautner et al. |
| 2012/0237975 A1 | 9/2012 | Schrum et al. |

(Continued)

FOREIGN PATENT DOCUMENTS

| EP | 0839912 A1 | 5/1998 |
|---|---|---|
| EP | 1242108 A1 | 9/2002 |

(Continued)

OTHER PUBLICATIONS

Sallman et al. Hematology/Oncology and Stem Cell Therapy, vol. 9, Issue 3, Sep. 2016, pp. 89-95.*
Agrawal et al., Trend in Biotechnology, 14(10): 376-387, 1996.
Mayer et al., Anticancer Research 25:3917-3924 (2005).
Bei et al.J Immunother. May 1998;21(3):159-69.
Boczkowski et al. (1996). "Dendritic cells pulsed with RNA are potent antigen-presenting cells in vitro and in vivo," J. Exp. Med. 184: 465-472.
Bowerman, NA. "Engineering the binding properties of the T cell receptor: peptide: MHC ternary complex that governs T cell activity." Mol. Immun. 46: 3000-3008, 2009.
Brickner et al. J. Exp. Med 193(2) 195-205 (2001).
Del Val et al., Cell, vol. 66, Issue 6, Sep. 20, 1991, pp. 1145-1153.

(Continued)

*Primary Examiner* — Michael L Borin
(74) *Attorney, Agent, or Firm* — Choate, Hall & Stewart LLP; Brenda Herschbach Jarrell; Janet M. Tse

(57) ABSTRACT

The present invention relates to methods for predicting T cell epitopes useful for vaccination. In particular, the present invention relates to methods for predicting whether modifications in peptides or polypeptides such as tumor-associated neoantigens are immunogenic and, in particular, useful for vaccination, or for predicting which of such modifications are most immunogenic and, in particular, most useful for vaccination. The methods of the invention may be used, in particular, for the provision of vaccines which are specific for a patient's tumor and thus, in the context of personalized cancer vaccines.

21 Claims, 19 Drawing Sheets

Figure 1:
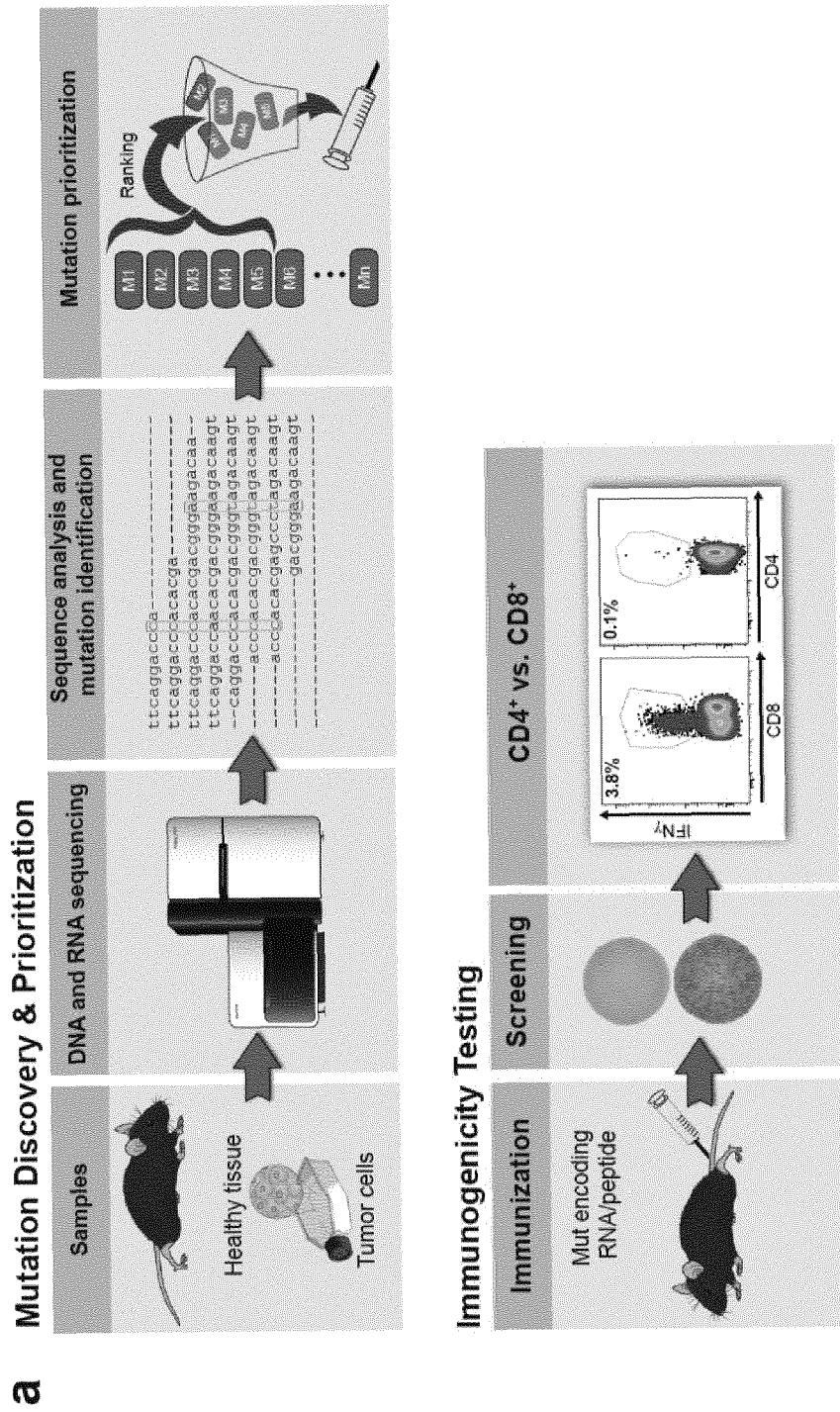
Figure 1:
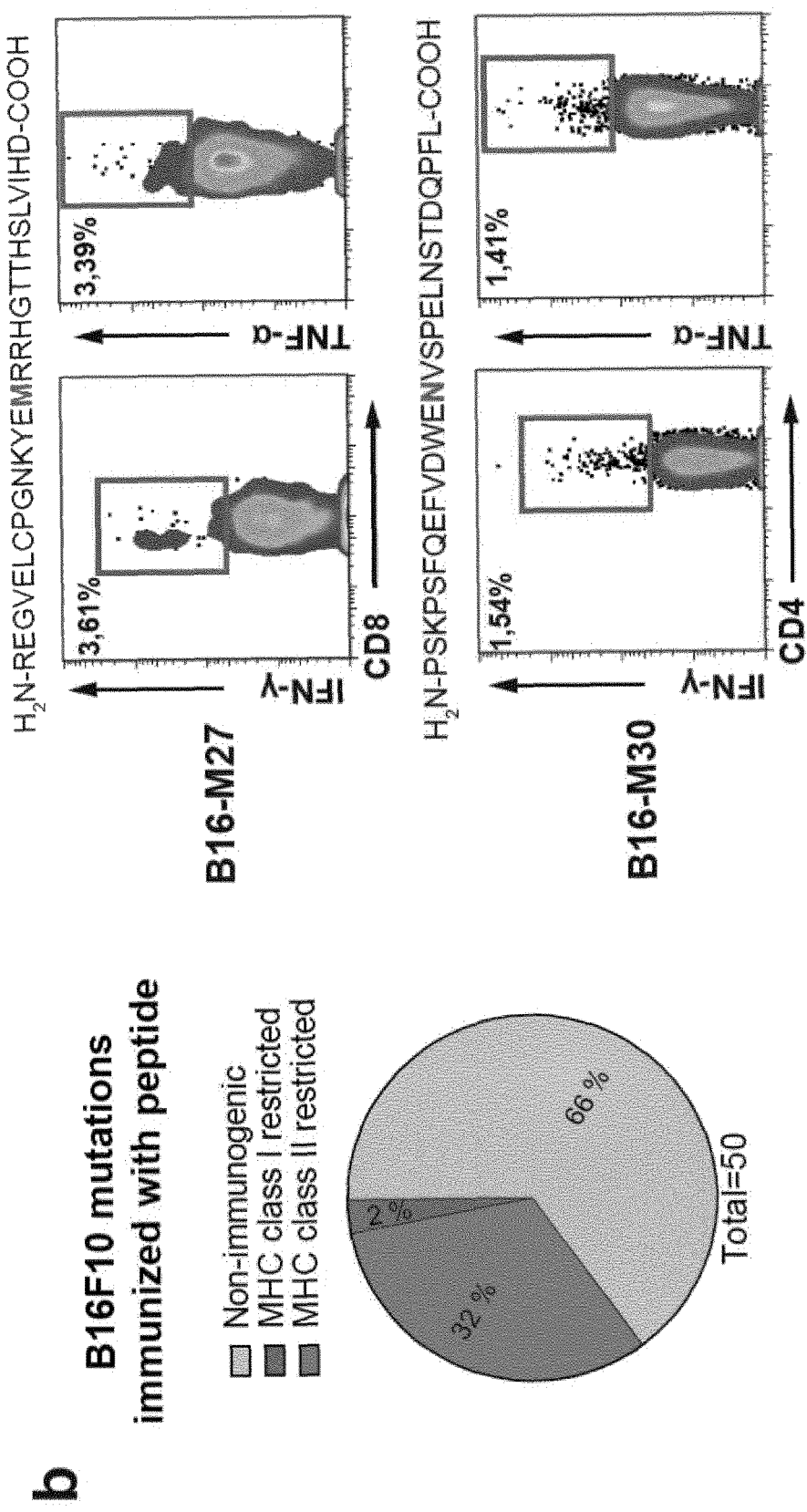
Figure 1:
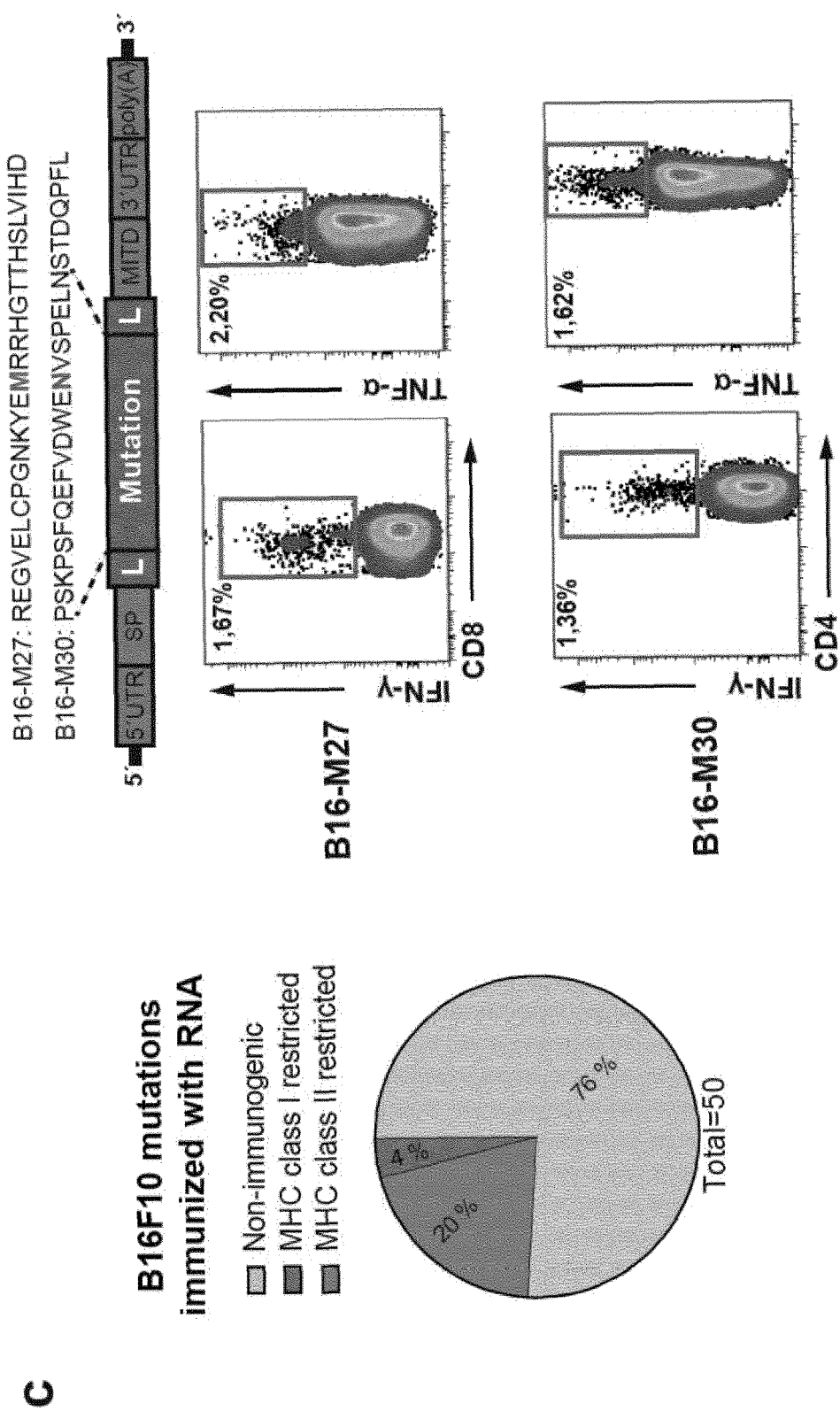
Figure 1:
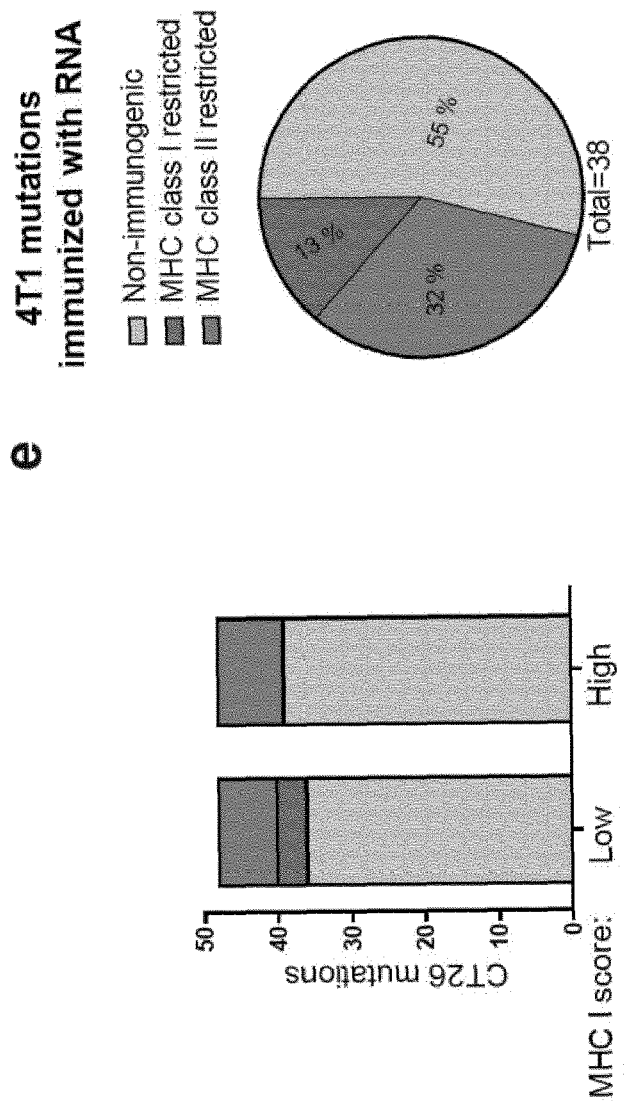
Figure 1:
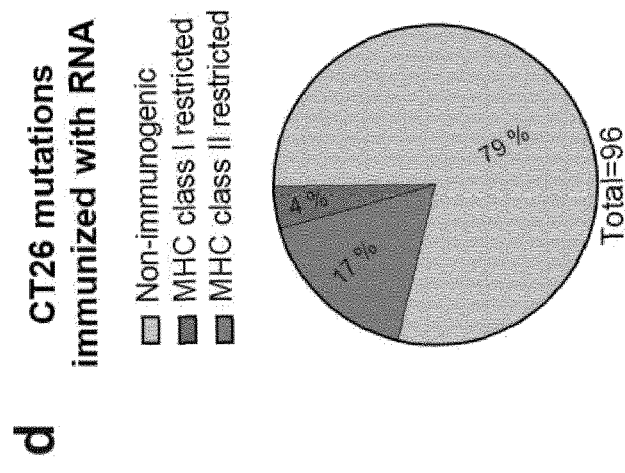

Specification includes a Sequence Listing.

(56) References Cited

U.S. PATENT DOCUMENTS

| | | | |
|---|---|---|---|
| 2013/0115272 A1 | 5/2013 | de Fougerolles et al. | |
| 2013/0123481 A1 | 5/2013 | de Fougerolles et al. | |
| 2013/0156849 A1 | 6/2013 | de Fougerolles et al. | |
| 2013/0203115 A1 | 8/2013 | Schrum et al. | |
| 2013/0237593 A1 | 9/2013 | de Fougerolles et al. | |
| 2013/0237594 A1 | 9/2013 | de Fougerolles et al. | |
| 2013/0244278 A1 | 9/2013 | de Fougerolles et al. | |
| 2013/0244279 A1 | 9/2013 | de Fougerolles et al. | |
| 2013/0245106 A1 | 9/2013 | de Fougerolles et al. | |
| 2013/0245107 A1 | 9/2013 | de Fougerolles et al. | |
| 2013/0255281 A1 | 10/2013 | Bray | |
| 2013/0266640 A1 | 10/2013 | de Fougerolles et al. | |
| 2014/0010861 A1 | 1/2014 | Bancel et al. | |
| 2014/0147454 A1 | 5/2014 | Chakraborty et al. | |
| 2014/0178438 A1 | 6/2014 | Sahin et al. | |
| 2015/0017211 A1 | 1/2015 | de Fougerolles et al. | |
| 2015/0030576 A1 | 1/2015 | Bancel | |
| 2015/0167017 A1 | 6/2015 | Roy et al. | |
| 2016/0125129 A1* | 5/2016 | Sahin | A61K 39/0011 424/277.1 |
| 2017/0016075 A1* | 1/2017 | Velculescu | G01N 33/6878 |

FOREIGN PATENT DOCUMENTS

| | | |
|---|---|---|
| EP | 2569633 A2 | 3/2013 |
| JP | 2006-518982 A | 8/2006 |
| JP | 2011-135874 A | 7/2011 |
| JP | 2014-523406 A | 9/2014 |
| WO | 1994023031 A1 | 10/1994 |
| WO | 1998014464 A1 | 4/1998 |
| WO | 1999024566 A1 | 5/1999 |
| WO | 1999052503 A2 | 10/1999 |
| WO | 2000/20029 A1 | 4/2000 |
| WO | 2000067761 A1 | 11/2000 |
| WO | 2001047959 A2 | 7/2001 |
| WO | WO-01/55393 A2 | 8/2001 |
| WO | 2001093902 A2 | 12/2001 |
| WO | 2002048377 A2 | 6/2002 |
| WO | 2002083714 A2 | 10/2002 |
| WO | 02/098443 A2 | 12/2002 |
| WO | 2003051401 A2 | 6/2003 |
| WO | 2003068257 A1 | 8/2003 |
| WO | 2003106692 A2 | 12/2003 |
| WO | 2004004743 A1 | 1/2004 |
| WO | WO-2004/031230 A2 | 4/2004 |
| WO | 2005030250 A2 | 4/2005 |
| WO | 2005039533 A1 | 5/2005 |
| WO | 2005040816 A1 | 5/2005 |
| WO | 2005110338 A2 | 11/2005 |
| WO | 2006121168 A1 | 11/2006 |
| WO | 2007024708 A2 | 3/2007 |
| WO | 2007025760 A2 | 3/2007 |
| WO | 2007031222 A2 | 3/2007 |
| WO | 2007101227 A2 | 9/2007 |
| WO | 2008080468 A1 | 7/2008 |
| WO | 2008083174 A2 | 7/2008 |
| WO | 2008085562 A2 | 7/2008 |
| WO | 2008116078 A2 | 9/2008 |
| WO | 2008156712 A1 | 12/2008 |
| WO | 2009053041 A2 | 4/2009 |
| WO | 2009118296 A2 | 10/2009 |
| WO | 2009129227 A1 | 10/2009 |
| WO | 2010066418 A1 | 6/2010 |
| WO | 2011012316 A1 | 2/2011 |
| WO | 2011143656 A2 | 11/2011 |
| WO | 2012045075 A1 | 4/2012 |
| WO | 2012045082 A2 | 4/2012 |
| WO | 2012135805 A2 | 10/2012 |
| WO | 2012159729 A1 | 11/2012 |
| WO | 2012159754 A2 | 11/2012 |
| WO | WO-2012/159643 A1 | 11/2012 |
| WO | 2013040142 A2 | 3/2013 |
| WO | 2013052523 A1 | 4/2013 |
| WO | 2013090648 A1 | 6/2013 |
| WO | 2013124701 A2 | 8/2013 |
| WO | 2013151663 A1 | 10/2013 |
| WO | 2013151664 A1 | 10/2013 |
| WO | 2013151665 A2 | 10/2013 |
| WO | 2013151672 A2 | 10/2013 |
| WO | 2014012051 A1 | 1/2014 |
| WO | 2014071219 A1 | 5/2014 |
| WO | 2014093924 A1 | 6/2014 |
| WO | 2014144039 A1 | 9/2014 |
| WO | 2014144711 A1 | 9/2014 |
| WO | 2014144767 A1 | 9/2014 |
| WO | 2014152027 A1 | 9/2014 |
| WO | 2014152030 A1 | 9/2014 |
| WO | 2014152031 A1 | 9/2014 |
| WO | 2014152211 A1 | 9/2014 |
| WO | 2014159813 A1 | 10/2014 |
| WO | 2014160243 A1 | 10/2014 |
| WO | 2014164253 A1 | 10/2014 |
| WO | 2014168874 A2 | 10/2014 |
| WO | 2014180569 A1 | 11/2014 |
| WO | 2015014375 A1 | 2/2015 |
| WO | 2015034925 A1 | 3/2015 |
| WO | 2015034928 A1 | 3/2015 |
| WO | 2015038892 A1 | 3/2015 |
| WO | 2015043613 A1 | 4/2015 |
| WO | 2015051169 A2 | 4/2015 |
| WO | 2015051173 A2 | 4/2015 |
| WO | 2015058780 A1 | 4/2015 |
| WO | 2015085318 A2 | 6/2015 |
| WO | 2015089511 A2 | 6/2015 |
| WO | 2015117620 A1 | 8/2015 |
| WO | 2015164674 A1 | 10/2015 |
| WO | 2015172843 A1 | 11/2015 |
| WO | 2016062323 A1 | 4/2016 |
| WO | 2016/091391 A1 | 6/2016 |
| WO | 2016107877 A1 | 7/2016 |
| WO | WO-2016/128060 A1 | 8/2016 |
| WO | 2016155809 A1 | 10/2016 |
| WO | WO-2017/106638 A1 | 6/2017 |
| WO | WO-2018/195357 A1 | 10/2018 |
| WO | WO-2018/227030 A1 | 12/2018 |
| WO | WO-2019/050994 A1 | 3/2019 |
| WO | WO-2019/075112 A1 | 4/2019 |
| WO | WO-2019/104203 A1 | 5/2019 |
| WO | WO-2019/168984 A1 | 9/2019 |

OTHER PUBLICATIONS

Conry et al. (1994). "Immune response to a carcinoembryonic antigen polynucleotide vaccine," Cancer Res. 54: 1164-1168.

Conry et al. (1995). "Characterization of a messenger RNA polynucleotide vaccine vector," Cancer Res. 55: 1397-1400.

Coulie et al. (1995). "A mutated intron sequence codes for an antigenic peptide recognized by cytolytic T lymphocytes on a human melanoma," Proc. Natl. Acad. Sci. USA 92: 7976-7980.

Dengjel, J. et al. "Glycan side chains on naturally presented MHC class II ligands" J. Mass Spectrom, 2005.

Ding et al. "Genome remodeling in a basal-like breast cancer metastatis and xenograft." Nature, 464: 999-1005, 2010.

Dolgin, Nature 522:26.

Fritsch, E. F. et al. "HLA-Binding Properties of Tumor Neoepitopes in Humans" Cancer Immunology Research, 2: 522-529, 2014.

Gnirke, A. "Solution hybrid selection with ultra-long oligonucleotides for massively parallel targeted sequencing" Nat. Biotechnol, 2009.

Goya R. et al. "SNVMix: predicting single nucleotide variants from next-generation sequencing of tumors, Bioinformatics" Bioinformatics, 26: 730-736, 2010.

Gryaznov et al., Biochim. Biophys. Acta, 1489: 131-140, 1999.

Guyre et al., Cancer Immunother (1997) 45:146-148.

Hacohen Decl. dated Feb. 16, 2014 filed in U.S. Appl. No. 13/108,610, 10 pages.

Hoerr et al. (2000). "In vivo application of RNA leads to induction of specific cytotoxic T lymphocytes and antibodies," Eur. J. Immunol. 30: 1-7.

(56) References Cited

OTHER PUBLICATIONS

Johanning et al. Nucleic Acids Res. May 11, 1995; 23(9): 1495-1501.
Kenter, G. G. et al. "Phase I Immunotherapeutic Trial with Long Peptides Spanning the E6 and E7 sequences of High-risk human papillomavirus 16 in End-stage cervical cancer patients shows low toxicity and robust immunogenicity." Clinical Cancer Research, 14: 169-177, 2008.
Keogh, E. et al. "Identification of New Epitopes from Four Different Tumor-Associated Antigens: Recognition of Naturally Processed Epitopes Correlates with HLA-A*0201-Binding Affinity" J. Immunol. 167: 787-796, 2001.
Lemmel, Claudia et al., "Differential quantitative analysis of MHC ligands by mass spectrometry using stable isotope labeling" Nat Biotechnol, 2004.
Lennerz et al. (2005). "The response of autologous T cells to a human melanoma is dominated by mutated neoantigens," Proc. Natl. Acad. Sci. USA 102: 16013-16018.
Ley et al. (2008). "DNA sequencing of a cytogenetically normal acute myeloid leukaemia genome," Nature 456: 66-72.
Li et al., Cancer Genome Sequencing and Its Implications for Personalized Cancer Vaccine, Cancer 2011, 3, 4191-4211.
Maksyutov and Zagrebelnaya (1993). "ADEPT: a computer program for prediction of protein antigenic determinants," Comput. Appl. Biosci. 9: 291-297.
Mandelboim et al. (1995). "Regression of established murine carcinoma metastases following vaccination with tumour-associated antigen peptides," Nature Medicine 1: 1179-1183.
Mardis, ER. "Recurring Mutations Found by Seuencing an Acute Myeloid Leukemia Genome" New England J. Med. 361: 1058-1066, 2009.
Margulies, Marcel et al., "Genome Sequencing in Open Microfabricated High Density Picoliter Reactors" Nature, 2005.
Martinon et al. (1993). Induction of virus-specific cytotoxic T lymphocytes in vivo by liposome-entrapped mRNA. Eur. J. Immunol 23, 1719-1722.
Meyerson, M. et al. "Advances in understanding cancer genomes through second-generation sequencing" Nature Rev. Genetics. 11:685-695, 2010.
Monach et al. (1995). "A unique tumor antigen produced by a single amino acid substitution," Immunity 2: 45-59.
Mortazavi (2008). "Mapping and quantifying mammalian transcriptomes by RNA-Seq," Nature Methods 5: 621-628.
Parker et al., J. Immunol. 152 (1994), 163-175.
Parkhurst, MR. et al. "Improved Induction of Melanoma-reactive CTL with peptides from the melanoma antigen gp100 modified at HLA-A*0201-binding residues." J. Immunol. 157: 2549-2548, 1996.
Parmiani, G. et al. "Unique Human Tumor Antigens: Immunobiology and Use in Clinical Trials." The Journal of Immunology, 178: 1975-1979, 2007.
Perissi et al., Electron Spin Resonance and Differential Scanning Calorimetry as Combined Tools for the Study of Liposomes in the Presence of Long Chain Nitroxides, 106 J. of Phys. Chem. B 10468 (2002).
Pfohl et al., Biological Polyelectrolyte Complexes in Solution and Confined on Patterned Surfaces, 198-200 Colloids & Surfaces A: Physicochemical and Eng. Aspects 613 (2002).
Pilla, L. et al. "Multipeptide vaccination in cancer patients" Expert Opinion on Biological Therapy, 9: 1043-1055, 2009.
Pleasance, E. et al. "A comprehensive catalogue of somatic mutaitons from a human cancer genome," Nature, 463: 191-196, 2010.
Pleasance, E. et al. "A small-cell lung cancer genome with complex signatures of tobacco exposure." Nature, 463: 184-190, 2010.
Rammensee (2006). "Some considerations on the use of peptides and mRNA for therapeutic vaccination against cancer," Immunol Cell Biol. 84(3):290-4.
Rammansee 2008, Chapter 50: Cancer Vaccines: Some Basic Considerations, Genomic and Personalized Medicine, Hungtington and Ginsburg. E-published on Nov. 11, 2008.
Rammensee et al. (2002). "Toward patient-specific tumor antigen selection for vaccination," Immunol. Rev. 188: 164-176.
Rammensee et al., Immunogenentics, 50 (1999), 213-219.
Rao (1994). "Epitope-based vaccines: One step at a time," Proc. Indian natn. Sci. Acad. B60: 419-424.
Ressing, M. et al. "Human CTL epitopes encoded by human papillomavirus types 16E6 . . . " J. Immunol. 154:5934-5943, 1995.
Saenz-Badillos et al. (2001). "RNA as a tumor vaccine: a review of the literature," Exp Dermatol. 10(3):143-54.
Jan. 29, 2019—(CN) Office Action—App 201680010134.9—Eng Tran.
UniProtKB—P36888 (FLT3_HUMAN), last sequence update: Aug. 21, 2007.
UniProtKB—Q9NVD7 (PARVA_HUMAN), last sequence update: Oct. 1, 2000.
UniProtKB—05SW79 (CE170_HUMAN), last sequence update: Dec. 21, 2004.
Dolgin, "The Billion-Dollar Biotech," Nature, vol. 522, pp. 26-28, Jun. 4, 2015.
Segal et al. (2008). "Epitope landscape in breast and colorectal cancer," Cancer Res. 68: 889-892.
Sensi and Aanichini, Unique Tumor Antigens: Evidence for Immune Control of Genome Integrity and Immunogenic Targets for T cell-mediated Patient-Specific Immunotherapy, Clin. Cancer Res. 2006:12(17), 5023.
Sette, A. et al. "Peptide Binding to the Most Frequent HLA-A Class I Alleles Measured by Quantitative Molecular Binding Assays" Mol. Immunol. 31: 813-822, 1994.
Sette, A. et al. "The Relationship Between Class I Binding Affinity and Immunogenicity of Potential Cytotoxic T cell Epitopes." J. Immunol. 153: 5586-5592, 1994.
Shah et al. (2009). "Mutation of FOXL2 in granulosa-cell tumors of the ovary," N. Eng. J. Med. 360: 2719-2729.
Sjöblom et al. (2006). "The consensus coding sequences of human breast and colorectal cancers," Science 314: 268-274.
Stephens et al. (2005). "A screen of the complete protein kinase gene family identifies diverse patterns of somatic mutations in human breast cancer," Nature Genetics, 37: 590-592.
Thomson et al., J. Virology (1998), 72(3):2246-2252.
Toes et al. (1997). "Protective anti-tumor immunity induced by vaccination with recombinant adenoviruses encoding multiple tumor-associated cytotoxic T lymphocyte epitopes in a string-of-beads fashion," Proc. Natl. Acad. Sci. USA 94: 14660-14665.
UniProtKB, "Print-outs from the UniProtKB database concerning the CEP170, PARVA and FLT3 genes".
Van der Bruggen et al. (1991). "A gene encoding an antigen recognized by cytolytic T lymphocytes on a human melanoma," Science 254: 1643-1647.
Van Laere AS, Nguyen M, Braunschweig M. et al. A regulatory mutation in IGF2 causes a major QTL effect on muscle growth in the pig. Nature. 2003;425(6960):832-836.
Weinschenk et al. (2002). "Integrated functional genomics approach for the design of patient-individual antitumor vaccines," Cancer Res 62: 5818-5827.
Wolff et al. (1990). "Direct gene transfer into mouse muscle in vivo," Science 247: 1465-1468.
Wood et al. (2007). "The genomic landscapes of human breast and colorectal cancers," Science 318: 1108-1113.
Wortzel et al. (1983). "Multiple tumour-specific antigens expressed on a single tumour cell," Nature 304: 165-167.
Zhou et al., Hum. Gene Ther., 10(16):2719-24, 1999.
U.S. Appl. No. 61/334,866, filed May 14, 2010.
Boisguérin, V. et al., Translation of genomics-guided RNA-based personalised cancer vaccines: towards the bedside, Br J Cancer, 111(8):1469-75 (2014).
Castle, JC. et al., Exploiting the mutanome for tumor vaccination, Cancer Res., 72(5):1081-91 (2012).
Culshaw, S. et al., Assessment of Human Immune Response to Mutans Streptococcal Glucosyltransferase Peptides Selected by MHC Class II Binding Probability, International Journal of Peptide Research and Therapeutics, 13(4):525-531 (2007).
International Search Report for PCT/EP2015/053021, 6 pages (dated Aug. 18, 2016).

(56) References Cited

OTHER PUBLICATIONS

International Search Report for PCT/EP2016/052684, 6 pages (dated Aug. 18, 2016).
Overwijk, W et al., Mining the mutanome: developing highly personalized Immunotherapies based on mutational analysis of tumors, J Immunother Cancer, 1:11, 4 pages (2013).
Wick, DA. et al., Surveillance of the tumor mutanome by T cells during progression from primary to recurrent ovarian cancer, Clin Cancer Res, 20(5):1125-34 (2014).
Written Opinion for PCT/EP2015/053021, 6 pages (dated Aug. 18, 2016).
Written Opinion for PCT/EP2016/052684, 5 pages (dated Aug. 18, 2016).
Zhu, S. et al., Improving MHC binding peptide prediction by incorporating binding data of auxiliary MHC molecules, Bioinformatics, 22(13):1648-55 (2006).
International Preliminary Report on Patentability dated Aug. 24, 2017 for corresponding International Application No. PCT/EP2016/052684.
Kreiter et al., "Mutant MHC class II epitopes drive therapeutic immune responses to cancer", Nature, vol. 520, No. 7549, Apr. 22, 2015, pp. 692-696.

\* cited by examiner

SEQUENCE LISTING

<160> NUMBER OF SEQ ID NOS: 105

<210> SEQ ID NO 1
<211> LENGTH: 27
<212> TYPE: PRT
<213> ORGANISM: Artificial Sequence
<220> FEATURE:
<223> OTHER INFORMATION: Epitope

<400> SEQUENCE: 1

Phe Val Val Lys Ala Tyr Leu Pro Val Asn Glu Ser Phe Ala Phe Thr
1               5                   10                  15

Ala Asp Leu Arg Ser Asn Thr Gly Gly Gln Ala
            20                  25

<210> SEQ ID NO 2
<211> LENGTH: 27
<212> TYPE: PRT
<213> ORGANISM: Artificial Sequence
<220> FEATURE:
<223> OTHER INFORMATION: Epitope

<400> SEQUENCE: 2

Ala Asn Phe Glu Ser Gly Lys His Lys Tyr Arg Gln Thr Ala Met Phe
1               5                   10                  15

Thr Ala Thr Met Pro Pro Ala Val Glu Arg Leu
            20                  25

<210> SEQ ID NO 3
<211> LENGTH: 27
<212> TYPE: PRT
<213> ORGANISM: Artificial Sequence
<220> FEATURE:
<223> OTHER INFORMATION: Epitope

<400> SEQUENCE: 3

Thr Pro Pro Pro Glu Glu Ala Met Pro Phe Glu Phe Asn Gly Pro Ala
1               5                   10                  15

Gln Gly Asp His Ser Gln Pro Pro Leu Gln Val
            20                  25

```
<210> SEQ ID NO 4
<211> LENGTH: 27
<212> TYPE: PRT
<213> ORGANISM: Artificial Sequence
<220> FEATURE:
<223> OTHER INFORMATION: Epitope

<400> SEQUENCE: 4

Val Val Asp Arg Asn Pro Gln Phe Leu Asp Pro Val Leu Ala Tyr Leu
1               5                   10                  15

Met Lys Gly Leu Cys Glu Lys Pro Leu Ala Ser
            20                  25

<210> SEQ ID NO 5
<211> LENGTH: 27
<212> TYPE: PRT
<213> ORGANISM: Artificial Sequence
<220> FEATURE:
<223> OTHER INFORMATION: Epitope

<400> SEQUENCE: 5

Phe Arg Arg Lys Ala Phe Leu His Trp Tyr Thr Gly Glu Ala Met Asp
1               5                   10                  15

Glu Met Glu Phe Thr Glu Ala Glu Ser Asn Met
            20                  25

<210> SEQ ID NO 6
<211> LENGTH: 27
<212> TYPE: PRT
<213> ORGANISM: Artificial Sequence
<220> FEATURE:
<223> OTHER INFORMATION: Epitope

<400> SEQUENCE: 6

Ser Ser Pro Asp Glu Val Ala Leu Val Glu Gly Val Gln Ser Leu Gly
1               5                   10                  15

Phe Thr Tyr Leu Arg Leu Lys Asp Asn Tyr Met
            20                  25

<210> SEQ ID NO 7
<211> LENGTH: 27
<212> TYPE: PRT
<213> ORGANISM: Artificial Sequence
<220> FEATURE:
<223> OTHER INFORMATION: Epitope

<400> SEQUENCE: 7

Pro Lys Pro Asp Phe Ser Gln Leu Gln Arg Asn Ile Leu Pro Ser Asn
1               5                   10                  15

Pro Arg Val Thr Arg Phe His Ile Asn Trp Asp
            20                  25

<210> SEQ ID NO 8
<211> LENGTH: 27
<212> TYPE: PRT
<213> ORGANISM: Artificial Sequence
<220> FEATURE:
<223> OTHER INFORMATION: Epitope

<400> SEQUENCE: 8

Thr Ala Val Ile Thr Pro Pro Thr Thr Thr Thr Lys Lys Ala Arg Val
1               5                   10                  15

Ser Thr Pro Lys Pro Ala Thr Pro Ser Thr Asp
```

20              25

<210> SEQ ID NO 9
<211> LENGTH: 27
<212> TYPE: PRT
<213> ORGANISM: Artificial Sequence
<220> FEATURE:
<223> OTHER INFORMATION: Epitope

<400> SEQUENCE: 9

Ser Thr Ala Asn Tyr Asn Thr Ser His Leu Asn Asn Asp Val Trp Gln
1               5                   10                  15

Ile Phe Glu Asn Pro Val Asp Trp Lys Glu Lys
            20                  25

<210> SEQ ID NO 10
<211> LENGTH: 27
<212> TYPE: PRT
<213> ORGANISM: Artificial Sequence
<220> FEATURE:
<223> OTHER INFORMATION: Epitope

<400> SEQUENCE: 10

Arg Glu Gly Val Glu Leu Cys Pro Gly Asn Lys Tyr Glu Met Arg Arg
1               5                   10                  15

His Gly Thr Thr His Ser Leu Val Ile His Asp
            20                  25

<210> SEQ ID NO 11
<211> LENGTH: 27
<212> TYPE: PRT
<213> ORGANISM: Artificial Sequence
<220> FEATURE:
<223> OTHER INFORMATION: Epitope

<400> SEQUENCE: 11

Asn Ile Glu Gly Ile Asp Lys Leu Thr Gln Leu Lys Lys Pro Phe Leu
1               5                   10                  15

Val Asn Asn Lys Ile Asn Lys Ile Glu Asn Ile
            20                  25

<210> SEQ ID NO 12
<211> LENGTH: 27
<212> TYPE: PRT
<213> ORGANISM: Artificial Sequence
<220> FEATURE:
<223> OTHER INFORMATION: Epitope

<400> SEQUENCE: 12

Ile Pro Ser Gly Thr Thr Ile Leu Asn Cys Phe His Asp Val Leu Ser
1               5                   10                  15

Gly Lys Leu Ser Gly Gly Ser Pro Gly Val Pro
            20                  25

<210> SEQ ID NO 13
<211> LENGTH: 27
<212> TYPE: PRT
<213> ORGANISM: Artificial Sequence
<220> FEATURE:
<223> OTHER INFORMATION: Epitope

<400> SEQUENCE: 13

Pro Ser Lys Pro Ser Phe Gln Glu Phe Val Asp Trp Glu Asn Val Ser
1               5                   10                  15

Pro Glu Leu Asn Ser Thr Asp Gln Pro Phe Leu
            20                  25

<210> SEQ ID NO 14
<211> LENGTH: 27
<212> TYPE: PRT
<213> ORGANISM: Artificial Sequence
<220> FEATURE:
<223> OTHER INFORMATION: Epitope

<400> SEQUENCE: 14

Asp Ser Gly Ser Pro Phe Pro Ala Ala Val Ile Leu Arg Asp Ala Leu
1               5                   10                  15

His Met Ala Arg Gly Leu Lys Tyr Leu His Gln
            20                  25

<210> SEQ ID NO 15
<211> LENGTH: 27
<212> TYPE: PRT
<213> ORGANISM: Artificial Sequence
<220> FEATURE:
<223> OTHER INFORMATION: Epitope

<400> SEQUENCE: 15

Cys Gly Thr Ala Phe Phe Ile Asn Phe Ile Ala Ile Tyr His His Ala
1               5                   10                  15

Ser Arg Ala Ile Pro Phe Gly Thr Met Val Ala
            20                  25

<210> SEQ ID NO 16
<211> LENGTH: 27
<212> TYPE: PRT
<213> ORGANISM: Artificial Sequence
<220> FEATURE:
<223> OTHER INFORMATION: Epitope

<400> SEQUENCE: 16

Glu Phe Lys His Ile Lys Ala Phe Asp Arg Thr Phe Ala Asn Asn Pro
1               5                   10                  15

Gly Pro Met Val Val Phe Ala Thr Pro Gly Met
            20                  25

<210> SEQ ID NO 17
<211> LENGTH: 27
<212> TYPE: PRT
<213> ORGANISM: Artificial Sequence
<220> FEATURE:
<223> OTHER INFORMATION: Epitope

<400> SEQUENCE: 17

Glu Cys Arg Ile Thr Ser Asn Phe Val Ile Pro Ser Glu Tyr Trp Val
1               5                   10                  15

Glu Glu Lys Glu Glu Lys Gln Lys Leu Ile Gln
            20                  25

<210> SEQ ID NO 18
<211> LENGTH: 27
<212> TYPE: PRT
<213> ORGANISM: Artificial Sequence
<220> FEATURE:
<223> OTHER INFORMATION: Epitope

<400> SEQUENCE: 18

Asn His Ser Gly Leu Val Thr Phe Gln Ala Phe Ile Asp Val Met Ser
1               5                   10                  15

Arg Glu Thr Thr Asp Thr Asp Thr Ala Asp Gln
            20                  25

<210> SEQ ID NO 19
<211> LENGTH: 27
<212> TYPE: PRT
<213> ORGANISM: Artificial Sequence
<220> FEATURE:
<223> OTHER INFORMATION: Epitope

<400> SEQUENCE: 19

Gly Arg Gly His Leu Leu Gly Arg Leu Ala Ala Ile Val Gly Lys Gln
1               5                   10                  15

Val Leu Leu Gly Arg Lys Val Val Val Arg
            20                  25

<210> SEQ ID NO 20
<211> LENGTH: 27
<212> TYPE: PRT
<213> ORGANISM: Artificial Sequence
<220> FEATURE:
<223> OTHER INFORMATION: Epitope

<400> SEQUENCE: 20

Ser His Cys His Trp Asn Asp Leu Ala Val Ile Pro Ala Gly Val Val
1               5                   10                  15

His Asn Trp Asp Phe Glu Pro Arg Lys Val Ser
            20                  25

<210> SEQ ID NO 21
<211> LENGTH: 27
<212> TYPE: PRT
<213> ORGANISM: Artificial Sequence
<220> FEATURE:
<223> OTHER INFORMATION: Epitope

<400> SEQUENCE: 21

Gly Phe Ser Gln Pro Leu Arg Arg Leu Val Leu His Val Ser Ala
1               5                   10                  15

Ala Gln Ala Glu Arg Leu Ala Arg Ala Glu Glu
            20                  25

<210> SEQ ID NO 22
<211> LENGTH: 27
<212> TYPE: PRT
<213> ORGANISM: Artificial Sequence
<220> FEATURE:
<223> OTHER INFORMATION: Epitope

<400> SEQUENCE: 22

Asp Lys Pro Leu Arg Arg Asn Asn Ser Tyr Thr Ser Tyr Ile Met Ala
1               5                   10                  15

Ile Cys Gly Met Pro Leu Asp Ser Phe Arg Ala
            20                  25

<210> SEQ ID NO 23
<211> LENGTH: 27
<212> TYPE: PRT
<213> ORGANISM: Artificial Sequence
<220> FEATURE:
<223> OTHER INFORMATION: Epitope

<400> SEQUENCE: 23

Tyr Arg Gly Ala Asn Leu His Leu Glu Glu Thr Leu Ala Gly Phe Trp

```
                1               5                  10                 15
Ala Arg Leu Leu Glu Arg Leu Phe Lys Gln Leu
        20                  25

<210> SEQ ID NO 24
<211> LENGTH: 27
<212> TYPE: PRT
<213> ORGANISM: Artificial Sequence
<220> FEATURE:
<223> OTHER INFORMATION: Epitope

<400> SEQUENCE: 24

Ala Gly Thr Gln Cys Glu Tyr Trp Ala Ser Arg Ala Leu Asp Ser Glu
1               5                   10                  15

His Ser Ile Gly Ser Met Ile Gln Leu Pro Gln
            20                  25

<210> SEQ ID NO 25
<211> LENGTH: 27
<212> TYPE: PRT
<213> ORGANISM: Artificial Sequence
<220> FEATURE:
<223> OTHER INFORMATION: Epitope

<400> SEQUENCE: 25

Gln Ala Ile Val Arg Gly Cys Ser Met Pro Gly Pro Trp Arg Ser Gly
1               5                   10                  15

Arg Leu Leu Val Ser Arg Arg Trp Ser Val Glu
            20                  25

<210> SEQ ID NO 26
<211> LENGTH: 27
<212> TYPE: PRT
<213> ORGANISM: Artificial Sequence
<220> FEATURE:
<223> OTHER INFORMATION: Epitope

<400> SEQUENCE: 26

Pro Leu Leu Pro Phe Tyr Pro Pro Asp Glu Ala Leu Glu Ile Gly Leu
1               5                   10                  15

Glu Leu Asn Ser Ser Ala Leu Pro Pro Thr Glu
            20                  25

<210> SEQ ID NO 27
<211> LENGTH: 27
<212> TYPE: PRT
<213> ORGANISM: Artificial Sequence
<220> FEATURE:
<223> OTHER INFORMATION: Epitope

<400> SEQUENCE: 27

Met Lys Ala Phe Ile Phe Lys Tyr Ser Ala Lys Thr Gly Phe Thr Lys
1               5                   10                  15

Leu Ile Asp Ala Ser Arg Val Ser Glu Thr Glu
            20                  25

<210> SEQ ID NO 28
<211> LENGTH: 27
<212> TYPE: PRT
<213> ORGANISM: Artificial Sequence
<220> FEATURE:
<223> OTHER INFORMATION: Epitope

<400> SEQUENCE: 28
```

```
Val Ile Leu Pro Gln Ala Pro Ser Gly Pro Ser Tyr Ala Thr Tyr Leu
1               5                   10                  15

Gln Pro Ala Gln Ala Gln Met Leu Thr Pro Pro
            20                  25

<210> SEQ ID NO 29
<211> LENGTH: 27
<212> TYPE: PRT
<213> ORGANISM: Artificial Sequence
<220> FEATURE:
<223> OTHER INFORMATION: Epitope

<400> SEQUENCE: 29

Glu His Ile His Arg Ala Gly Gly Leu Phe Val Ala Asp Ala Ile Gln
1               5                   10                  15

Val Gly Phe Gly Arg Ile Gly Lys His Phe Trp
            20                  25

<210> SEQ ID NO 30
<211> LENGTH: 27
<212> TYPE: PRT
<213> ORGANISM: Artificial Sequence
<220> FEATURE:
<223> OTHER INFORMATION: Epitope

<400> SEQUENCE: 30

His Thr Pro Ser Ser Tyr Ile Glu Thr Leu Pro Lys Ala Ile Lys Arg
1               5                   10                  15

Arg Ile Asn Ala Leu Lys Gln Leu Gln Val Arg
            20                  25

<210> SEQ ID NO 31
<211> LENGTH: 27
<212> TYPE: PRT
<213> ORGANISM: Artificial Sequence
<220> FEATURE:
<223> OTHER INFORMATION: Epitope

<400> SEQUENCE: 31

Glu Val Ile Gln Thr Ser Lys Tyr Tyr Met Arg Asp Val Ile Ala Ile
1               5                   10                  15

Glu Ser Ala Trp Leu Leu Glu Leu Ala Pro His
            20                  25

<210> SEQ ID NO 32
<211> LENGTH: 27
<212> TYPE: PRT
<213> ORGANISM: Artificial Sequence
<220> FEATURE:
<223> OTHER INFORMATION: Epitope

<400> SEQUENCE: 32

Gly Tyr Ile Ser Arg Val Thr Ala Gly Lys Asp Ser Tyr Ile Ala Leu
1               5                   10                  15

Val Asp Lys Asn Ile Met Gly Tyr Ile Ala Ser
            20                  25

<210> SEQ ID NO 33
<211> LENGTH: 27
<212> TYPE: PRT
<213> ORGANISM: Artificial Sequence
<220> FEATURE:
<223> OTHER INFORMATION: Epitope

<400> SEQUENCE: 33
```

```
Ser His Asp Ser Arg Lys Ser Thr Ser Phe Met Ser Val Asn Pro Ser
1               5                   10                  15

Lys Glu Ile Lys Ile Val Ser Ala Val Arg Arg
            20                  25
```

<210> SEQ ID NO 34
<211> LENGTH: 27
<212> TYPE: PRT
<213> ORGANISM: Artificial Sequence
<220> FEATURE:
<223> OTHER INFORMATION: Epitope

<400> SEQUENCE: 34

```
Ala Ala Tyr Lys Gly His His Tyr Pro Gly Pro Gly Asn Tyr Phe Trp
1               5                   10                  15

Lys Cys Leu Phe Met Ser Gly Leu Ser Glu Val
            20                  25
```

<210> SEQ ID NO 35
<211> LENGTH: 27
<212> TYPE: PRT
<213> ORGANISM: Artificial Sequence
<220> FEATURE:
<223> OTHER INFORMATION: Epitope

<400> SEQUENCE: 35

```
Glu Gly Asp Pro Cys Leu Arg Ser Ser Asp Cys Ile Asp Glu Phe Cys
1               5                   10                  15

Cys Ala Arg His Phe Trp Thr Lys Ile Cys Lys
            20                  25
```

<210> SEQ ID NO 36
<211> LENGTH: 27
<212> TYPE: PRT
<213> ORGANISM: Artificial Sequence
<220> FEATURE:
<223> OTHER INFORMATION: Epitope

<400> SEQUENCE: 36

```
Cys Gly Tyr Pro Leu Cys Gln Lys Lys Leu Gly Val Ile Ser Lys Gln
1               5                   10                  15

Lys Tyr Arg Ile Ser Thr Lys Thr Asn Lys Val
            20                  25
```

<210> SEQ ID NO 37
<211> LENGTH: 27
<212> TYPE: PRT
<213> ORGANISM: Artificial Sequence
<220> FEATURE:
<223> OTHER INFORMATION: Epitope

<400> SEQUENCE: 37

```
Val Thr Ser Ile Pro Ser Val Ser Asn Ala Leu Asn Trp Lys Glu Phe
1               5                   10                  15

Ser Phe Ile Gln Ser Thr Leu Gly Tyr Val Ala
            20                  25
```

<210> SEQ ID NO 38
<211> LENGTH: 27
<212> TYPE: PRT
<213> ORGANISM: Artificial Sequence
<220> FEATURE:
<223> OTHER INFORMATION: Epitope

```
<400> SEQUENCE: 38

Lys Thr Thr Leu Ser His Thr Gln Asp Ser Ser Gln Ser Leu Gln Ser
1               5                   10                  15

Ser Ser Asp Ser Ser Lys Ser Ser Arg Cys Ser
            20                  25

<210> SEQ ID NO 39
<211> LENGTH: 27
<212> TYPE: PRT
<213> ORGANISM: Artificial Sequence
<220> FEATURE:
<223> OTHER INFORMATION: Epitope

<400> SEQUENCE: 39

Pro Ala Pro Arg Ala Val Leu Thr Gly His Asp His Glu Ile Val Cys
1               5                   10                  15

Val Ser Val Cys Ala Glu Leu Gly Leu Val Ile
            20                  25

<210> SEQ ID NO 40
<211> LENGTH: 27
<212> TYPE: PRT
<213> ORGANISM: Artificial Sequence
<220> FEATURE:
<223> OTHER INFORMATION: Epitope

<400> SEQUENCE: 40

Leu His Ser Gly Gln Asn His Leu Lys Glu Met Ala Ile Ser Val Leu
1               5                   10                  15

Glu Ala Arg Ala Cys Ala Ala Ala Gly Gln Ser
            20                  25

<210> SEQ ID NO 41
<211> LENGTH: 27
<212> TYPE: PRT
<213> ORGANISM: Artificial Sequence
<220> FEATURE:
<223> OTHER INFORMATION: Epitope

<400> SEQUENCE: 41

Asn Cys Lys Tyr Asp Thr Lys Cys Thr Lys Ala Asp Cys Leu Phe Thr
1               5                   10                  15

His Met Ser Arg Arg Ala Ser Ile Leu Thr Pro
            20                  25

<210> SEQ ID NO 42
<211> LENGTH: 27
<212> TYPE: PRT
<213> ORGANISM: Artificial Sequence
<220> FEATURE:
<223> OTHER INFORMATION: Epitope

<400> SEQUENCE: 42

Leu Arg Ser Ser Leu Val Asn Asn Arg Thr Gln Ala Lys Ile Ala Glu
1               5                   10                  15

Glu Leu Gly Met Gln Glu Tyr Ala Ile Thr Asn
            20                  25

<210> SEQ ID NO 43
<211> LENGTH: 27
<212> TYPE: PRT
<213> ORGANISM: Artificial Sequence
<220> FEATURE:
<223> OTHER INFORMATION: Epitope
```

```
<400> SEQUENCE: 43

Ile Pro His Asn Pro Arg Val Ala Val Lys Thr Thr Asn Asn Leu Val
1               5                   10                  15

Met Lys Asn Ser Val Cys Leu Glu Arg Asp Ser
            20                  25

<210> SEQ ID NO 44
<211> LENGTH: 27
<212> TYPE: PRT
<213> ORGANISM: Artificial Sequence
<220> FEATURE:
<223> OTHER INFORMATION: Epitope

<400> SEQUENCE: 44

Leu Ala Ala Gln Ser Leu Gly Glu Pro Ala Thr Gln Ile Thr Leu Asn
1               5                   10                  15

Thr Phe His Tyr Ala Gly Val Ser Ala Lys Asn
            20                  25

<210> SEQ ID NO 45
<211> LENGTH: 27
<212> TYPE: PRT
<213> ORGANISM: Artificial Sequence
<220> FEATURE:
<223> OTHER INFORMATION: Epitope

<400> SEQUENCE: 45

Gln Gly Val Thr Val Leu Ala Val Ser Ala Val Tyr Asp Ile Phe Val
1               5                   10                  15

Phe His Arg Leu Lys Met Lys Gln Ile Leu Pro
            20                  25

<210> SEQ ID NO 46
<211> LENGTH: 27
<212> TYPE: PRT
<213> ORGANISM: Artificial Sequence
<220> FEATURE:
<223> OTHER INFORMATION: Epitope

<400> SEQUENCE: 46

Ala His Ile Arg Gly Ala Lys His Gln Lys Val Val Thr Leu His Thr
1               5                   10                  15

Lys Leu Gly Lys Pro Ile Pro Ser Thr Glu Pro
            20                  25

<210> SEQ ID NO 47
<211> LENGTH: 27
<212> TYPE: PRT
<213> ORGANISM: Artificial Sequence
<220> FEATURE:
<223> OTHER INFORMATION: Epitope

<400> SEQUENCE: 47

Glu Leu Ala Trp Glu Ile Asp Arg Lys Val Leu His Gln Asn Arg Leu
1               5                   10                  15

Gln Arg Thr Pro Ile Lys Leu Gln Cys Phe Ala
            20                  25

<210> SEQ ID NO 48
<211> LENGTH: 27
<212> TYPE: PRT
<213> ORGANISM: Artificial Sequence
<220> FEATURE:
```

```
<223> OTHER INFORMATION: Epitope

<400> SEQUENCE: 48

Phe Leu Lys Asp Arg Leu Leu Glu Asp Lys Ile Ala Val Leu Leu
1               5                   10                  15

Asp Glu Val Ala Glu Asp Met Gly Lys Cys His
            20                  25

<210> SEQ ID NO 49
<211> LENGTH: 27
<212> TYPE: PRT
<213> ORGANISM: Artificial Sequence
<220> FEATURE:
<223> OTHER INFORMATION: Epitope

<400> SEQUENCE: 49

Asn Asp Glu Pro Asp Leu Asp Pro Val Gln Glu Leu Ile Tyr Asp Leu
1               5                   10                  15

Arg Ser Gln Cys Asp Ala Ile Arg Val Thr Lys
            20                  25

<210> SEQ ID NO 50
<211> LENGTH: 27
<212> TYPE: PRT
<213> ORGANISM: Artificial Sequence
<220> FEATURE:
<223> OTHER INFORMATION: Epitope

<400> SEQUENCE: 50

Asp Ala Ala Ala Leu Gln Met Ile Ile Ala Tyr Ala Tyr Arg Gly Asn
1               5                   10                  15

Leu Ala Val Asn Asp Ser Thr Val Glu Gln Leu
            20                  25

<210> SEQ ID NO 51
<211> LENGTH: 27
<212> TYPE: PRT
<213> ORGANISM: Artificial Sequence
<220> FEATURE:
<223> OTHER INFORMATION: Epitope

<400> SEQUENCE: 51

Lys Asp Tyr Thr Ala Ala Gly Phe Ser Ser Phe Gln Lys Leu Arg Leu
1               5                   10                  15

Asp Leu Thr Ser Met Gln Ile Ile Thr Thr Asp
            20                  25

<210> SEQ ID NO 52
<211> LENGTH: 27
<212> TYPE: PRT
<213> ORGANISM: Artificial Sequence
<220> FEATURE:
<223> OTHER INFORMATION: Epitope

<400> SEQUENCE: 52

Ala Val Lys Glu Glu Asp Ser Leu His Trp Gln Arg Pro Glu Asp Val
1               5                   10                  15

Gln Lys Val Lys Ala Leu Ser Phe Tyr Gln Pro
            20                  25

<210> SEQ ID NO 53
<211> LENGTH: 27
<212> TYPE: PRT
<213> ORGANISM: Artificial Sequence
```

```
<220> FEATURE:
<223> OTHER INFORMATION: Epitope

<400> SEQUENCE: 53

Phe Ala Ile Cys Phe Ser Cys Leu Leu Ala His Ala Leu Asn Leu Ile
1               5                   10                  15

Lys Leu Val Arg Gly Arg Lys Pro Leu Ser Trp
            20                  25

<210> SEQ ID NO 54
<211> LENGTH: 23
<212> TYPE: PRT
<213> ORGANISM: Artificial Sequence
<220> FEATURE:
<223> OTHER INFORMATION: Epitope

<400> SEQUENCE: 54

Met Gly Ala Ala Ile Ser Gln Gly Ala Ile Ala Ile Val Cys Asn
1               5                   10                  15

Gly Leu Val Gly Phe Leu Leu
            20

<210> SEQ ID NO 55
<211> LENGTH: 27
<212> TYPE: PRT
<213> ORGANISM: Artificial Sequence
<220> FEATURE:
<223> OTHER INFORMATION: Epitope

<400> SEQUENCE: 55

Glu Lys Tyr Pro Arg Thr Pro Lys Cys Ala Arg Cys Gly Asn His Gly
1               5                   10                  15

Val Val Ser Ala Leu Lys Gly His Lys Arg Tyr
            20                  25

<210> SEQ ID NO 56
<211> LENGTH: 27
<212> TYPE: PRT
<213> ORGANISM: Artificial Sequence
<220> FEATURE:
<223> OTHER INFORMATION: Epitope

<400> SEQUENCE: 56

Ser His Arg Ser Cys Ser His Gln Thr Ser Ala Pro Ser Pro Lys Ala
1               5                   10                  15

Leu Ala His Asn Gly Thr Pro Arg Asn Ala Ile
            20                  25

<210> SEQ ID NO 57
<211> LENGTH: 27
<212> TYPE: PRT
<213> ORGANISM: Artificial Sequence
<220> FEATURE:
<223> OTHER INFORMATION: Epitope

<400> SEQUENCE: 57

Lys Glu Leu Leu Gln Phe Lys Lys Leu Lys Lys Gln Asn Leu Gln Gln
1               5                   10                  15

Met Gln Ala Glu Ser Gly Phe Val Gln His Val
            20                  25

<210> SEQ ID NO 58
<211> LENGTH: 27
<212> TYPE: PRT
```

```
<213> ORGANISM: Artificial Sequence
<220> FEATURE:
<223> OTHER INFORMATION: Epitope

<400> SEQUENCE: 58

Arg Lys Gly Glu Arg Glu Met Gln Asp Ala His Val Ser Leu Asn
1               5                   10                  15

Asp Ile Thr Gln Glu Cys Asn Pro Pro Ser Ser
            20                  25

<210> SEQ ID NO 59
<211> LENGTH: 27
<212> TYPE: PRT
<213> ORGANISM: Artificial Sequence
<220> FEATURE:
<223> OTHER INFORMATION: Epitope

<400> SEQUENCE: 59

Arg Val Glu Lys Leu Gln Leu Glu Ser Glu Leu Asn Glu Ser Arg Thr
1               5                   10                  15

Glu Cys Ile Thr Ala Thr Ser Gln Met Thr Ala
            20                  25

<210> SEQ ID NO 60
<211> LENGTH: 27
<212> TYPE: PRT
<213> ORGANISM: Artificial Sequence
<220> FEATURE:
<223> OTHER INFORMATION: Epitope

<400> SEQUENCE: 60

Asp Ser Val Val Ile Phe Ser Gly Glu Gly Ser Asp Glu Phe Thr Gln
1               5                   10                  15

Gly Tyr Ile Tyr Phe His Lys Ala Pro Ser Pro
            20                  25

<210> SEQ ID NO 61
<211> LENGTH: 27
<212> TYPE: PRT
<213> ORGANISM: Artificial Sequence
<220> FEATURE:
<223> OTHER INFORMATION: Epitope

<400> SEQUENCE: 61

Pro Gln Thr Ser Pro Thr Gly Ile Leu Pro Thr Thr Ser Asn Ser Ile
1               5                   10                  15

Ser Thr Ser Glu Met Thr Trp Lys Ser Ser Leu
            20                  25

<210> SEQ ID NO 62
<211> LENGTH: 27
<212> TYPE: PRT
<213> ORGANISM: Artificial Sequence
<220> FEATURE:
<223> OTHER INFORMATION: Epitope

<400> SEQUENCE: 62

Trp Ile Gly Gly Ser Ile Leu Ala Ser Leu Ser Thr Phe His Gln Met
1               5                   10                  15

Trp Ile Ser Lys Gln Glu Tyr Asp Glu Ser Gly
            20                  25

<210> SEQ ID NO 63
<211> LENGTH: 27
```

```
<212> TYPE: PRT
<213> ORGANISM: Artificial Sequence
<220> FEATURE:
<223> OTHER INFORMATION: Epitope

<400> SEQUENCE: 63

Ser Ala Leu Gly Ser Leu Ala Leu Met Ile Trp Leu Met Thr Thr Pro
1               5                   10                  15

His Ser His Glu Thr Glu Gln Lys Arg Leu Gly
            20                  25

<210> SEQ ID NO 64
<211> LENGTH: 26
<212> TYPE: PRT
<213> ORGANISM: Artificial Sequence
<220> FEATURE:
<223> OTHER INFORMATION: Epitope

<400> SEQUENCE: 64

Asp Leu Arg Thr Ala Ala Tyr Val Asn Ala Ile Glu Lys Ile Phe Lys
1               5                   10                  15

Val Tyr Asn Glu Ala Gly Val Thr Phe Thr
            20                  25

<210> SEQ ID NO 65
<211> LENGTH: 27
<212> TYPE: PRT
<213> ORGANISM: Artificial Sequence
<220> FEATURE:
<223> OTHER INFORMATION: Epitope

<400> SEQUENCE: 65

Lys Leu Cys Leu Glu Leu Leu Asn Val Gly Val Glu Ser Asn Leu Ile
1               5                   10                  15

Leu Lys Gly Val Ile Leu Leu Ile Val Asp Lys
            20                  25

<210> SEQ ID NO 66
<211> LENGTH: 27
<212> TYPE: PRT
<213> ORGANISM: Artificial Sequence
<220> FEATURE:
<223> OTHER INFORMATION: Epitope

<400> SEQUENCE: 66

Asn Val His Tyr Glu Asn Tyr Arg Ser Arg Lys Leu Ala Thr Val Thr
1               5                   10                  15

Tyr Asn Gly Val Asp Asn Asn Lys Asn Lys Gly
            20                  25

<210> SEQ ID NO 67
<211> LENGTH: 27
<212> TYPE: PRT
<213> ORGANISM: Artificial Sequence
<220> FEATURE:
<223> OTHER INFORMATION: Epitope

<400> SEQUENCE: 67

Tyr Thr Val Ser Val Val Ala Leu His Asp Asp Met Glu Asn Gln Pro
1               5                   10                  15

Leu Ile Gly Ile Gln Ser Thr Ala Ile Pro Ala
            20                  25

<210> SEQ ID NO 68
```

```
<211> LENGTH: 27
<212> TYPE: PRT
<213> ORGANISM: Artificial Sequence
<220> FEATURE:
<223> OTHER INFORMATION: Epitope

<400> SEQUENCE: 68

Lys Pro Ser Thr Leu Arg Glu Leu Glu Arg Tyr Val Leu Ala Cys Leu
1               5                   10                  15

Arg Lys Lys Pro Arg Lys Pro Tyr Thr Ile Arg
            20                  25

<210> SEQ ID NO 69
<211> LENGTH: 20
<212> TYPE: PRT
<213> ORGANISM: Artificial Sequence
<220> FEATURE:
<223> OTHER INFORMATION: Epitope

<400> SEQUENCE: 69

Lys Phe Met Glu Arg Asp Pro Asp Glu Leu Arg Phe Asn Thr Ile Ala
1               5                   10                  15

Leu Ser Ala Ala
            20

<210> SEQ ID NO 70
<211> LENGTH: 27
<212> TYPE: PRT
<213> ORGANISM: Artificial Sequence
<220> FEATURE:
<223> OTHER INFORMATION: Epitope

<400> SEQUENCE: 70

Leu His Ser Gly Gln Asn His Leu Lys Glu Met Ala Ile Ser Val Leu
1               5                   10                  15

Glu Ala Arg Ala Cys Ala Ala Ala Gly Gln Ser
            20                  25

<210> SEQ ID NO 71
<211> LENGTH: 27
<212> TYPE: PRT
<213> ORGANISM: Artificial Sequence
<220> FEATURE:
<223> OTHER INFORMATION: Epitope

<400> SEQUENCE: 71

Asp Thr Leu Ser Ala Met Ser Asn Pro Arg Ala Met Gln Val Leu Leu
1               5                   10                  15

Gln Ile Gln Gln Gly Leu Gln Thr Leu Ala Thr
            20                  25

<210> SEQ ID NO 72
<211> LENGTH: 27
<212> TYPE: PRT
<213> ORGANISM: Artificial Sequence
<220> FEATURE:
<223> OTHER INFORMATION: Epitope

<400> SEQUENCE: 72

Asp Gly Gln Leu Glu Leu Leu Ala Gln Gly Ala Leu Asp Asn Ala Leu
1               5                   10                  15

Ser Ser Met Gly Ala Leu His Ala Leu Arg Pro
            20                  25
```

```
<210> SEQ ID NO 73
<211> LENGTH: 27
<212> TYPE: PRT
<213> ORGANISM: Artificial Sequence
<220> FEATURE:
<223> OTHER INFORMATION: Epitope

<400> SEQUENCE: 73

Trp Lys Gly Gly Pro Val Lys Ile Asp Pro Leu Ala Leu Met Gln Ala
1               5                   10                  15

Ile Glu Arg Tyr Leu Val Val Arg Gly Tyr Gly
            20                  25

<210> SEQ ID NO 74
<211> LENGTH: 27
<212> TYPE: PRT
<213> ORGANISM: Artificial Sequence
<220> FEATURE:
<223> OTHER INFORMATION: Epitope

<400> SEQUENCE: 74

Gln Asp Ile Asn Asp Asn Asn Pro Ser Phe Pro Thr Gly Lys Met Lys
1               5                   10                  15

Leu Glu Ile Ser Glu Ala Leu Ala Pro Gly Thr
            20                  25

<210> SEQ ID NO 75
<211> LENGTH: 27
<212> TYPE: PRT
<213> ORGANISM: Artificial Sequence
<220> FEATURE:
<223> OTHER INFORMATION: Epitope

<400> SEQUENCE: 75

Ser Asp Pro Arg Ala Ala Tyr Phe Arg Gln Ala Glu Asn Asp Met Tyr
1               5                   10                  15

Ile Arg Met Ala Leu Leu Ala Thr Val Leu Gly
            20                  25

<210> SEQ ID NO 76
<211> LENGTH: 27
<212> TYPE: PRT
<213> ORGANISM: Artificial Sequence
<220> FEATURE:
<223> OTHER INFORMATION: Epitope

<400> SEQUENCE: 76

Met Asp Leu Leu Ala Phe Glu Arg Lys Leu Asp Gln Thr Val Met Arg
1               5                   10                  15

Lys Arg Leu Asp Ile Gln Glu Ala Leu Lys Arg
            20                  25

<210> SEQ ID NO 77
<211> LENGTH: 27
<212> TYPE: PRT
<213> ORGANISM: Artificial Sequence
<220> FEATURE:
<223> OTHER INFORMATION: Epitope

<400> SEQUENCE: 77

Ile Thr Thr Cys Leu Ala Val Gly Gly Leu Asp Val Lys Phe Gln Glu
1               5                   10                  15

Ala Ala Leu Arg Ala Ala Pro Asp Ile Leu Ile
            20                  25
```

```
<210> SEQ ID NO 78
<211> LENGTH: 27
<212> TYPE: PRT
<213> ORGANISM: Artificial Sequence
<220> FEATURE:
<223> OTHER INFORMATION: Epitope

<400> SEQUENCE: 78

Lys Ala Arg Leu Lys Ser Lys Asp Val Lys Leu Ala Glu Ala His Gln
1               5                   10                  15

Gln Glu Cys Cys Gln Lys Phe Glu Gln Leu Ser
            20                  25

<210> SEQ ID NO 79
<211> LENGTH: 27
<212> TYPE: PRT
<213> ORGANISM: Artificial Sequence
<220> FEATURE:
<223> OTHER INFORMATION: Epitope

<400> SEQUENCE: 79

Gly Glu Val Pro Pro Gln Lys Leu Gln Ala Leu Gln Arg Ala Leu Gln
1               5                   10                  15

Ser Glu Phe Cys Asn Ala Val Arg Glu Val Tyr
            20                  25

<210> SEQ ID NO 80
<211> LENGTH: 15
<212> TYPE: PRT
<213> ORGANISM: Artificial Sequence
<220> FEATURE:
<223> OTHER INFORMATION: Epitope

<400> SEQUENCE: 80

Asp Trp Glu Asn Val Ser Pro Glu Leu Asn Ser Thr Asp Gln Pro
1               5                   10                  15

<210> SEQ ID NO 81
<211> LENGTH: 14
<212> TYPE: PRT
<213> ORGANISM: Artificial Sequence
<220> FEATURE:
<223> OTHER INFORMATION: Epitope

<400> SEQUENCE: 81

Asp Trp Glu Asn Val Ser Pro Glu Leu Asn Ser Thr Asp Gln
1               5                   10

<210> SEQ ID NO 82
<211> LENGTH: 13
<212> TYPE: PRT
<213> ORGANISM: Artificial Sequence
<220> FEATURE:
<223> OTHER INFORMATION: Epitope

<400> SEQUENCE: 82

Asp Trp Glu Asn Val Ser Pro Glu Leu Asn Ser Thr Asp
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Epitope
```

```
<400> SEQUENCE: 83

Asp Trp Glu Asn Val Ser Pro Glu Leu Asn Ser Thr
1               5                   10

<210> SEQ ID NO 84
<211> LENGTH: 11
<212> TYPE: PRT
<213> ORGANISM: Artificial Sequence
<220> FEATURE:
<223> OTHER INFORMATION: Epitope

<400> SEQUENCE: 84

Asp Trp Glu Asn Val Ser Pro Glu Leu Asn Ser
1               5                   10

<210> SEQ ID NO 85
<211> LENGTH: 14
<212> TYPE: PRT
<213> ORGANISM: Artificial Sequence
<220> FEATURE:
<223> OTHER INFORMATION: Epitope

<400> SEQUENCE: 85

Trp Glu Asn Val Ser Pro Glu Leu Asn Ser Thr Asp Gln Pro
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Epitope

<400> SEQUENCE: 86

Trp Glu Asn Val Ser Pro Glu Leu Asn Ser Thr Asp
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Epitope

<400> SEQUENCE: 87

Trp Glu Asn Val Ser Pro Glu Leu Asn Ser Thr
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Epitope

<400> SEQUENCE: 88

Glu Asn Val Ser Pro Glu Leu Asn Ser Thr Asp Gln Pro
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Epitope

<400> SEQUENCE: 89
```

```
Asn Val Ser Pro Glu Leu Asn Ser Thr Asp Gln Pro
1               5                   10
```

<210> SEQ ID NO 90
<211> LENGTH: 11
<212> TYPE: PRT
<213> ORGANISM: Artificial Sequence
<220> FEATURE:
<223> OTHER INFORMATION: Epitope

<400> SEQUENCE: 90

```
Val Ser Pro Glu Leu Asn Ser Thr Asp Gln Pro
1               5                   10
```

<210> SEQ ID NO 91
<211> LENGTH: 15
<212> TYPE: PRT
<213> ORGANISM: Artificial Sequence
<220> FEATURE:
<223> OTHER INFORMATION: Linker Sequence
<220> FEATURE:
<221> NAME/KEY: REPEAT
<222> LOCATION: (1)..(3)
<223> OTHER INFORMATION: Portion of sequence repeated a times, wherein a
      is independently a number selected from 0, 1, 2, 3, 4, 5, 6, 7, 8,
      9, 10, 11, 12, 13, 14, 15, 16, 17, 18, 19, or 20
<220> FEATURE:
<221> NAME/KEY: REPEAT
<222> LOCATION: (4)..(6)
<223> OTHER INFORMATION: Portion of sequence repeated b times, wherein b
      is independently a number selected from 0, 1, 2, 3, 4, 5, 6, 7, 8,
      9, 10, 11, 12, 13, 14, 15, 16, 17, 18, 19, or 20
<220> FEATURE:
<221> NAME/KEY: REPEAT
<222> LOCATION: (7)..(9)
<223> OTHER INFORMATION: Portion of sequence repeated c times, wherein c
      is independently a number selected from 0, 1, 2, 3, 4, 5, 6, 7, 8,
      9, 10, 11, 12, 13, 14, 15, 16, 17, 18, 19, or 20
<220> FEATURE:
<221> NAME/KEY: REPEAT
<222> LOCATION: (10)..(12)
<223> OTHER INFORMATION: Portion of sequence repeated d times, wherein d
      is independently a number selected from 0, 1, 2, 3, 4, 5, 6, 7, 8,
      9, 10, 11, 12, 13, 14, 15, 16, 17, 18, 19, or 20
<220> FEATURE:
<221> NAME/KEY: REPEAT
<222> LOCATION: (13)..(15)
<223> OTHER INFORMATION: Portion of sequence repeated e times, wherein e
      is independently a number selected from 0, 1, 2, 3, 4, 5, 6, 7, 8,
      9, 10, 11, 12, 13, 14, 15, 16, 17, 18, 19, or 20
<220> FEATURE:
<221> NAME/KEY: MISC_FEATURE
<222> LOCATION: (1)..(15)
<223> OTHER INFORMATION: a + b + c + d + e are different from 0 and
      preferably are 2 or more, 3 or more, 4 or more or 5 or more

<400> SEQUENCE: 91

```
Gly Gly Ser Gly Ser Ser Gly Gly Gly Ser Ser Gly Gly Ser Gly
1               5                   10                  15
```

<210> SEQ ID NO 92
<211> LENGTH: 9
<212> TYPE: PRT
<213> ORGANISM: Artificial Sequence
<220> FEATURE:
<223> OTHER INFORMATION: Linker Sequence

<400> SEQUENCE: 92

```
Gly Gly Ser Gly Gly Gly Gly Ser Gly
1               5
```

```
<210> SEQ ID NO 93
<211> LENGTH: 11
<212> TYPE: DNA
<213> ORGANISM: Mus musculus

<400> SEQUENCE: 93
ttcaggaccc a                                                          11

<210> SEQ ID NO 94
<211> LENGTH: 16
<212> TYPE: DNA
<213> ORGANISM: Mus musculus

<400> SEQUENCE: 94
ttcaggaccc acacga                                                     16

<210> SEQ ID NO 95
<211> LENGTH: 27
<212> TYPE: DNA
<213> ORGANISM: Mus musculus

<400> SEQUENCE: 95
ttcaggaccc acacgacggg aagacaa                                         27

<210> SEQ ID NO 96
<211> LENGTH: 29
<212> TYPE: DNA
<213> ORGANISM: Mus musculus

<400> SEQUENCE: 96
ttcaggacca acacgacggg aagacaagt                                       29

<210> SEQ ID NO 97
<211> LENGTH: 27
<212> TYPE: DNA
<213> ORGANISM: Mus musculus

<400> SEQUENCE: 97
caggacccac acgacgggta gacaagt                                         27

<210> SEQ ID NO 98
<211> LENGTH: 23
<212> TYPE: DNA
<213> ORGANISM: Mus musculus

<400> SEQUENCE: 98
acccacacga cgggtagaca agt                                             23

<210> SEQ ID NO 99
<211> LENGTH: 23
<212> TYPE: DNA
<213> ORGANISM: Mus musculus

<400> SEQUENCE: 99
acccacacga gccctagaca agt                                             23

<210> SEQ ID NO 100
<211> LENGTH: 15
<212> TYPE: DNA
<213> ORGANISM: Mus musculus

<400> SEQUENCE: 100
gacgggaaga caagt                                                      15
```

<210> SEQ ID NO 101
<211> LENGTH: 52
<212> TYPE: DNA
<213> ORGANISM: Artificial Sequence
<220> FEATURE:
<223> OTHER INFORMATION: Idealized Gene

<400> SEQUENCE: 101
tgcaagaacg cgtacttatt cgccgccatg attatgacca gtgtttccag tc         52

<210> SEQ ID NO 102
<211> LENGTH: 48
<212> TYPE: DNA
<213> ORGANISM: Artificial Sequence
<220> FEATURE:
<223> OTHER INFORMATION: Idealized Gene

<400> SEQUENCE: 102
caagaacgcg tacttattcg ccaccatgat tatgaccagt gtttccag              48

<210> SEQ ID NO 103
<211> LENGTH: 46
<212> TYPE: DNA
<213> ORGANISM: Artificial Sequence
<220> FEATURE:
<223> OTHER INFORMATION: Idealized Gene

<400> SEQUENCE: 103
aacgcgtact tattcgccac catgattatg accagtgttt ccagtc                46

<210> SEQ ID NO 104
<211> LENGTH: 46
<212> TYPE: DNA
<213> ORGANISM: Artificial Sequence
<220> FEATURE:
<223> OTHER INFORMATION: Idealized Gene

<400> SEQUENCE: 104
tgcaagaacg cgtacttatt cgccgccatg attatgacca gtgttt                46

<210> SEQ ID NO 105
<211> LENGTH: 10
<212> TYPE: DNA
<213> ORGANISM: Artificial Sequence
<220> FEATURE:
<223> OTHER INFORMATION: Synthetic Construct

<400> SEQUENCE: 105
ggaaactttc                                                        10

PREDICTING T CELL EPITOPES USEFUL FOR VACCINATION

CROSS REFERENCE TO RELATED APPLICATIONS

This application is a U.S. National Phase patent/application of PCT/EP2016/052684, filed on Feb. 9, 2016, which claims priority to International Patent Application No. PCT/EP2015/053021, filed on Feb. 12, 2015, the disclosures of each of which are hereby incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392041500SeqList.txt, date recorded: Aug. 10, 2017, size: 33 KB).

TECHNICAL FIELD OF THE INVENTION

The present invention relates to methods for predicting T cell epitopes useful for vaccination. In particular, the present invention relates to methods for predicting whether modifications in peptides or polypeptides such as tumor-associated neoantigens are immunogenic and, in particular, useful for vaccination, or for predicting which of such modifications are most immunogenic and, in particular, most useful for vaccination. The methods of the invention may be used, in particular, for the provision of vaccines which are specific for a patient's tumor and, thus, in the context of personalized cancer vaccines.

BACKGROUND OF THE INVENTION

Mutations are regarded as ideal targets for cancer immunotherapy. As neo-epitopes with strict lack of expression in any healthy tissue, they are expected to be safe and could bypass the central tolerance mechanisms. The systematic use of mutations for vaccine approaches, however, is hampered by the uniqueness of the repertoire of mutations ("the mutanome") in every patient's tumor (Alexandrov. L. B., et al., Nature 500, 415 (2013)). We have recently proposed a personalized immunotherapy approach targeting the spectrum of individual mutations (Castle, J. C., et al., Cancer Res 72, 1081 (2012)).

However, (here is a need for a model to predict whether an epitope, in particular a neo-epitope, will induce efficient immunity and, thus, will be useful in vaccination.

Here we show in three independent murine tumor models that a considerable fraction of non-synonymous cancer mutations is immunogenic and that unexpectedly the immunogenic mutanome is pre-dominantly recognized by CD4+ T cells ("the CD4+ immunome"). Vaccination with such CD4+ immunogenic mutations confers strong anti-tumour activity. Encouraged by these findings we set up a process comprising mutation detection by exome sequencing, selection of vaccine targets by solely bioinformatical prioritization of mutated epitopes predicted to be abundantly expressed and good MHC class II binders and rapid production of synthetic mRNA vaccines encoding multiple of these mutated epitopes. We show that vaccination with such poly-neo-epitopic mRNA vaccines induces potent tumor control and complete rejection of established aggressively growing tumors in mice. Moreover, we demonstrate that CD4+ T cell neo-epitope vaccination induces CTL responses against an independent immunodominant antigen in tumor bearing mice indicating orchestration of antigen spread. Finally, we demonstrate by analyses of corresponding human cancer types with the same bioinformatical algorithms the abundance of mutations predicted to bind to MHC class II in human cancers as well. Thus, the tailored immunotherapy approach introduced here may be regarded as a universally applicable blueprint for comprehensive exploitation of the huge neo-epitope target repertoire of cancers enabling targeting of even patient's tumour with "just in time" produced vaccines.

DESCRIPTION OF INVENTION

Summary of the Invention

In one aspect, the present invention relates to a method for predicting immunogenic amino acid modifications, the method comprising the steps:

a) ascertaining a score for binding of a modified peptide which is a fragment of a modified protein to one or more MHC class II molecules, and b) ascertaining a score for expression or abundance of the modified protein.

In one embodiment, a score for binding to one or more MHC class II molecules indicating binding to one or more MHC class II molecules and a score for expression or abundance of the modified protein indicating expression, high level of expression or abundance of the modified protein indicates that the modification or modified peptide is immunogenic.

In a further aspect, the present invention relates to a method for selecting and/or ranking immunogenic amino acid modifications, the method comprising the steps:

a) ascertaining a score for binding of a modified peptide which is a fragment of a modified protein to one or more MHC class II molecules, and b) ascertaining a score for expression or abundance of the modified protein, wherein the method comprises performing steps a) and b) on two or more different modifications.

In one embodiment, the different modifications are present in the same and/or in different proteins.

In one embodiment, the method comprises comparing the scores of said two or more different modifications. In one embodiment, the scores of said two or more different modifications are compared by ranking the different modifications by their MHC class II binding scores and removing modifications with an expression or abundance of less than a given threshold.

In one embodiment of all aspects of the invention, the score for binding to one or more MHC class II molecules reflects a probability for binding to one or more MHC class II molecules. In one embodiment, the score for binding to one or more MHC class II molecules is ascertained by a process comprising a sequence comparison with a database of MHC class II-binding motifs.

In one embodiment of all aspects of the invention, the method comprises performing step a) on two or more different modified peptides, said two or more different modified peptides comprising the same modification(s). In one embodiment, the two or more different modified peptides comprising the same modification(s) comprise different fragments of a modified protein, said different fragments comprising the same modification(s) present in the protein. In one embodiment, the two or more different modified peptides comprising the same modification(s) comprise different potential MHC class II binding fragments of a modified protein, said fragments comprising the same modification(s) present in the protein. In one embodiment, the method further comprises selecting (the) modified peptide(s) from the two or more different modified peptides comprising the same modification(s) having a probability or having the highest probability for binding to one or more MHC class II molecules. In one embodiment, the two or more different modified peptides comprising the same modification(s) differ in length and/or position of the modification(s). In one embodiment, the best score for binding to one or more MHC class II molecules of the two or more different modified peptides comprising the same modification(s) is assigned to the modification(s).

In one embodiment of all aspects of the invention, ascertaining a score for expression or abundance of a modified protein comprises determining the level of expression of the protein to which the modification is associated and determining the frequency of the modified protein among the protein to which the modification is associated. In one embodiment, said determining the level of expression of the protein to which the modification is associated and/or determining the frequency of the modified protein among the protein to which the modification is associated is performed on the RNA level. In one embodiment, the frequency of the modified protein among the protein to which the modification is associated is determined by determining the variant allele frequency. In one embodiment, the variant allele frequency is the sum of detected sequences, in particular reads, covering the mutation site and carrying the mutation divided by the sum of all detected sequences, in particular reads, covering the mutation site. In one embodiment, the variant allele frequency is the sum of mutated nucleotides at the mutation site divided by the sum of all nucleotides determined at the mutation site. In one embodiment, for ascertaining a score for expression or abundance of a modified protein a score for the level of expression of the protein to which the modification is associated is multiplied with a score for the frequency of the modified protein among the protein to which the modification is associated.

In one embodiment of all aspects of the invention, the modified peptide comprises a fragment of the modified protein, said fragment comprising the modification present in the protein.

In one embodiment of all aspects of the invention, the method further comprises identifying non-synonymous mutations in one or more protein-coding regions.

In one embodiment of all aspects of the invention, amino acid modifications are identified by partially or completely sequencing the genome or transcriptome of one or more cells such as one or more cancer cells and optionally one or more non-cancerous cells and identifying mutations in one or more protein-coding regions. In one embodiment, said mutations are somatic mutations. In one embodiment, said mutations are cancer mutations.

In one embodiment of all aspects of the invention, the method is used in the manufacture of a vaccine. In one embodiment, the vaccine is derived from (a) modification(s) or (a) modified peptide(s) predicted as immunogenic or more immunogenic by said method.

In one embodiment, in particular in order to provide a personalized vaccine for a patient such as a cancer patient, the modification(s) are present in said patient and said ascertaining a score for binding to one or more MHC class II molecules, and said ascertaining a score for expression or abundance of the modified protein is performed for said patient. Preferably, said one or more MHC class II molecules are present in said patient (in this embodiment the present invention may include determining the partial or complete MHC class II expression pattern of the patient). Preferably, said ascertaining a score for expression or abundance of the modified protein is performed on a sample from said patient such as a tumor specimen.

In a further aspect, the present invention relates to a method for providing a vaccine comprising the step:

identifying (a) modification(s) or (a) modified peptide(s) predicted as immunogenic or more immunogenic (than other modification(s) or modified peptide(s) also analysed) by the method of the invention. In one embodiment, the method further comprises the step:

providing a vaccine comprising a peptide or polypeptide comprising the modification(s) or modified peptide(s) predicted as immunogenic or more immunogenic, or a nucleic acid encoding the peptide or polypeptide.

In a further aspect, the present invention provides a vaccine which is obtainable using the methods according to the invention. Preferred embodiments of such vaccines are described herein.

A vaccine provided according to the invention may comprise a pharmaceutically acceptable carrier and may optionally comprise one or more adjuvants, stabilizers etc. The vaccine may in the form of a therapeutic or prophylactic vaccine.

Another aspect relates to a method for inducing an immune response in a patient, comprising administering to the patient a vaccine provided according to the invention.

Another aspect relates to a method of treating a cancer patient comprising the steps:

(a) providing a vaccine using the methods according to the invention; and (b) administering said vaccine to the patient.

Another aspect relates to a method of treating a cancer patient comprising administering the vaccine according to the invention to the patient.

In further aspects, the invention provides the vaccines described herein for use in the methods of treatment described herein, in particular for use in treating or preventing cancer.

The treatments of cancer described herein can be combined with surgical resection and/or radiation and/or traditional chemotherapy.

Other features and advantages of the instant invention will be apparent from the following detailed description and claims.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)". H. G. W. Leuenberger, B. Nagel, and H. Kölbl, Eds., (1995) *Helvetica ChimicaActa*, CH-4010 Basel, Switzerland.

The practice of the present invention will employ, unless otherwise indicated, conventional methods of biochemistry, cell biology, immunology, and recombinant DNA techniques which are explained in the literature in the field (cf., e.g., *Molecular Cloning: A Laboratory Manual, 2$^{nd}$ Edition*, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a staled member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

According to the present invention, the term "peptide" refers to substances comprising two or more, preferably 3 or more, preferably 4 or more, preferably 6 or more, preferably 8 or more, preferably 10 or more, preferably 13 or more, preferably 16 more, preferably 21 or more and up to preferably 8, 10, 20, 30, 40 or 50, in particular 100 amino acids joined covalently by peptide bonds. The term "polypeptide" or "protein" refers to large peptides, preferably to peptides with more titan 100 amino acid residues, but in general the terms "peptide", "polypeptide" and "protein" are synonyms and are used interchangeably herein.

According to the invention, the term "modification" with respect to peptides, polypeptides or proteins relates to a sequence change in a peptide, polypeptide or protein compared to a parental sequence such as the sequence of a wildtype peptide, polypeptide or protein. The term includes amino acid insertion variants, amino acid addition variants, amino acid deletion variants and amino acid substitution variants, preferably amino acid substitution variants. All these sequence changes according to the invention may potentially create new epitopes.

Amino acid insertion variants comprise insertions of single or two or more amino acids in a particular amino acid sequence.

Amino acid addition variants comprise amino- and/or carboxy-terminal fusions of one or more amino acids, such as 1, 2, 3, 4 or 5, or more amino acids.

Amino acid deletion variants are characterized by the removal of one or more amino acids from the sequence, such as by removal of 1, 2, 3, 4 or 5, or more amino acids.

Amino acid substitution variants are characterized by at least one residue in the sequence being removed and another residue being inserted in its place.

According to the invention, a modification or modified peptide used for testing in the methods of the invention may be derived from a protein comprising a modification.

The term "derived" means according to the invention that a particular entity, in particular a particular peptide sequence, is present in the object from which it is derived. In the case of amino acid sequences, especially particular sequence regions, "derived" in particular means that the relevant amino acid sequence is derived from an amino acid sequence in which it is present.

A protein comprising a modification from which a modification or modified peptide used for testing in the methods of the invention may be derived may be a neoantigen.

According to the invention, the term "neoantigen" relates to a peptide or protein including one or more amino acid modifications compared to the parental peptide or protein. For example, the neoantigen may be a tumor-associated neoantigen, wherein the term "tumor-associated neoantigen" includes a peptide or protein including amino acid modifications due to tumor-specific mutations.

According to the invention, the term "tumor-specific mutation" or "cancer-specific mutation" relates to a somatic mutation that is present in the nucleic acid of a tumor or cancer cell but absent in the nucleic acid of a corresponding normal, i.e. non-tumorous or non-cancerous, cell. The terms "tumor-specific mutation" and "tumor mutation" and the terms "cancer-specific mutation" and "cancer mutation" are used interchangeably herein.

The term "immune response" refers to an integrated bodily response to a target such as an antigen and preferably refers to a cellular immune response or a cellular as well as a humoral immune response. The immune response may be protective/preventive/prophylactic and/or therapeutic.

"Inducing an immune response" may mean that there was no immune response before induction, but it may also mean that there was a certain level of immune response before induction and after induction said immune response is enhanced. Thus, "inducing an immune response" also includes "enhancing an immune response". Preferably, after inducing an immune response in a subject, said subject is protected from developing a disease such as a cancer disease or the disease condition is ameliorated by inducing an immune response. For example, an immune response against a tumor-expressed antigen may be induced in a patient having a cancer disease or in a subject being at risk of developing a cancer disease. Inducing an immune response in this case may mean that the disease condition of the subject is ameliorated, that the subject does not develop metastases, or that the subject being at risk of developing a cancer disease does not develop a cancer disease.

The terms "cellular immune response" and "cellular response" or similar terms refer to an immune response directed to cells characterized by presentation of an antigen with class I or class II MHC involving T cells or T-lymphocytes which act as either "helpers" or "killers". The helper T cells (also termed $CD4^+$ T cells) play a central role by regulating the immune response and the killer cells (also termed cytotoxic T cells, cytolytic T cells, $CD8^+$ T cells or CTLs) kill diseased cells such as cancer cells, preventing the production of more diseased cells. In preferred embodiments, The present invention involves the stimulation of an anti-tumor CTL response against tumor cells expressing one or more tumor-expressed antigens and preferably presenting such tumor-expressed antigens with class I MHC.

An "antigen" according to the invention covers any substance, preferably a peptide or protein, that is a target of and/or induces an immune response such as a specific reaction with antibodies or T-lymphocytes (T cells). Preferably, an antigen comprises at least one epitope such as a T cell epitope. Preferably, an antigen in the context of the present invention is a molecule which, optionally after processing, induces an immune reaction, which is preferably specific for the antigen (including cells expressing the antigen). The antigen or a T cell epitope thereof is preferably presented by a cell, preferably by an antigen presenting cell which includes a diseased cell, in particular a cancer cell, in the context of MHC molecules, which results in an immune response against the antigen (including cells expressing the antigen).

In one embodiment, an antigen is a tumor antigen (also termed tumor-expressed antigen herein), i.e., a part of a tumor cell such as a protein or peptide expressed in a tumor cell which may be derived from the cytoplasm, the cell surface or the cell nucleus, in particular those which primarily occur intracellularly or as surface antigens of tumor cells. For example, tumor antigens include the carcinoembryonal antigen, $\alpha$1-fetoprotein, isoferritin, and fetal sulphoglycoprotein, $\alpha$2-H-ferroprotein and $\gamma$-fetoprotein. According to the present invention, a tumor antigen preferably comprises any antigen which is expressed in and optionally characteristic with respect to type and/or expression level for tumors or cancers as well as for tumor or cancer cells, i.e. a tumor-associated antigen. In one embodiment, the term "tumor-associated antigen" relates to proteins that are under normal conditions specifically expressed in a limited number of tissues and/or organs or in specific developmental stages, for example, the tumor-associated antigens may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2. The tumor antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. Preferably, the tumor antigen or the aberrant expression of the tumor antigen identifies cancer cells. In the context of the present invention, the tumor antigen that is expressed by a cancer cell in a subject, e.g., a patient suffering from a cancer disease, is preferably a self-protein in said subject. In preferred embodiments, the tumor antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system.

According to the invention, the terms "tumor antigen", "tumor-expressed antigen", "cancer antigen" and "cancer-expressed antigen" are equivalents and are used interchangeably herein.

The term "immunogenicity" relates to the relative effectivity to induce an immune response that is preferably associated with therapeutic treatments, such as treatments against cancers. As used herein, the term "immunogenic" relates to the property of having immunogenicity. For example, the term "immunogenic modification" when used in the context of a peptide, polypeptide or protein relates to the effectivity of said peptide, polypeptide or protein to induce an immune response that is caused by and/or directed against said modification. Preferably, the non-modified peptide, polypeptide or protein docs not induce an immune response, induces a different immune response or induces a different level, preferably a lower level, of immune response.

According to the invention, the term "immunogenicity" or "immunogenic" preferably relates to the relative effectively to induce a biologically relevant immune response, in particular an immune response which is useful for vaccination. Thus, in one preferred embodiment, an amino acid modification or modified peptide is immunogenic if it induces an immune response against the target modification in a subject, which immune response may be beneficial for therapeutic or prophylactic purposes.

The terms "major histocompatibility complex" and the abbreviation "MHC" include MHC class I and MHC class II molecules and relate to a complex of genes which occurs in all vertebrates. MHC proteins or molecules are important for signaling between lymphocytes and antigen presenting cells or diseased cells in immune reactions, wherein the MHC proteins or molecules bind peptides and present them for recognition by T cell receptors. The proteins encoded by the MHC are expressed on the surface of cells, and display both self antigens (peptide fragments from the cell itself) and non-self antigens (e.g., fragments of invading microorganisms) to a T cell.

The MHC region is divided into three subgroups, class I, class II, and class III. MHC class I proteins contain an $\alpha$-chain and $\beta$2-microglobulin (not part of the MHC encoded by chromosome 15). They present antigen fragments to cytotoxic T cells. On most immune system cells, specifically on antigen-presenting cells, MHC class II proteins contain $\alpha$- and $\beta$-chains and they present antigen fragments to T-helper cells. MHC class III region encodes for other immune components, such as complement components and some that encode cytokines.

The MHC is both polygenic (there are several MHC class I and MHC class II genes) and polymorphic (there are multiple alleles of each gene).

As used herein, the term "haplotype" refers to the HLA alleles found on one chromosome and the proteins encoded thereby. Haplotype may also refer to the allele present at any one locus within the MHC. Each class of MHC is represented by several loci: e.g., HLA-A (Human Leukocyte Antigen-A), HLA-B, HLA-C, HLA-E, HLA-F, HLA-G, HLA-H, HLA-J, HLA-K, HLA-L, HLA-P and HLA-V for class I and HLA-DRA, HLA-DRB1-9, HLA-, HLA-DQA1, HLA-DQB1, HLA-DPA1, HLA-DPB1, HLA-DMA, HLA-DMB, HLA-DOA, and HLA-DOB for class II. The terms "HLA allele" and "MHC allele" are used interchangeably herein.

The MHCs exhibit extreme polymorphism: within the human population there are, at each genetic locus, a great number of haplotypes comprising distinct alleles. Different polymorphic MHC alleles, of both class I and class II, have different peptide specificities: each allele encodes proteins that bind peptides exhibiting particular sequence patterns.

In one preferred embodiment of all aspects of the invention an MHC molecule is an HLA molecule.

According to the invention, MHC class II includes HLA-DM, HLA-DO, HLA-DP, HLA-DQ and HLA-DR.

In the context of the present invention, the term "MHC binding peptide" includes MHC class I and/or class II binding peptides or peptides that can be processed to produce MHC class I and/or class II binding peptides. In the case of class I MHC/peptide complexes, the binding peptides are typically 8-12, preferably 8-10 amino acids long although longer or shorter peptides may be effective. In the case of class II MHC/peptide complexes, the binding peptides are typically 9-30, preferably 10-25 amino acids long and are in particular 13-18 amino acids long, whereas longer and shorter peptides may be effective.

If a peptide is to be presented directly, i.e., without processing, in particular without cleavage, it has a length which is suitable for binding to an MHC molecule, in particular a class I MHC molecule, and preferably is 7-30 amino acids in length such as 7-20 amino acids in length, more preferably 7-12 amino acids in length, more preferably 8-11 amino acids in length, in particular 9 or 10 amino acids in length.

If a peptide is part of a larger entity comprising additional sequences, e.g. of a vaccine sequence or polypeptide, and is to be presented following processing, in particular following cleavage, the peptide produced by processing has a length which is suitable for binding to an MHC molecule, in particular a class I MHC molecule, and preferably is 7-30 amino acids in length such as 7-20 amino acids in length, more preferably 7-12 amino acids in length, more preferably 8-11 amino acids in length, in particular 9 or 10 amino acids in length. Preferably, the sequence of the peptide which is to be presented following processing is derived from the amino acid sequence of an antigen or polypeptide used for vaccination, i.e., its sequence substantially corresponds and is preferably completely identical to a fragment of the antigen or polypeptide.

Thus, an MHC binding peptide in one embodiment comprises a sequence which substantially corresponds and is preferably completely identical to a fragment of an antigen.

The term "epitope" refers to an antigenic determinant in a molecule such as an antigen, i.e., to a part in or fragment of the molecule that is recognized by the immune system, for example, that is recognized by a T cell, in particular when presented in the context of MHC molecules. An epitope of a protein such as a tumor antigen preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 9, 10, 11, 12, 13, 14, 15, 16, 17, 18, 19, 20, 21, 22, 23, 24, or 25 amino acids in length. It is particularly preferred that the epitope in the context of the present invention is a T cell epitope.

According to the invention an epitope may bind to MHC molecules such as MHC molecules on the surface of a cell and thus, may be a "MHC binding peptide".

As used herein the term "neo-epitope" refers to an epitope that is not present in a reference such as a normal non-cancerous or germline cell but is found in cancer cells. This includes, in particular, situations wherein in a normal non-cancerous or germline cell a corresponding epitope is found, however, due to one or more mutations in a cancer cell the sequence of the epitope is changed so as to result in the neo-epitope.

As used herein, the term "T cell epitope" refers to a peptide which binds to a MHC molecule in a configuration recognized by a T cell receptor. Typically, T cell epitopes are presented on the surface of an antigen-presenting cell.

As used herein, the term "predicting immunogenic amino acid modifications" refers to a prediction whether a peptide comprising such amino acid modification will be immunogenic and thus useful as epitope, in particular T cell epitope, in vaccination.

According to the invention, a T cell epitope may be present in a vaccine as a part of a larger entity such as a vaccine sequence and/or a polypeptide comprising more than one T cell epitope. The presented peptide or T cell epitope is produced following suitable processing.

T cell epitopes may be modified at one or more residues that are not essential for TCR recognition or for binding to MHC. Such modified T cell epitopes may be considered immunologically equivalent.

Preferably a T cell epitope when presented by MHC and recognized by a T cell receptor is able to induce in the presence of appropriate co-stimulatory signals, clonal expansion of the T cell carrying the T cell receptor specifically recognizing the peptide/MHC-complex.

Preferably, a T cell epitope comprises an amino acid sequence substantially corresponding to the amino acid sequence of a fragment of an antigen. Preferably, said fragment of an antigen is an MHC class I and/or class II presented peptide.

A T cell epitope according to the invention preferably relates to a portion or fragment of an antigen which is capable of stimulating an immune response, preferably a cellular response against the antigen or cells characterized by expression of the antigen and preferably by presentation of the antigen such as diseased cells, in particular cancer cells. Preferably, a T cell epitope is capable of stimulating a cellular response against a cell characterized by presentation of an antigen with class I MHC and preferably is capable of stimulating an antigen-responsive cytotoxic T-lymphocyte (CTL).

"Antigen processing" or "processing" refers to the degradation of a peptide, polypeptide or protein into procession products, which are fragments of said peptide, polypeptide or protein (e.g., the degradation of a polypeptide into peptides) and the association of one or more of these fragments (e.g., via binding) with MHC molecules for presentation by cells, preferably antigen presenting cells, to specific T cells.

"Antigen presenting cells" (APC) are cells which present peptide fragments of protein antigens in association with MHC molecules on their cell surface. Some APCs may activate antigen specific T cells.

Professional antigen-presenting cells are very efficient at internalizing antigen, either by phagocytosis or by receptor-mediated endocytosis, and then displaying a fragment of the antigen, bound to a class II MHC molecule, on their membrane. The T cell recognizes and interacts with the antigen-class II MHC molecule complex on the membrane of the antigen-presenting cell. An additional co-stimulatory signal is then produced by the antigen-presenting cell, leading to activation of the T cell. The expression of co-stimulatory molecules is a defining feature of professional antigen-presenting cells.

The main types of professional antigen-presenting cells are dendritic cells, which have the broadest range of antigen presentation, and are probably the most important antigen-presenting cells, macrophages, B-cells, and certain activated epithelial cells. Dendritic cells (DCs) are leukocyte populations that present antigens captured in peripheral tissues to T cells via both MHC class II and I antigen presentation pathways. It is well known that dendritic cells are potent inducers of immune responses and the activation of these cells is a critical step for the induction of antitumoral immunity. Dendritic cells are conveniently categorized as "immature" and "mature" cells, which can be used as a simple way to discriminate between two well characterized phenotypes. However, this nomenclature should not be construed to exclude all possible intermediate stages of differentiation. Immature dendritic cells are characterized as antigen presenting cells with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g. CD54 and CD11) and costimulatory molecules (e.g., CD40, CD80, CD86 and 4-1 BB). Dendritic cell maturation is referred to as the status of dendritic cell activation at which such antigen-presenting dendritic cells lead to T cell priming, while presentation by immature dendritic cells results in tolerance. Dendritic cell maturation is chiefly caused by biomolecules with microbial features detected by innate receptors (bacterial DNA, viral RNA, endotoxin, etc.), pro-inflammatory cytokines (TNF, IL-1, IFNs), ligation of CD40 on the dendritic cell surface by CD40L, and substances released from cells undergoing stressful cell death. The dendritic cells can be derived by culturing bone marrow cells in vitro with cytokines, such as granulocyte-macrophage colony-stimulating factor (GM-CSF) and tumor necrosis factor alpha.

Non-professional antigen-presenting cells do not constitutively express the MHC class II proteins required for interaction with naive T cells; these are expressed only upon stimulation of the non-professional antigen-presenting cells by certain cytokines such as IFNγ.

Antigen presenting cells can be loaded with MHC class I presented peptides by transducing the cells with nucleic acid, preferably RNA, encoding a peptide or polypeptide comprising the peptide to be presented, e.g. a nucleic acid encoding an antigen or polypeptide used for vaccination.

In some embodiments, a pharmaceutical composition or vaccine comprising a nucleic acid delivery vehicle that targets a dendritic or other antigen presenting cell may be administered to a patient, resulting in transfection that occurs in vivo. In vivo transfection of dendritic cells, for example, may generally be performed using any methods known in the art, such as those described in WO 97/24447, or the gene gun approach described by Mahvi et al., Immunology and cell Biology 75: 456-460, 1997.

According to the invention, the term "antigen presenting cell" also includes target cells.

"Target cell" shall mean a cell which is a target tor an immune response such as a cellular immune response. Target cells include cells that present an antigen, i.e. a peptide fragment derived from an antigen, and include any undesirable cell such as a cancer cell. In preferred embodiments, the target cell is a cell expressing an antigen as described herein and preferably presenting said antigen with class I MHC.

The term "portion" refers to a fraction. With respect to a particular structure such as an amino acid sequence or protein the term "portion" thereof may designate a continuous or a discontinuous fraction of said structure. Preferably, a portion of an amino acid sequence comprises at least 1%, at least 5%, at least 10%, at least 20%, at least 30%, preferably at least 40%, preferably at least 50%, more preferably at least 60%, more preferably at least 70%, even more preferably at least 80%, and most preferably at least 90% of the amino acids of said amino acid sequence. Preferably, if the portion is a discontinuous fraction said discontinuous fraction is composed of 2, 3, 4, 5, 6, 7, 8, or more parts of a structure, each part being a continuous element of the structure. For example, a discontinuous fraction of an amino acid sequence may be composed of 2, 3, 4, 5, 6, 7, 8, or more, preferably not more than 4 parts of said amino acid sequence, wherein each part preferably comprises at least 5 continuous amino acids, at least 10 continuous amino acids, preferably at least 20 continuous amino acids, preferably at least 30 continuous amino acids of the amino acid sequence.

The terms "part" and "fragment" are used interchangeably herein and refer to a continuous element. For example, a part of a structure such as an amino acid sequence or protein refers to a continuous element of said structure. A portion, a part or a fragment of a structure preferably comprises one or more functional properties of said structure. For example, a portion, a part or a fragment of an epitope, peptide or protein is preferably immunologically equivalent to the epitope, peptide or protein it is derived from. In the context of the present invention, a "part" of a structure such as an amino acid sequence preferably comprises, preferably consists of at least 10%, at least 20%, at least 30%, at least 40%, at least 50%, at least 60%, at least 70%, at least 80%, at least 85%, at least 90%, at least 92%, at least 94%, at least 96%, at least 98%, at least 99% of the entire structure or amino acid sequence.

The term "immunoreactive cell" in the context of the present invention relates to a cell which exerts effector functions during an immune reaction. An "immunoreactive cell" preferably is capable of binding an antigen or a cell characterized by presentation of an antigen or a peptide fragment thereof (e.g. a T cell epitope) and mediating an immune response. For example, such cells secrete cytokines and/or chemokines, secrete antibodies, recognize cancerous cells, and optionally eliminate such cells. For example, immunoreactive cells comprise T cells (cytotoxic T cells, helper T cells, tumor infiltrating T cells), B cells, natural killer cells, neutrophils, macrophages, and dendritic cells. Preferably, in the context of the present invention, "immunoreactive cells" are T cells, preferably $CD4^+$ and/or $CD8^+$ T cells.

Preferably, an "immunoreactive cell" recognizes an antigen or a peptide fragment thereof with some degree of specificity, in particular if presented in the context of MHC molecules such as on the surface of antigen presenting cells or diseased cells such as cancer cells. Preferably, said recognition enables the cell that recognizes an antigen or a peptide fragment thereof to be responsive or reactive. If the cell is a helper T cell (CD4+ T cell) bearing receptors that recognize an antigen or a peptide fragment thereof in the context of MHC class II molecules such responsiveness or reactivity may involve the release of cytokines and/or the activation of CD8+ lymphocytes (CTLs) and/or B-cells. If the cell is a CTL such responsiveness or reactivity may involve the elimination of cells presented in the context of MHC class I molecules, i.e., cells characterized by presentation of an antigen with class I MHC, for example, via apoptosis or perform-mediated cell lysis. According to the invention, CTL responsiveness may include sustained calcium flux, cell division, production of cytokines such as IFN-γ and TNF-α, up-regulation of activation markers such as CD44 and CD69, and specific cytolytic killing of antigen expressing target cells. CTL responsiveness may also be determined using an artificial reporter that accurately indicates CTL responsiveness. Such CTL that recognize an antigen or an antigen fragment and are responsive or reactive are also termed "antigen-responsive CTL" herein. If the cell is a B cell such responsiveness may involve the release of immunoglobulins.

The terms "T cell" and "T lymphocyte" are used interchangeably herein and include T helper cells (CD4+ T cells) and cytotoxic T cells (CTLs, CD8+ T cells) which comprise cytolytic T cells.

T cells belong to a group of white blood cells known as lymphocytes, and play a central role in cell-mediated immunity. They can be distinguished from other lymphocyte types, such as B cells and natural killer cells by the presence of a special receptor on their cell surface called T cell receptor (TCR). The thymus is the principal organ responsible for the maturation of T cells. Several different subsets of T cells have been discovered, each with a distinct function.

T helper cells assist other white blood cells in immunologic processes, including maturation of B cells into plasma cells and activation of cytotoxic T cells and macrophages, among other functions. These cells are also known as CD4+ T cells because they express the CD4 protein on their surface. Helper T cells become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T cells destroy virally infected cells and tumor cells, and are also implicated in transplant rejection. These cells are also known as CD8+ T cells since they express the CD8 glycoprotein at their surface. These cells recognize their targets by binding to antigen associated with MHC class I, which is present on the surface of nearly every cell of the body.

A majority of T cells have a T cell receptor (TCR) existing as a complex of several proteins. The actual T cell receptor is composed of two separate peptide chains, which are produced from the independent T cell receptor alpha and beta (TCRα and TCRβ) genes and are called α- and β-TCR chains. γδ T cells (gamma delta T cells) represent a small subset of T cells that possess a distinct T cell receptor (TCR) on their surface. However, in γδ T cells, the TCR is made up of one γ-chain and one δ-chain. This group of T cells is much less common (2% of total T cells) than the αβ T cells.

The first signal in activation of T cells is provided by binding of the T cell receptor in a short peptide presented by the MHC on another cell. This ensures that only a T cell with a TCR specific to that peptide is activated. The partner cell is usually an antigen presenting cell such as a professional antigen presenting cell, usually a dendritic cell in the case of naïve responses, although B cells and macrophages can be important APCs.

According to the present invention, a molecule is capable of binding to a target if it has a significant affinity for said predetermined target and binds to said predetermined target in standard assays. "Affinity" or "binding affinity" is often measured by equilibrium dissociation constant ($K_D$). A molecule is not (substantially) capable of binding to a target if it has no significant affinity for said target and does not bind significantly to said target in standard assays.

Cytotoxic T lymphocytes may be generated in vivo by incorporation of an antigen or a peptide fragment thereof into antigen-presenting cells in vivo. The antigen or a peptide fragment thereof may be represented as protein, as DNA (e.g. within a vector) or as RNA. The antigen may be processed to produce a peptide partner for the MHC molecule, while a fragment thereof may be presented without the need for further processing. The latter is the case in particular, if these can bind to MHC molecules. In general, administration to a patient by intradermal injection is possible. However, injection may also be carried out intranodally into a lymph node (Maloy et al. (2001), Proc Natl Acad Sci USA 98:3299-303). The resulting cells present the complex of interest and are recognized by autologous cytotoxic T lymphocytes which then propagate.

Specific activation of CD4+ or CD8+ T cells may be detected in a variety of ways. Methods for detecting specific T cell activation include detecting the proliferation of T cells, the production of cytokines (e.g., lymphokines), or the generation of cytolytic activity. For CD4+ T cells, a preferred method for detecting specific T cell activation is the detection of the proliferation of T cells. For CD8+ T cells, a preferred method for detecting specific T cell activation is the detection of the generation of cytolytic activity.

By "cell characterized by presentation of an antigen" or "cell presenting an antigen" or similar expressions is meant a cell such as a diseased cell, e.g. a cancer cell, or an antigen presenting cell presenting the antigen it expresses or a fragment derived from said antigen, e.g. by processing of the antigen, in the context of MHC molecules, in particular MHC Class I molecules. Similarly, the terms "disease characterized by presentation of an antigen" denotes a disease involving cells characterized by presentation of an antigen, in particular with class I MHC. Presentation of an antigen by a cell may be effected by transfecting the cell with a nucleic acid such as RNA encoding the antigen.

By "fragment of an antigen which is presented" or similar expressions is meant that the fragment can be presented by MHC class I or class II, preferably MHC class I, e.g. when added directly to antigen presenting cells. In one embodiment, the fragment is a fragment which is naturally presented by cells expressing an antigen.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect such as induction of a humoral and/or cellular immune response, the strength and/or duration of the induced immune reaction, or the specificity of the induced immune reaction. In the context of the present invention, the term "immunologically equivalent" is preferably used with respect to the immunological effects or properties of a peptide used for immunization. For example, an amino acid sequence is immunologically equivalent to a reference amino acid sequence if said amino acid sequence when exposed to the immune system of a subject induces an immune reaction having a specificity of reacting with the reference amino acid sequence.

The term "immune effector functions" in the context of the present invention includes any functions mediated by components of the immune system that result, for example, in the killing of tumor cells, or in the inhibition of tumor growth and/or inhibition of tumor development, including inhibition of tumor dissemination and metastasis. Preferably, the immune effector functions in the context of the present invention are T cell mediated effector functions. Such functions comprise in the case of a helper T cell (CD4+ T cell) the recognition of an antigen or an antigen fragment in the context of MHC class II molecules by T cell receptors, the release of cytokines and/or the activation of $CD8^+$ lymphocytes (CTLs) and/or B-cells, and in the case of CTL the recognition of an antigen or an antigen fragment in the context of MHC class I molecules by T cell receptors, the elimination of cells presented in the context of MHC class I molecules, i.e., cells characterized by presentation of an antigen with class I MHC, for example, via apoptosis or perform-mediated cell lysis, production of cytokines such as IFN-γ and TNF-α, and specific cytolytic killing of antigen expressing target cells.

According to the invention, the term "score" relates to a result, usually expressed numerically, of a test or examination. Terms such as "score better" or "score best" relate to a better result or the best result of a test or examination.

According to the invention, modified peptides are scored according to their predicted ability to bind to MHC class II and according to the expression or abundance of the modified proteins from which the modified peptides are derived. In general, a peptide with a predicted higher ability to bind to MHC class II is scored better than a peptide with a predicted lower ability to bind to MHC class II. Furthermore, a peptide with higher expression or abundance of the corresponding modified protein is scored better than a peptide with lower expression or abundance of the corresponding modified protein.

Terms such as "predict", "predicting" or "prediction" relate to the determination of a likelihood.

According to the invention, ascertaining a score for binding of a peptide to one or more MHC class II molecules includes determining the likelihood of binding of a peptide to one or more MHC class II molecules.

A score for binding of a peptide to one or more MHC class II molecules may be ascertained by using any peptide: MHC binding predictive tools. For example, the immune epitope database analysis resource (IEDB-AR: http://tools.iedb.org) may be used.

Predictions are usually made against a set of MHC class II molecules such as a set of different MHC class II alleles such as all possible MHC class II alleles or a set or subset of MHC class II alleles found in a patient. Preferably, the patient has the modification(s) the immunogenicity of which is to be determined according to the invention or which are to be selected and/or ranked according to their predicted immunogenicity according to the invention. Preferably, the vaccine described herein is to be provided ultimately for said patient. Accordingly, the present invention may also include determining the MHC class II expression pattern of a patient.

The present invention also may comprise performing the method of the invention on different peptides comprising the same modification(s) and/or different modifications.

The term "different peptides comprising the same modification(s)" in one embodiment relates to peptides comprising or consisting of different fragments of a modified protein, said different fragments comprising the same modification(s) present in the protein but differing in length and/or position of the modification(s). If a protein has a modification at position x, two or more fragments of said protein each comprising a different sequence window of said protein covering said position x are considered different peptides comprising the same modification(s).

The term "different peptides comprising different modifications" in one embodiment relates to peptides either of the same and/or differing lengths comprising different modifications of either of the same and/or different proteins. If a protein has modifications at positions x and y, two fragments of said protein each comprising a sequence window of said protein covering either position x or position y are considered different peptides comprising different modifications.

The present invention also may comprise breaking of protein sequences having modifications the immunogenicity of which is to be determined according to the invention or which are to be selected and/or ranked according to their predicted immunogenicity according to the invention into appropriate peptide lengths for MHC binding and ascertaining scores for binding to one or more MHC class II molecules of different modified peptides comprising the same and/or different modifications of either the same and/or different proteins. Outputs may be ranked and may consist of a list of peptides and their predicted scores, indicating their likelihood of binding.

The step of ascertaining a score for expression or abundance of the modified protein may be performed with all different modifications, a subset thereof, e.g. those modifications scoring best for binding to one or more MHC class II molecules, or only with the modification scoring best for binding to one or more MHC class II molecules.

Following said further step, the results may be ranked and may consist of a list of peptides and their predicted scores, indicating their likelihood of being immunogenic.

According to the invention, ascertaining a score for expression or abundance of the modified protein may be performed for a patient such as a cancer patient, for example, on a tumor specimen of a patient such as a cancer patient.

According to the invention, ascertaining a score for expression or abundance of a modified protein may comprises determining the level of expression of the protein to which the modification is associated and/or determining the level of expression of RNA encoding the protein to which the modification is associated (which again may be indicative for the level of expression of the protein to which the modification is associated) and determining the frequency of the modified protein among the protein to which the modification is associated and/or determining the frequency of RNA encoding the modified protein among the RNA encoding the protein to which the modification is associated.

The frequency of the modified protein among the protein to which the modification is associated and/or the frequency of RNA encoding the modified protein among the RNA encoding the protein to which the modification is associated may be considered the proportion of the modified protein within the protein to which the modification is associated and/or the proportion of RNA encoding the modified protein within the RNA encoding the protein to which the modification is associated.

According to the invention, the term "protein to which the modification is associated" relates to the protein which may comprise the modification and includes the protein in its unmodified as well as modified state.

According to the invention, the term "level of expression" may refer to an absolute or relative amount.

The amino acid modifications the immunogenicity of which is to be determined according to the present invention or which are to be selected and/or ranked according to their predicted immunogenicity according to the invention may result from mutations in the nucleic acid of a cell. Such mutations may be identified by known sequencing techniques.

In one embodiment, the mutations are cancer specific somatic mutations in a tumor specimen of a cancer patient which may be determined by identifying sequence differences between the genome, exome and/or transcriptome of a tumor specimen and the genome, exome and/or transcriptome of a non-tumorigenous specimen.

According to the invention a tumor specimen relates to any sample such as a bodily sample derived from a patient containing or being expected of containing tumor or cancer cells. The bodily sample may be any tissue sample such as blood, a tissue sample obtained from the primary tumor or from tumor metastases or any other sample containing tumor or cancer cells. Preferably, a bodily sample is blood and cancer specific somatic mutations or sequence differences are determined in one or more circulating tumor cells (CTCs) contained in the blood. In another embodiment, a tumor specimen relates to one or more isolated tumor or cancer cells such as circulating tumor cells (CTCs) or a sample containing one or more isolated tumor or cancer cells such as circulating tumor cells (CTCs).

A non-tumorigenous specimen relates to any sample such as a bodily sample derived from a patient or another individual which preferably is of the same species as the patient, preferably a healthy individual not containing or not being expected of containing tumor or cancer cells. The bodily sample may be any tissue sample such as blood or a sample from a non-tumorigenous tissue.

The invention may involve the determination of the cancer mutation signature of a patient. The term "cancer mutation signature" may refer to all cancer mutations present in one or more cancer cells of a patient or it may refer to only a portion of the cancer mutations present in one or more cancer cells of a patient. Accordingly, the present invention may involve the identification of all cancer specific mutations present in one or more cancer cells of a patient or it may involve the identification of only a portion of the cancer specific mutations present in one or more cancer cells of a patient. Generally, the methods of the invention provides for the identification of a number of mutations which provides a sufficient number of modifications or modified peptides to be included in the methods of the invention.

Preferably, the mutations identified according to the present invention are non-synonymous mutations, preferably non-synonymous mutations of proteins expressed in a tumor or cancer cell.

In one embodiment, cancer specific somatic mutations or sequence differences are determined in the genome, preferably the entire genome, of a tumor specimen. Thus, the invention may comprise identifying the cancer mutation signature of the genome, preferably the entire genome of one or more cancer cells. In one embodiment, the step of identifying cancer specific somatic mutations in a tumor specimen of a cancer patient comprises identifying the genome-wide cancer mutation profile.

In one embodiment, cancer specific somatic mutations or sequence differences are determined in the exome, preferably the entire exome, of a tumor specimen. Thus, the invention may comprise identifying the cancer mutation signature of the exome, preferably the entire exome of one or more cancer cells. In one embodiment, the step of identifying cancer specific somatic mutations in a tumor specimen of a cancer patient comprises identifying the exome-wide cancer mutation profile.

In one embodiment, cancer specific somatic mutations or sequence differences are determined in the transcriptome, preferably the entire transcriptome, of a tumor specimen. Thus, the invention may comprise identifying the cancer mutation signature of the transcriptome, preferably the entire transcriptome of one or more cancer cells. In one embodiment, the step of identifying cancer specific somatic mutations in a tumor specimen of a cancer patient comprises identifying the transcriptome-wide cancer mutation profile.

In one embodiment, the step of identifying cancer specific somatic mutations or identifying sequence differences comprises single cell sequencing of one or more, preferably 2, 3, 4, 5, 6, 7, 8, 9, 10, 11, 12, 13, 14, 15, 16, 17, 18, 19, 20 or even more cancer cells. Thus, the invention may comprise identifying a cancer mutation signature of said one or more cancer cells. In one embodiment, the cancer cells are circulating tumor cells. The cancer cells such as the circulating tumor cells may be isolated prior to single cell sequencing.

In one embodiment, the step of identifying cancer specific somatic mutations or identifying sequence differences involves using next generation sequencing (NGS).

In one embodiment, the step of identifying cancer specific somatic mutations or identifying sequence differences comprises sequencing genomic DNA and/or RNA of the tumor specimen.

To reveal cancer specific somatic mutations or sequence differences the sequence information obtained from the tumor specimen is preferably compared with a reference such as sequence information obtained from sequencing nucleic acid such as DNA or RNA of normal non-cancerous cells such as germline cells which may either be obtained from the patient or a different individual. In one embodiment, normal genomic germline DNA is obtained from peripheral blood mononuclear cells (PBMCs)

The term "genome" relates to the total amount of genetic information in the chromosomes of an organism or a cell.

The term "exome" refers to part of the genome of an organism formed by exons, which are coding portions of expressed genes. The exome provides the genetic blueprint used in the synthesis of proteins and other functional gene products. It is the most functionally relevant part of the genome and, therefore, it is most likely to contribute to the phenotype of an organism. The exome of the human genome is estimated to comprise 1.5% of the total genome (Ng, P C et al., PLoS Gen., 4(8): 1-15, 2008).

The term "transcriptome" relates to the set of all RNA molecules, including mRNA, rRNA, tRNA, and other non-coding RNA produced in one cell or a population of cells. In context of the present invention the transcriptome means the set of all RNA molecules produced in one cell, a population of cells, preferably a population of cancer cells, or all cells of a given individual at a certain time point.

A "nucleic acid" is according to the invention preferably deoxyribonucleic acid (DNA) or ribonucleic acid (RNA), more preferably RNA, most preferably in vitro transcribed RNA (IVT RNA) or synthetic RNA. Nucleic acids include according to the invention genomic DNA, cDNA, mRNA, recombinantly produced and chemically synthesized molecules. According to the invention, a nucleic acid may be present as a single-stranded or double-stranded and linear or covalently circularly closed molecule. A nucleic acid can, according to the invention, be isolated. The term "isolated nucleic acid" means, according to the invention, that the nucleic acid (i) was amplified in vitro, for example via polymerase chain reaction (PCR), (ii) was produced recombinantly by cloning, (iii) was purified, for example, by cleavage and separation by gel electrophoresis, or (iv) was synthesized, for example, by chemical synthesis. A nucleic can be employed for introduction into, i.e. transfection of, cells, in particular, in the form of RNA which can be prepared by in vitro transcription from a DNA template. The RNA can moreover be modified before application by stabilizing sequences, capping, and polyadenylation.

The term "genetic material" refers to isolated nucleic acid, either DNA or RNA, a section of a double helix, a section of a chromosome, or an organism's or cell's entire genome, in particular its exome or transcriptome.

The term "mutation" refers to a change of or difference in the nucleic acid sequence (nucleotide substitution, addition or deletion) compared to a reference. A "somatic mutation" can occur in any of the cells of the body except the germ cells (sperm and egg) and therefore are not passed on to children. These alterations can (but do not always) cause cancer or other diseases.

Preferably a mutation is a non-synonymous mutation. The term "non-synonymous mutation" refers to a mutation, preferably a nucleotide substitution, which does result in an amino acid change such as an amino acid substitution in the translation product.

According to the invention, the term "mutation" includes point mutations, Indels, fusions, chromothripsis and RNA edits.

According to the invention, the term "Indel" describes a special mutation class, defined as a mutation resulting in a colocalized insertion and deletion and a net gain or loss in nucleotides. In coding regions of the genome, unless the length of an indel is a multiple of 3, they produce a frameshift mutation. Indels can be contrasted with a point mutation; where an Indel inserts and deletes nucleotides from a sequence, a point mutation is a form of substitution that replaces one of the nucleotides.

Fusions can generate hybrid genes formed from two previously separate genes. It can occur as the result of a translocation, interstitial deletion, or chromosomal inversion. Often, fusion genes are oncogenes. Oncogenic fusion genes may lead to a gene product with a new or different function from the two fusion partners. Alternatively, a proto-oncogene is fused to a strong promoter, and thereby the oncogenic function is set to function by an upregulation caused by the strong promoter of the upstream fusion partner. Oncogenic fusion transcripts may also be caused by trans-splicing or read-through events.

According to the invention, the term "chromothripsis" refers to a genetic phenomenon by which specific regions of the genome are shattered and then stitched together via a single devastating event.

According to the invention, the term "RNA edit" or "RNA editing" refers to molecular processes in which the information content in an RNA molecule is altered through a chemical change in the base makeup. RNA editing includes nucleoside modifications such as cytidine (C) to uridine (U) and adenosine (A) to inosine (I) deaminations, as well as non-templated nucleotide additions and insertions. RNA editing in mRNAs effectively alters the amino acid sequence of the encoded protein so that it differs from that predicted by the genomic DNA sequence.

The term "cancer mutation signature" refers to a set of mutations which are present in cancer cells when compared to non-cancerous reference cells.

According to the invention, a "reference" may be used to correlate and compare the results obtained in the methods of the invention from a tumor specimen. Typically the "reference" may be obtained on the basis of one or more normal specimens, in particular specimens which are not affected by a cancer disease, either obtained from a patient or one or more different individuals, preferably healthy individuals, in particular individuals of the same species. A "reference" can be determined empirically by testing a sufficiently large number of normal specimens.

Any suitable sequencing method can be used according to the invention for determining mutations, Next Generation Sequencing (NGS) technologies being preferred. Third Generation Sequencing methods might substitute for the NGS technology in the future to speed up the sequencing step of the method. For clarification purposes: the terms "Next Generation Sequencing" or "NGS" in the context of the present invention mean all novel high throughput sequencing technologies which, in contrast to the "conventional" sequencing methodology known as Sanger chemistry, read nucleic acid templates randomly in parallel along the entire genome by breaking the entire genome into small pieces. Such NGS technologies (also known as massively parallel sequencing technologies) are able to deliver nucleic acid sequence information of a whole genome, exome, transcriptome (all transcribed sequences of a genome) or methylome (all methylated sequences of a genome) in very short time periods, e.g. within 1-2 weeks, preferably within 1-7 days or most preferably within less than 24 hours and allow, in principle, single cell sequencing approaches. Multiple NGS platforms which are commercially available or which are mentioned in the literature can be used in the context of the present invention e.g. those described in detail in Zhang el at. 2011: *The impact of next-generation sequencing on genomics. J. Genet Genomics* 38 (3), 95-109; or in Voelkerding et al. 2009: *Next generation sequencing: From basic research to diagnostics. Clinical chemistry* 55, 641-658. Non-limiting examples of such NGS technologies/platforms are 1) The sequencing-by-synthesis technology known as pyrosequencing implemented e.g. in the GS-FLX 454 Genome Sequencer™ of Roche-associated company 454 Life Sciences (Branford, Conn.), first described in Ronaghi et al. 1998: *A sequencing method bused on real-time pyrophosphate"*. *Science* 281 (5375), 363-365. This technology uses an emulsion PCR in which single-stranded DNA binding beads are encapsulated by vigorous vortexing into aqueous micelles containing PCR reactants surrounded by oil for emulsion PCR amplification. During the pyrosequencing process, light emitted from phosphate molecules during nucleotide incorporation is recorded as the polymerase synthesizes the DNA strand.

2) The sequencing-by-synthesis approaches developed by Solexa (now part of Illumina Inc., San Diego, Calif.) which is based on reversible dye-terminators and implemented e.g. in the Illumina/Solexa Genome Analyzer™ and in the Illumina HiSeq 2000 Genome Analyzer™. In this technology, all four nucleotides are added simultaneously into oligo-primed cluster fragments in flow-cell channels along with DNA polymerase. Bridge amplification extends cluster strands with all four fluorescently labeled nucleotides for sequencing.

3) Sequencing-by-ligation approaches, e.g. implemented in the SOLid™ platform of Applied Biosystems (now Life Technologies Corporation, Carlsbad, Calif.). In this technology, a pool of all possible oligonucleotides of a fixed length are labeled according to the sequenced position. Oligonucleotides are annealed and ligated; the preferential ligation by DNA ligase for matching sequences results in a signal informative of the nucleotide at that position. Before sequencing, the DNA is amplified by emulsion PCR. The resulting bead, each containing only copies of the same DNA molecule, are deposited on a glass slide. As a second example, he Polonator™ G.007 platform of Dover Systems (Salem, N.H.) also employs a sequencing-by-ligation approach by using a randomly arrayed, bead-based, emulsion PCR to amplify DNA fragments for parallel sequencing.

4) Single-molecule sequencing technologies such as e.g. implemented in the PacBio RS system of Pacific Biosciences (Menlo Park, Calif.) or in the HeliScope™ platform of Helicos Biosciences (Cambridge, Mass.). The distinct characteristic of this technology is its ability to sequence single DNA or RNA molecules without amplification, defined as Single-Molecule Real Time (SMRT) DNA sequencing. For example, HeliScope uses a highly sensitive fluorescence detection system to directly detect each nucleotide as it is synthesized. A similar approach based on fluorescence resonance energy transfer (FRET) has been developed from Visigen Biotechnology (Houston, Tex.). Other fluorescence-based single-molecule techniques are from U.S. Genomics (GeneEngine™) and Genovoxx (AnyGene™).

5) Nano-technologies for single-molecule sequencing in which various nanostructures are used which are e.g. arranged on a chip to monitor the movement of a polymerase molecule on a single strand during replication. Non-limiting examples for approaches based on nano-technologies are the GridON™ platform of Oxford Nanopore Technologies (Oxford, UK), the hybridization-assisted nano-pore sequencing (HANS™) platforms developed by Nabsys (Providence, R.I.), and the proprietary ligase-based DNA sequencing platform with DNA nanoball (DNB) technology called combinatorial probe-anchor ligation (cPAL™).

6) Electron microscopy based technologies for single-molecule sequencing, e.g. those developed by Light-Speed Genomics (Sunnyvale, Calif.) and Haleyon Molecular (Redwood City, Calif.)

7) Ion semiconductor sequencing which is based on the detection of hydrogen ions that are released during the polymerisation of DNA. For example, Ion Torrent Systems (San Francisco, Calif.) uses a high-density array of micro-machined wells to perform this biochemical process in a massively parallel way. Each well holds a different UNA template. Beneath the wells is an ion-sensitive layer and beneath that a proprietary Ion sensor.

Preferably, DNA and RNA preparations serve as starting material for NGS. Such nucleic acids can be easily obtained from samples such as biological material, e.g. from fresh, flash-frozen or formalin-fixed paraffin embedded tumor tissues (FFPE) or from freshly isolated cells or from CTCs which are present in the peripheral blood of patients. Normal non-mutated genomic DNA or RNA can be extracted from normal, somatic tissue, however germline cells are preferred in the context of the present invention. Germline DNA or RNA may be extracted from peripheral blood mononuclear cells (PBMCs) in patients with non-hematological malignancies. Although nucleic acids extruded from FFPE tissues or freshly isolated single cells are highly fragmented, they are suitable for NGS applications.

Several targeted NGS methods for exome sequencing are described in the literature (for review see e.g. Teer and Mullikin 2010: *Human Mol Genet* 19 (2), R145-51), all of which can be used in conjunction with the present invention. Many of these methods (described e.g. as genome capture, genome partitioning, genome enrichment etc.) use hybridization techniques and include array-based (e.g. Hodges et al. 2007: *Nat. Genet.* 39, 1522-1527) and liquid-based (e.g. Choi el al. 2009: *Proc. Natl. Acad. Sci USA* 106, 19096-19101) hybridization approaches. Commercial kits for DNA sample preparation and subsequent exome capture are also available: for example, Illumina Inc. (San Diego, Calif.) offers the TruSeq™ DNA Sample Preparation Kit and the Exome Enrichment Kit TruSeq™ Exome Enrichment Kit.

In order to reduce the number of false positive findings in detecting cancer specific somatic mutations or sequence differences when comparing e.g. the sequence of a tumor sample to the sequence of a reference sample such as the sequence of a germ line sample it is preferred to determine the sequence in replicates of one or both of these sample types. Thus, it is preferred that the sequence of a reference sample such as the sequence of a germ line sample is determined twice, three times or more. Alternatively or additionally, the sequence of a tumor sample is determined twice, three times or more. It may also be possible to determine the sequence of a reference sample such as the sequence of a germ line sample and/or the sequence of a tumor sample more than once by determining at least once the sequence in genomic DNA and determining at least once the sequence in RNA of said reference sample and/or of said tumor sample. For example, by determining the variations between replicates of a reference sample such as a germ line sample the expected rate of false positive (FDR) somatic mutations as a statistical quantity can be estimated. Technical repeats of a sample should generate identical results and any detected mutation in this "same vs. same comparison" is a false positive. In particular, to determine the false discovery rate for somatic mutation detection in a tumor sample relative to a reference sample, a technical repeat of the reference sample can be used as a reference to estimate the number of false positives. Furthermore, various quality related metrics (e.g. coverage or SNP quality) may be combined into a single quality score using a machine learning approach. For a given somatic variation all other variations with an exceeding quality score may be counted, which enables a ranking of all variations in a dataset.

In the context of the present invention, the term "RNA" relates to a molecule which comprises at least one ribonucleotide residue and preferably being entirely or substantially composed of ribonucleotide residues. "Ribonucleotide" relates to a nucleotide with a hydroxyl group at the 2'-position of a β-D-ribofuranosyl group. The term "RNA" comprises double-stranded RNA, single-stranded RNA, isolated RNA such as partially or completely purified RNA, essentially pure RNA, synthetic RNA, and recombinantly generated RNA such as modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the present invention, the term "RNA" includes and preferably relates to "mRNA". The term "mRNA" means "messenger-RNA" and relates to a "transcript" which is generated by using a DNA template and encodes a peptide or polypeptide. Typically, an mRNA comprises a 5'-UTR, a protein coding region, and a 3'-UTR, mRNA only possesses limited half-life in cells and in vitro. In the context of the present invention, mRNA may be generated by in vitro transcription from a DNA template. The in vitro transcription methodology is known to the skilled person. For example, there is a variety of in vitro transcription kits commercially available.

According to the invention, the stability and translation efficiency of RNA may be modified as required. For example, RNA may be stabilized and its translation increased by one or more modifications having a stabilizing effects and/or increasing translation efficiency of RNA. Such modifications are described, for example, in PCT/EP2006/009448 incorporated herein by reference. In order to increase expression of the RNA used according to the present invention, it may be modified within the coding region, i.e. the sequence encoding the expressed peptide or protein, preferably without altering the sequence of the expressed peptide or protein, so as to increase the GC-content to increase mRNA stability and to perform a codon optimization and, thus, enhance translation in cells.

The term "modification" in the context of the RNA used in the present invention includes any modification of an RNA which is not naturally present in said RNA.

In one embodiment of the invention, the RNA used according to the invention does not have uncapped 5'-triposphates. Removal of such uncapped 5'-triphosphates can be achieved by treating RNA with a phosphatase.

The RNA according to the invention may have modified ribonucleotides in order to increase its stability and/or decrease cytotoxicity. For example, in one embodiment, in the RNA used according to the invention 5-methylcylidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap ($m^7G$). In the context of the present invention, the term "5'-cap" includes a 5'-cap analog that resembles the RNA cap structure and is modified to possess the ability to stabilize RNA and/or enhance translation of RNA if attached thereto, preferably in vivo and/or in a cell.

Providing an RNA with a 5'-cap or 5'-cap analog may be achieved by in vitro transcription of a DNA template in presence of said 5'-cap or 5'-cap analog, wherein said 5-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus.

The RNA may comprise further modifications. For example, a further modification of the RNA used in the present invention may be an extension or truncation of the naturally occurring poly(A) tail or an alteration of the 5'- or 3'-untranslated regions (UTR) such as introduction of a UTR which is not related to the coding region of said RNA, for example, the exchange of the existing 3'-UTR with or the insertion of one or more, preferably two copies of a 3'-UTR derived from a globin gene, such as alpha2-globin, alpha1-globin, beta-globin, preferably beta-globin, more preferably human beta-globin.

RNA having an unmasked poly-A sequence is translated more efficiently than RNA having a masked poly-A sequence. The term "poly(A) tail" or "poly-A sequence" relates to a sequence of adenyl (A) residues which typically is located on the 3'-end of a RNA molecule and "unmasked poly-A sequence" means that the poly-A sequence at the 3' end of an RNA molecule ends with an A of the poly-A sequence and is not followed by nucleotides other than A located at the 3' end i.e. downstream, of the poly-A sequence. Furthermore, a long poly-A sequence of about 120 base pairs results in an optimal transcript stability and translation efficiency of RNA.

Therefore, in order to increase stability and/or expression of the RNA used according to the present invention, it may be modified so as to be present in conjunction with a poly-A sequence, preferably having a length of 10 to 500, more preferably 30 to 300, even more preferably 65 to 200 and especially 100 to 150 adenosine residues. In an especially preferred embodiment the poly-A sequence has a length of approximately 120 adenosine residues. To further increase stability and/or expression of the RNA used according to the invention, the poly-A sequence can be unmasked.

In addition, incorporation of a 3'-non translated region (UTR) into the 3'-non translated region of an RNA molecule can result in an enhancement in translation efficiency. A synergistic effect may be achieved by incorporating two or more of such 3'-non translated regions. The 3'-non translated regions may be autologous or heterologous to the RNA into which they are introduced.

In line particular embodiment the 3'-non translated region is derived from the human β-globin gene.

A combination of the above described modifications, i.e. incorporation of a poly-A sequence, unmasking of a poly-A sequence and incorporation of one or more 3'-non translated regions, has a synergistic influence on the stability of RNA and increase in translation efficiency.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA. The half-life of RNA may influence the "duration of expression" of the RNA. It can be expected that RNA having a long half-life will be expressed for an extended time period.

Of course, if according to the present invention it is desired to decrease stability and/or translation efficiency of RNA, it is possible to modify RNA so as to interfere with the function of elements as described above increasing the stability and/or translation efficiency of RNA.

The term "expression" is used according to the invention in its most general meaning and comprises the production of RNA and/or peptides, polypeptides or proteins, e.g. by transcription and/or translation. With respect to RNA, the term "expression" or "translation" relates in particular to the production of peptides, polypeptides or proteins. It also comprises partial expression of nucleic acids. Moreover, expression can be transient or stable.

According to the invention, the term expression also includes an "aberrant expression" or "abnormal expression". "Aberrant expression" or "abnormal expression" means according to the invention that expression is altered, preferably increased, compared to a reference, e.g. a state in a subject not having a disease associated with aberrant or abnormal expression of a certain protein, e.g., a tumor antigen. An increase in expression refers to an increase by at least 10%, in particular at least 20%, at least 50% or at least 100%, or more. In one embodiment, expression is only found in a diseased tissue, while expression in a healthy tissue is repressed.

The term "specifically expressed" means that a protein is essentially only expressed in a specific tissue or organ. For example, a tumor antigen specifically expressed in gastric mucosa means that said protein is primarily expressed in gastric mucosa and is not expressed in other tissues or is not expressed to a significant extent in other tissue or organ types. Thus, a protein that is exclusively expressed in cells of the gastric mucosa and to a significantly lesser extent in any other tissue, such us testis, is specifically expressed in cells of the gastric mucosa. In some embodiments, a tumor antigen may also be specifically expressed under normal conditions in more than one tissue type or organ, such as in 2 or 3 tissue types or organs, but preferably in not more than 3 different tissue or organ types. In this case, the tumor antigen is then specifically expressed in these organs. For example, if a tumor antigen is expressed under normal conditions preferably to an approximately equal extent in lung and stomach, said tumor antigen is specifically expressed in lung and stomach.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". According to the present invention, the RNA used in the present invention preferably is in vitro transcribed RNA (IVT-RNA) and may be obtained by in vitro transcription of an appropriate DNA template. The promoter for controlling transcription can be any promoter for any RNA polymerase. Particular examples of RNA polymerases are the T7, T3, and SP6 RNA polymerases. Preferably, the in vitro transcription according to the invention is controlled by a T7 or SP6 promoter. A DNA template for in vitro transcription may be obtained by cloning of a nucleic acid, in particular cDNA, and introducing it into an appropriate vector for in vitro transcription. The cDNA may be obtained by reverse transcription of RNA.

The term "translation" according to the invention relates to the process in the ribosomes of a cell by which a strand of messenger RNA directs the assembly of a sequence of amino acids to make a peptide, polypeptide or protein.

Expression control sequences or regulatory sequences, which according to the invention may be linked functionally with a nucleic acid, can be homologous or heterologous with respect to the nucleic acid. A coding sequence and a regulatory sequence are linked together "functionally" if they are bound together covalently, so that the transcription or translation of the coding sequence is under the control or under the influence of the regulatory sequence. If the coding sequence is to be translated into a functional protein, with functional linkage of a regulatory sequence with the coding sequence, induction of the regulatory sequence leads to a transcription of the coding sequence, without causing a reading frame shift in the coding sequence or inability of the coding sequence to be translated into the desired protein or peptide.

The term "expression control sequence" or "regulatory sequence" comprises, according to the invention, promoters, ribosome-binding sequences and other control elements, which control the transcription of a nucleic acid or the translation of the derived RNA. In certain embodiments of the invention, the regulatory sequences can be controlled. The precise structure of regulatory sequences can vary depending on the species or depending on the cell type, but generally comprises 5'-untranscribed and 5'- and 3'-untranslated sequences, which are involved in the initiation of transcription or translation, such as TATA-box, capping-sequence, CAAT-sequence and the like. In particular, 5'-untranscribed regulatory sequences comprise a promoter region that includes a promoter sequence for transcriptional control of the functionally bound gene. Regulatory sequences can also comprise enhancer sequences or upstream activator sequences.

Preferably, according to the invention, RNA to be expressed in a cell is introduced into said cell. In one embodiment of the methods according to the invention, the RNA that is to be introduced into a cell is obtained by in vitro transcription of an appropriate DNA template.

According to the invention, terms such as "RNA capable of expressing" and "RNA encoding" are used interchangeably herein and with respect to a particular peptide or polypeptide mean that the RNA, if present in the appropriate environment, preferably within a cell, can be expressed to produce said peptide or polypeptide. Preferably, RNA according to the invention is able to interact with the cellular translation machinery to provide the peptide or polypeptide it is capable of expressing.

Terms such as "transferring", "introducing" or "transfecting" are used interchangeably herein and relate to the introduction of nucleic acids, in particular exogenous or heterologous nucleic acids, in particular RNA into a cell. According to the present invention, the cell can form part of an organ, a tissue and/or an organism. According to the present invention, the administration of a nucleic acid is either achieved as naked nucleic acid or in combination with an administration reagent. Preferably, administration of nucleic acids is in the form of naked nucleic acids. Preferably, the RNA is administered in combination with stabilizing substances such as RNase inhibitors. The present invention also envisions the repeated introduction of nucleic acids into cells to allow sustained expression for extended time periods.

Cells can be transfected with any carriers with which RNA can be associated, e.g. by forming complexes with the RNA or forming vesicles in which the RNA is enclosed or encapsulated, resulting in increased stability of the RNA compared to naked RNA. Carriers useful according to the invention include, for example, lipid-containing carriers such as anionic lipids, liposomes, in particular cationic liposomes, and micelles, and nanoparticles. Cationic lipids may form complexes with negatively charged nucleic acids. Any cationic lipid may be used according to the invention.

Preferably, the introduction of RNA which encodes a peptide or polypeptide into a cell, in particular into a cell present in vivo, results in expression of said peptide or polypeptide in the cell. In particular embodiments, the targeting of the nucleic acids to particular cells is preferred. In such embodiments, a carrier which is applied for the administration of the nucleic acid to a cell (for example, a retrovirus or a liposome), exhibits a targeting molecule. For example, a molecule such as an antibody which is specific for a surface membrane protein on the target cell or a ligand for a receptor on the target cell may be incorporated into the nucleic acid carrier or may be bound thereto. In case the nucleic acid is administered by liposomes, proteins which bind to a surface membrane protein which is associated with endocytosis may be incorporated into the liposome formulation in order to enable targeting and/or uptake. Such proteins encompass capsid proteins of fragments thereof which are specific for a particular cell type, antibodies against proteins which are internalized, proteins which target an intracellular location etc.

The term "cell" or "host cell" preferably is an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transformed or transfected with an exogenous nucleic acid. The term "cell" includes according to the invention prokaryotic cells (e.g., E. coli) or eukaryotic cells (e.g., dendritic cells, B cells, CHO cells, COS cells, K562 cells, HEK293 cells, HELA cells, yeast cells, and insect cells). The exogenous nucleic acid may be found inside the cell (i) freely dispersed as such, (ii) incorporated in a recombinant vector, or (iii) integrated into the host cell genome or mitochondrial DNA. Mammalian cells are particularly preferred, such as cells from humans, mice, hamsters, pigs, goats, and primates. The cells may be derived from a large number of tissue types and include primary cells and cell lines. Specific examples include keratinocytes, peripheral blood leukocytes, bone marrow stem cells, and embryonic stem cells. In further embodiments, the cell is an antigen-presenting cell, in particular a dendritic cell, a monocyte, or macrophage.

A cell which comprises a nucleic acid molecule preferably expresses the peptide or polypeptide encoded by the nucleic acid.

The term "clonal expansion" refers to a process wherein a specific entity is multiplied. In the context of the present invention, the term is preferably used in the context of an immunological response in which lymphocytes are stimulated by an antigen, proliferate, and the specific lymphocyte recognizing said antigen is amplified. Preferably, clonal expansion leads to differentiation of the lymphocytes.

Terms such as "reducing" or "inhibiting" relate to the ability to cause an overall decrease, preferably of 5% or greater, 10% or greater, 20% or greater, more preferably of 50% or greater, and most preferably of 75% or greater, in the level. The term "inhibit" or similar phrases includes a complete or essentially complete inhibition, i.e. a reduction to zero or essentially to zero.

Terms such as "increasing", "enhancing", "promoting" or "prolonging" preferably relate to an increase, enhancement, promotion or prolongation by about at least 10%, preferably at least 20%, preferably al least 30%, preferably at least 40%, preferably at least 50%, preferably at least 80%, preferably at least 100%, preferably at least 200% and in particular at least 300%. These terms may also relate to an increase, enhancement, promotion or prolongation from zero or a non-measurable or non-delectable level to a level of more than zero or a level which is measurable or detectable.

The present invention provides vaccines such as cancer vaccines designed on the basis of amino acid modifications or modified peptides predicted as being immunogenic by the methods of the present invention.

According to the invention, the term "vaccine" relates to a pharmaceutical preparation (pharmaceutical composition) or product that upon administration induces an immune response, in particular a cellular immune response, which recognizes and attacks a pathogen or a diseased cell such as a cancer cell. A vaccine may be used for the prevention or treatment of a disease. The term "personalized cancer vaccine" or "individualized cancer vaccine" concerns a particular cancer patient and means that a cancer vaccine is adapted to the needs or special circumstances of an individual cancer patient.

In one embodiment, a vaccine provided according to the invention may comprise a peptide or polypeptide comprising one or more amino acid modifications or one or more modified peptides predicted as being immunogenic by the methods of the invention or a nucleic acid, preferably RNA, encoding said peptide or polypeptide.

The cancer vaccines provided according to the invention when administered to a patent provide one or more T cell epitopes suitable for stimulating, priming and/or expanding T cells specific for the patient's tumor. The T cells are preferably directed against cells expressing antigens from which the T cell epitopes are derived. Thus, the vaccines described herein are preferably capable of inducing or promoting a cellular response, preferably cytotoxic T cell activity, against a cancer disease characterized by presentation of one or more tumor-associated neoantigens with class I MHC. Since a vaccine provided according to the present invention will target cancer specific mutations it will be specific for the patient's tumor.

A vaccine provided according to the invention relates to a vaccine which when administered to a patent preferably provides one or more T cell epitopes, such as 2 or more, 5 or more, 10 or more, 15 or more, 20 or more, 25 or more, 30 or more and preferably up to 60, up to 55, up to 50, up to 45, up to 40, up to 35 or up to 30 T cell epitopes, incorporating amino acid modifications or modified peptides predicted as being immunogenic by the methods of the invention. Such T cell epitopes are also termed "neo-epitopes" herein. Presentation of these epitopes by cells of a patient, in particular antigen presenting cells, preferably results in T cells targeting the epitopes when bound to MHC and thus, the patient's tumor, preferably the primary tumor as well as tumor metastases, expressing antigens from which the T cell epitopes are derived and presenting the same epitopes on the surface of the tumor cells.

The methods of the invention may comprise the further step of determining the usability of the identified amino acid modifications or modified peptides for cancer vaccination. Thus further steps can involve one or more of the following: (i) assessing whether the modifications are located in known or predicted MHC presented epitopes, (ii) in vitro and/or in silico testing whether the modifications are located in MHC presented epitopes, e.g. testing whether the modifications are part of peptide sequences which are processed into and/or presented as MHC presented epitopes, and (iii) in vitro testing whether the envisaged modified epitopes, in particular when present in their natural sequence context, e.g. when flanked by amino acid sequences also flanking said epitopes in the naturally occurring protein, and when expressed in antigen presenting cells are able to stimulate T cells such as T cells of the patient having the desired specificity. Such flanking sequences each may comprise 3 or more, 5 or more, 10 or more, 15 or more, 20 or more and preferably up to 50, up to 45, up to 40, up to 35 or up to 30 amino acids and may flank the epitope sequence N-terminally and/or C-terminally.

Modified peptides determined according to the invention may be ranked for their usability as epitopes for cancer vaccination. Thus, in one aspect, the method of the invention comprises a manual or computer-based analytical process in which the identified modified peptides are analyzed and selected for their usability in the respective vaccine to be provided. In a preferred embodiment, said analytical process is a computational algorithm-based process. Preferably, said analytical process comprises determining and/or ranking epitopes according to a prediction of their capacity of being immunogenic.

The neo-epitopes identified according to the invention and provided by a vaccine of the invention are preferably present in the form of a polypeptide comprising said neo-epitopes such as a polyepitopic polypeptide or a nucleic acid, in particular RNA, encoding said polypeptide. Furthermore, the neo-epitopes may be present in the polypeptide in the form of a vaccine sequence, i.e. present in their natural sequence context, e.g. flanked by amino acid sequences also flanking said epitopes in the naturally occurring protein. Such flanking sequences each may comprise 5 or more, 10 or more, 15 or more, 20 or more and preferably up to 50, up to 45, up to 40, up to 35 or up to 30 amino acids and may flank the epitope sequence N-terminally and/or C-terminally. Thus, a vaccine sequence may comprise 20 or more, 25 or more, 30 or more, 35 or more, 40 or more and preferably up to 50, up to 45, up to 40, up to 35 or up to 30 amino acids. In one embodiment, the neo-epitopes and/or vaccine sequences are lined up in the polypeptide head-to-tail.

In one embodiment, the neo-epitopes and/or vaccine sequences are spaced by linkers, in particular neutral linkers. The term "linker" according to the invention relates to a peptide added between two peptide domains such as epitopes or vaccine sequences to connect said peptide domains. There is no particular limitation regarding the linker sequence. However, it is preferred that the linker sequence reduces steric hindrance between the two peptide domains, is well translated, and supports or allows processing of the epitopes. Furthermore, the linker should have no or only little immunogenic sequence elements. Linkers preferably should not create non-endogenous neo-epitopes like those generated from the junction suture between adjacent neo-epitopes, which might generate unwanted immune reactions. Therefore, the polyepitopic vaccine should preferably contain linker sequences which are able to reduce the number of unwanted MHC binding junction epitopes. Hoyt et al. (*EMBO J.* 25(8), 1720-9, 2006) and Zhang el al. (*J. Biol. Chem.,* 279(10), 8635-41, 2004) have shown that glycine-rich sequences impair proteasomal processing and thus the use of glycine rich linker sequences act to minimize the number of linker-contained peptides that can be processed by the proteasome. Furthermore, glycine was observed to inhibit a strong binding in MHC binding groove positions (Abastado et al., *J. Immunol.* 151(7), 3569-75, 1993). Schlessinger et al. (*Proteins,* 61(1), 115-26, 2005) had found that amino acids glycine and serine included in an amino acid sequence result in a more flexible protein that is more efficiently translated and processed by the proteasome, enabling better access to the encoded neo-epitopes. The linker each may comprise 3 or more, 6 or more, 9 or more, 10 or more, 15 or more, 20 or more and preferably up to 50, up to 45, up to 40, up to 35 or up to 30 amino acids. Preferably the linker is enriched in glycine and/or serine amino acids. Preferably, at least 50%, at least 60%, at least 70%, at least 80%, at least 90%, or at least 95% of the amino acids of the linker are glycine and/or serine. In one preferred embodiment, a linker is substantially composed of the amino acids glycine and serine. In one embodiment, the linker comprises the amino acid sequence $(GGS)_a(GSS)_b(GGG)_c(SSG)_d(GSG)_e$ wherein a, b, c, d and e is independently a number selected from 0, 1, 2, 3, 4, 5, 6, 7, 8, 9, 10, 11, 12, 13, 14, 15, 16, 17, 18, 19, or 20 (SEQ ID NO: 91) and wherein a+b+c+d+e are different from 0 and preferably are 2 or more, 3 or more, 4 or more or 5 or more. In one embodiment, the linker comprises a sequence as described herein including the linker sequences described in the examples such as the sequence GGSGGGGSG (SEQ ID NO: 92).

In one particularly preferred embodiment, a polypeptide incorporating one or more neo-epitopes such as a polyepitopic polypeptide according to the present invention is administered to a patient in the form of a nucleic acid, preferably RNA such as in vitro transcribed or synthetic RNA, which may be expressed in cells of a patient such as antigen presenting cells to produce the polypeptide. The present invention also envisions the administration of one or more multiepitopic polypeptides which for the purpose of the present invention are comprised by the term "polyepitopic polypeptide", preferably in the form of a nucleic acid, preferably RNA such as in vitro transcribed or synthetic RNA, which may be expressed in cells of a patient such as antigen presenting cells to produce the one or more polypeptides. In the case of an administration of more than one multiepitopic polypeptide the neo-epitopes provided by the different multiepitopic polypeptides may be different or partially overlapping. Once present in cells of a patient such as antigen presenting cells the polypeptide according to the invention is processed to produce the neo-epitopes identified according to the invention. Administration of a vaccine provided according to the invention preferably provides MHC class II-presented epitopes that are capable of eliciting a CD4+ helper T cell response against cells expressing antigens from which the MHC presented epitopes are derived. Administration of a vaccine provided according to the invention may also provide MHC class 1-presented epitopes that are capable of eliciting a CD8+ T cell response against cells expressing antigens from which the MHC presented epitopes are derived. Furthermore, administration of a vaccine provided according to the invention may provide one or more neo-epitopes (including known neo-epitopes and neo-epitopes identified according to the invention) as well as one or more epitopes not containing cancer specific somatic mutations but being expressed by cancer cells and preferably inducing an immune response against cancer cells, preferably a cancer specific immune response. In one embodiment, administration of a vaccine provided according to the invention provides neo-epitopes that are MHC class II-presented epitopes and/or are capable of eliciting a CD4+ helper T cell response against cells expressing antigens from which the MHC presented epitopes are derived as well as epitopes not containing cancer-specific somatic mutations that are MHC class I-presented epitopes and/or are capable of eliciting a CD8+ T cell response against cells expressing antigens from which the MHC presented epitopes are derived. In one embodiment, the epitopes not containing cancer-specific somatic mutations are derived from a tumor antigen. In one embodiment, the neo-epitopes and epitopes not containing cancer-specific somatic mutations have a synergistic effect in the treatment of cancer. Preferably, a vaccine provided according to the invention is useful for polyepitopic stimulation of cytotoxic and/or helper T cell responses.

The vaccine provided according to the invention may be a recombinant vaccine.

The term "recombinant" in the context of the present invention means "made through genetic engineering". Preferably, a "recombinant entity" such as a recombinant polypeptide in the context of the present invention is not occurring naturally, and preferably is a result of a combination of entities such as amino acid or nucleic acid sequences which are not combined in nature. For example, a recombinant polypeptide in the context of the present invention may contain several amino acid sequences such as neo-epitopes or vaccine sequences derived from different proteins or different portions of the same protein fused together, e.g., by peptide bonds or appropriate linkers.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

Agents, compositions and methods described herein can be used to treat a subject with a disease, e.g., a disease characterized by the presence of diseased cells expressing an antigen and presenting a fragment thereof. Particularly preferred diseases are cancer diseases. Agents, compositions and methods described herein may also be used for immunization or vaccination to prevent a disease described herein.

According to the invention, the term "disease" refers to any pathological state, including cancer diseases, in particular those forms of cancer diseases described herein.

The term "normal" refers to the healthy state or the conditions in a healthy subject or tissue, i.e., non-pathological conditions, wherein "healthy" preferably means non-cancerous.

"Disease involving cells expressing an antigen" means according to the invention that expression of the antigen in cells of a diseased tissue or organ is detected. Expression in cells of a diseased tissue or organ may be increased compared to the state in a healthy tissue or organ. An increase refers to an increase by at least 10%, in particular at least 20%, at least 50%, at least 100%, at least 200%, at least 500%, at least 1000%, at least 10000% or even more. In one embodiment, expression is only found in a diseased tissue, while expression in a healthy tissue is repressed. According to the invention, diseases involving or being associated with cells expressing an antigen include cancer diseases.

According to the invention, the term "tumor" or "tumor disease" refers to an abnormal growth of cells (called neoplastic cells, tumorigenous cells or tumor cells) preferably forming a swelling or lesion. By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant.

Cancer (medical term: malignant neoplasm) is a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Most cancers form a tumor but some, like leukemia, do not. Malignancy, malignant neoplasm, and malignant tumor are essentially synonymous with cancer.

Neoplasm is an abnormal mass of tissue as a result of neoplasia. Neoplasia (new growth in Greek) is the abnormal proliferation of cells. The growth of the cells exceeds, and is uncoordinated with that of the normal tissues around it. The growth persists in the same excessive manner even after cessation of the stimuli. It usually causes a lump or tumor. Neoplasms may be benign, pre-malignant or malignant.

"Growth of a tumor" or "tumor growth" according to the invention relates to the tendency of a tumor to increase its size and/or to the tendency of tumor cells to proliferate.

For purposes of the present invention, the terms "cancer" and "cancer disease" are used interchangeably with the terms "tumor" and "tumor disease".

Cancers are classified by the type of cell that resembles the tumor and, therefore, the tissue presumed to be the origin of the tumor. These are the histology and the location, respectively.

The term "cancer" according to the invention comprises carcinomas, adenocarcinomas, blastomas, leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the invention also comprises cancer metastases and relapse of cancer.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

The cells of a secondary or metastatic tumor are like those in the original tumor. This means, for example, that, if ovarian cancer metastasizes to the liver, the secondary tumor is made up of abnormal ovarian cells, not of abnormal liver cells. The tumor in the liver is then called metastatic ovarian cancer, not liver cancer.

The term "circulating tumor cells" or "CTCs" relates to cells that have detached from a primary tumor or tumor metastases and circulate in the bloodstream. CTCs may constitute seeds for subsequent growth of additional tumors (metastasis) in different tissues. Circulating tumor cells are found in frequencies in the order of 1-10 CTC per mL of whole blood in patients with metastatic disease. Research methods have been developed to isolate CTC. Several research methods have been described in the art to isolate CTCs, e.g. techniques which use of the fact that epithelial cells commonly express the cell adhesion protein EpCAM, which is absent in normal blood cells. Immunomagnetic bead-based capture involves treating blood specimens with antibody to EpCAM that has been conjugated with magnetic particles, followed by separation of tagged cells in a magnetic field. Isolated cells are then stained with antibody to another epithelial marker, cytokeratin, as well as a common leukocyte marker CD45, so as to distinguish rare CTCs from contaminating white blood cells. This robust and semi-automated approach identifies CTCs with an average yield of approximately 1 CTC/mL and a purity of 0.1% (Allard et al., 2004: *Clin Cancer Res* 10, 6897-6904). A second method for isolating CTCs uses a microfluidic-based CTC capture device which involves flowing whole blood through a chamber embedded with 80,000 microposts that have been rendered functional by coating with antibody to EpCAM. CTCs are then stained with secondary antibodies against either cytokeratin or tissue specific markers, such as PSA in prostate cancer or HER2 in breast cancer and are visualized by automated scanning of microposts in multiple planes along three dimensional coordinates. CTC-chips are able to identifying cytokerating-positive circulating tumor cells in patients with a median yield of 50 cells/ml and purity ranging from 1-80% (Nagrath et al., 2007: Nature 450, 1235-1239). Another possibility for isolating CTCs is using the CellSearch™ Circulating Tumor Cell (CTC) Test from Veridex, LLC (Raritan, N.J.) which captures, identifies, and counts CTCs in a tube of blood. The CellSearch™ system is a U.S. Food and Drug Administration (FDA) approved methodology for enumeration of CTC in whole blood which is based on a combination of immunomagnetic labeling and automated digital microscopy. There are other methods for isolating CTCs described in the literature all of which can be used in conjunction with the present invention.

A relapse or recurrence occurs when a person is affected again by a condition that affected them in the past. For example, if a patient has suffered from a tumor disease, has received a successful treatment of said disease and again develops said disease said newly developed disease may be considered as relapse or recurrence. However, according to the invention, a relapse or recurrence of a tumor disease may but does not necessarily occur al the site of the original tumor disease. Thus, for example, if a patient has suffered from ovarian tumor and has received a successful treatment a relapse or recurrence may be the occurrence of an ovarian tumor or the occurrence of a tumor at a site different to ovary. A relapse or recurrence of a tumor also includes situations wherein a tumor occurs at a site different to the site of the original tumor as well as at the site of the original tumor. Preferably, the original tumor for which the patient has received a treatment is a primary tumor and the tumor at a site different to the site of the original tumor is a secondary or metastatic tumor.

By "treat" is meant to administer a compound or composition as described herein to a subject in order to prevent or eliminate a disease, including reducing the size of a tumor or the number of tumors in a subject; arrest or slow a disease in a subject; inhibit or slow the development of a new disease in a subject; decrease the frequency or severity of symptoms and/or recurrences in a subject who currently has or who previously has had a disease; and/or prolong, i.e. increase the lifespan of the subject. In particular, the term "treatment of a disease" includes curing, shortening the duration, ameliorating, preventing, slowing down or inhibiting progression or worsening, or preventing or delaying the onset of a disease or the symptoms thereof.

By "being at risk" is meant a subject, i.e. a patient, that is identified as having a higher than normal chance of developing a disease, in particular cancer, compared to the general population. In addition, a subject who has had, or who currently has, a disease, in particular cancer, is a subject who has an increased risk for developing a disease, as such a subject may continue to develop a disease. Subjects who currently have, or who have had, a cancer also have an increased risk for cancer metastases.

The term "immunotherapy" relates to a treatment involving activation of a specific immune reaction. In the context of the present invention, terms such as "protect", "prevent", "prophylactic", "preventive", or "protective" relate to the prevention or treatment or both of the occurrence and/or the propagation of a disease in a subject and, in particular, to minimizing the chance that a subject will develop a disease or to delaying the development of a disease. For example, a person at risk for a tumor, as described above, would be a candidate for therapy to prevent a tumor.

A prophylactic administration of an immunotherapy, for example, a prophylactic administration of a vaccine of the invention, preferably protects the recipient from the development of a disease. A therapeutic administration of an immunotherapy, for example, a therapeutic administration of a vaccine of the invention, may lead to the inhibition of the progress/growth of the disease. This comprises the deceleration of the progress/growth of the disease, in particular a disruption of the progression of the disease, which preferably leads to elimination of the disease.

Immunotherapy may be performed using any of a variety of techniques, in which agents provided herein function to remove diseased cells from a patient. Such removal may take place as a result of enhancing or inducing an immune response in a patient specific for an antigen or a cell expressing an antigen.

Within certain embodiments, immunotherapy may be active immunotherapy, in which treatment relies on the in vivo stimulation of the endogenous host immune system to react against diseased cells with the administration of immune response-modifying agents (such as polypeptides and nucleic acids as provided herein).

The agents and compositions provided herein may be used alone or in combination with conventional therapeutic regimens such as surgery, irradiation, chemotherapy and/or bone marrow transplantation (autologous, syngeneic, allogeneic or unrelated).

The term "immunization" or "vaccination" describes the process of treating a subject with the purpose of inducing an immune response for therapeutic or prophylactic reasons.

The term "in vivo" relates to the situation in a subject.

The terms "subject", "individual", "organism" or "patient" are used interchangeably and relate to vertebrates, preferably mammals. For example, mammals in the context of the present invention are humans, non-human primates, domesticated animals such as dogs, cats, sheep, cattle, goats, pigs, horses etc., laboratory animals such as mice, rats, rabbits, guinea pigs, etc. as well as animals in captivity such as animals of zoos. The term "animal" as used herein also includes humans. The term "subject" may also include a patient, i.e., an animal, preferably a human having a disease, preferably a disease as described herein.

The term "autologous" is used to describe anything that is derived from the same subject. For example, "autologous transplant" refers to a transplant of tissue or organs derived from the same subject. Such procedures are advantageous because they overcome the immunological barrier which otherwise results in rejection.

The term "heterologous" is used to describe something consisting of multiple different elements. As an example, the transfer of one individual's bone marrow into a different individual constitutes a heterologous transplant. A heterologous gene is a gene derived from a source other than the subject.

As part of the composition for an immunization or a vaccination, preferably one or more agents as described herein are administered together with one or more adjuvants for inducing an immune response or for increasing an immune response. The term "adjuvant" relates to compounds which prolongs or enhances or accelerates an immune response. The composition of the present invention preferably exerts its effect without addition of adjuvants. Still, the composition of the present application may contain any known adjuvant. Adjuvants comprise a heterogeneous group of compounds such as oil emulsions (e.g., Freund's adjuvants), mineral compounds (such as alum), bacterial products (such as *Bordetella pertussis* toxin), liposomes, and immune-stimulating complexes. Examples for adjuvants are monophosphoryl-lipid-A (MPL SmithKline Beecham). Saponins such as QS21 (SmithKline Beecham), DQS21 (SmithKline Beecham: WO 96/33739), QS7, QS17, QS18, and QS-L1 (So et al., 1997, Mol. Cells 7: 178-186), incomplete Freund's adjuvants, complete Freund's adjuvants, vitamin E, montanid, alum, CpG oligonucleotides (Krieg et al., 1995, Nature 374: 546-549), and various water-in-oil emulsions which are prepared from biologically degradable oils such as squalene and/or tocopherol.

Other substances which stimulate an immune response of the patient may also be administered. It is possible, for example, to use cytokines in a vaccination, owing to their regulatory properties on lymphocytes. Such cytokines comprise, for example, inlerleukin-12 (IL-12) which was shown to increase the protective actions of vaccines (cf. *Science* 268:1432-1434, 1995), GM-CSF and IL-18.

There are a number of compounds which enhance an immune response and which therefore may be used in a vaccination. Said compounds comprise co-stimulating molecules provided in the form of proteins or nucleic acids such as B7-1 and B7-2 (CD80 and CD86, respectively).

According to the invention, a bodily sample may be a tissue sample, including body fluids, and/or a cellular sample. Such bodily samples may be obtained in the conventional manner such as by tissue biopsy, including punch biopsy, and by taking blood, bronchial aspirate, sputum, urine, feces or other body fluids. According to the invention, the term "sample" also includes processed samples such as fractions or isolates of biological samples, e.g. nucleic acid or cell isolates.

The agents such as vaccines and compositions described herein may be administered via any conventional route, including by injection or infusion. The administration may be carried out, for example, orally, intravenously, intraperitoneally, intramuscularly, subcutaneously or transdermally. In one embodiment, administration is carried out intranodally such as by injection into a lymph node. Other forms of administration envision the in vitro transaction of antigen presenting cells such as dendritic cells with nucleic acids described herein followed by administration of the antigen presenting cells.

The agents described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a patient is insufficient with an initial dose, higher doses (or effectively higher doses achieved by a different, more localized route of administration) may be used.

The pharmaceutical compositions described herein are preferably sterile and contain an effective amount of the therapeutically active substance to generate the desired reaction or the desired effect.

The pharmaceutical compositions described herein are generally administered in pharmaceutically compatible amounts and in pharmaceutically compatible preparation. The term "pharmaceutically compatible" refers to a nontoxic material which does not interact with the action of the active component of the pharmaceutical composition. Preparations of this kind may usually contain salts, buffer substances, preservatives, carriers, supplementing immunity-enhancing substances such as adjuvants, e.g. CpG oligonucleotides, cytokines, chemokines, saponin, GM-CSF and/or RNA and, where appropriate, other therapeutically active compounds. When used in medicine, the salts should be pharmaceutically compatible. However, salts which are not pharmaceutically compatible may used for preparing pharmaceutically compatible salts and are included in the invention. Pharmacologically and pharmaceutically compatible salts of this kind comprise in a non-limiting way those prepared from the following acids: hydrochloric, hydrobromic, sulfuric, nitric, phosphoric, maleic, acetic, salicylic, citric, formic, malonic, succinic acids, and the like. Pharmaceutically compatible salts may also be prepared as alkali metal salts or alkaline earth metal salts, such as sodium salts, potassium salts or calcium salts.

A pharmaceutical composition described herein may comprise a pharmaceutically compatible carrier. The term "carrier" refers to an organic or inorganic component, of a natural or synthetic nature, in which the active component is combined in order to facilitate application. According to the invention, the term "pharmaceutically compatible carrier" includes one or more compatible solid or liquid fillers, diluents or encapsulating substances, which are suitable for administration to a patient. The components of the pharmaceutical composition of the invention are usually such that no interaction occurs which substantially impairs the desired pharmaceutical efficacy.

The pharmaceutical compositions described herein may contain suitable buffer substances such as acetic acid in a salt, citric acid in a salt, boric acid in a salt and phosphoric acid in a salt.

The pharmaceutical compositions may, where appropriate, also contain suitable preservatives such as benzalkonium chloride, chlorobutanol, paraben and thimerosal.

The pharmaceutical compositions are usually provided in a uniform dosage form and may be prepared in a manner known per se. Pharmaceutical compositions of the invention may be in the form of capsules, tablets, lozenges, solutions, suspensions, syrups, elixirs or in the form of an emulsion, for example.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The present invention is described in detail by the figures and examples below, which are used only for illustration purposes and are not meant to be limiting. Owing to the description and the examples, further embodiments which are likewise included in the invention are accessible to the skilled worker.

FIGURES

FIG. 1. Non synonymous cancer-associated mutations are frequently immunogenic and pre-dominantly recognized by $CD4^+$ T cells. a, For immunogenicity testing, mice (n=5 for b and c, n=3 for d) were vaccinated with either synthetic peptides and poly (I:C) as adjuvant (b) or antigen-encoding RNA (c, d) representing the mutated epitopes (two mutations per mouse). Splenocytes wore restimulated ex vivo with the mutated peptide or an irrelevant control peptide and tested by IFNγ Elispot (sec exemplarily FIG. 2a) and intracellular cytokine and CD4/CD8 surface staining to assess subtype of elicited immune responses, b-c, T cell responses obtained by vaccinating C57BL/6 mice with epitopes mutated in the B16F10 tumor model. Left, prevalence of non-immunogenic. MHC class I or class II restricted mutated epitopes. Right, examples for detection and typing of mutation-specific T cells (see Table 1 for data on individual epitopes). d Left, prevalence of non-immunogenic. MHC class I or class II restricted mutated epitopes discovered in the CT26 model. Right, MHC restriction of immunogenic mutated epitopes prioritized based on predicted MHC class I binding and selected based on either good (0.1-2.1) or poor (>3.9) binding scores. Sec Table 2 for data on individual epitopes. Sequences in a ("Sequence analysis and mutation identification"): TTCAGGACCC A (SEQ ID NO: 93); TTCAGGACCCACACGA (SEQ ID NO: 94); TTCAGGACCCACACGACGGGAAGACAA (SEQ ID NO: 95); TTCAGGACCAACACGACGGGAAGACAAGT (SEQ ID NO: 96); CAGGACCCACACGACGGGTA-GACAAGT (SEQ ID NO: 97); ACC-CACACGACGGGTAG ACAAGT (SEQ ID NO: 98); ACC-CACACGAGCCCTAGACAAGT (SEQ ID NO: 99); GACGGGAAGACAAGT (SEQ ID NO: 100). Sequences in b and c: B16-M27 (SEQ ID NO: 10); B16-M30 (SEQ ID NO: 13).

Figure 2:
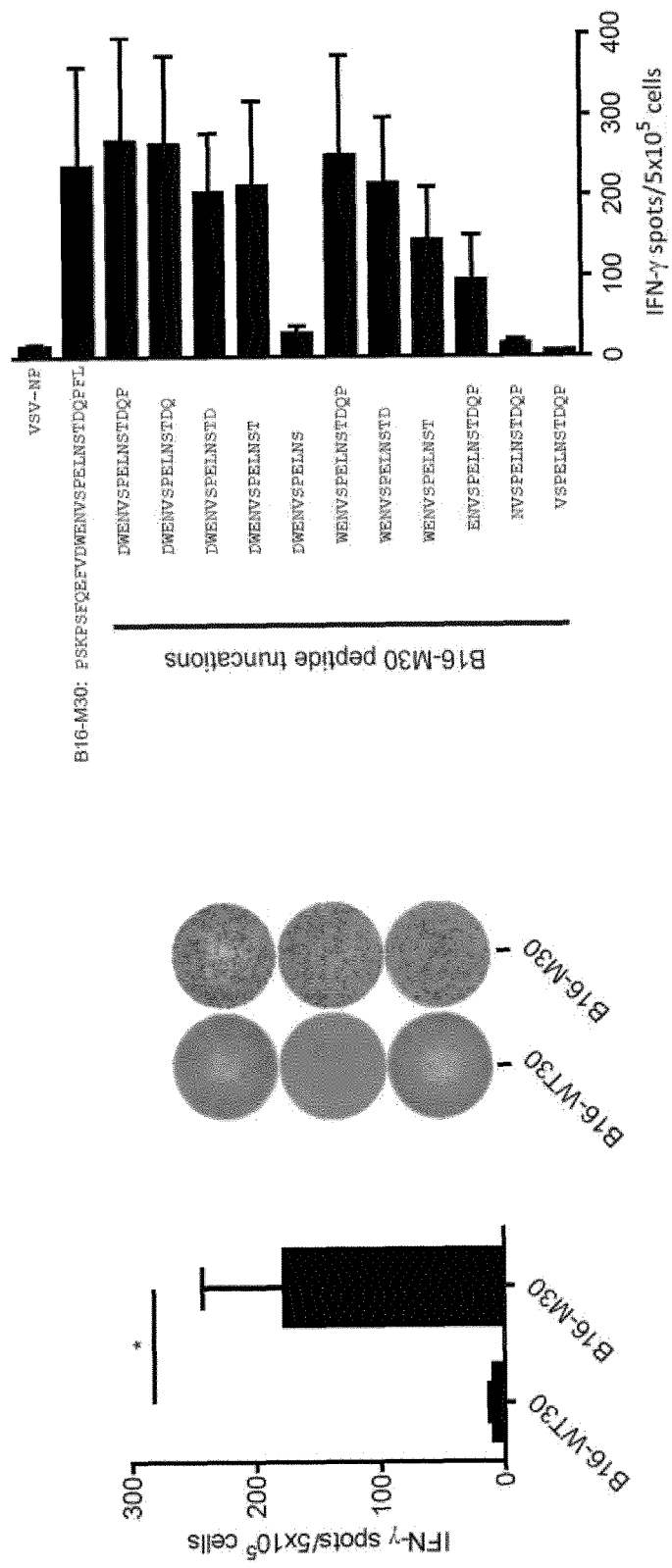
Figure 2:
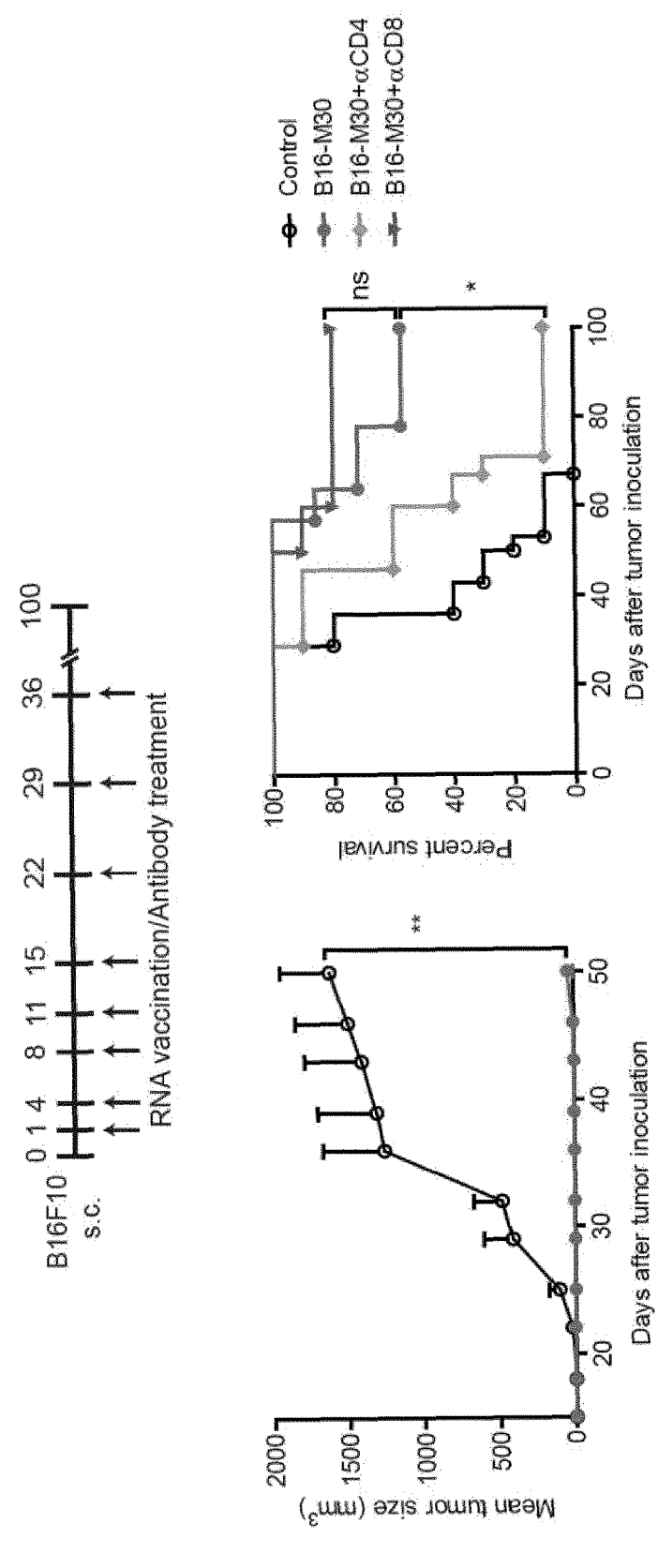
Figure 2:
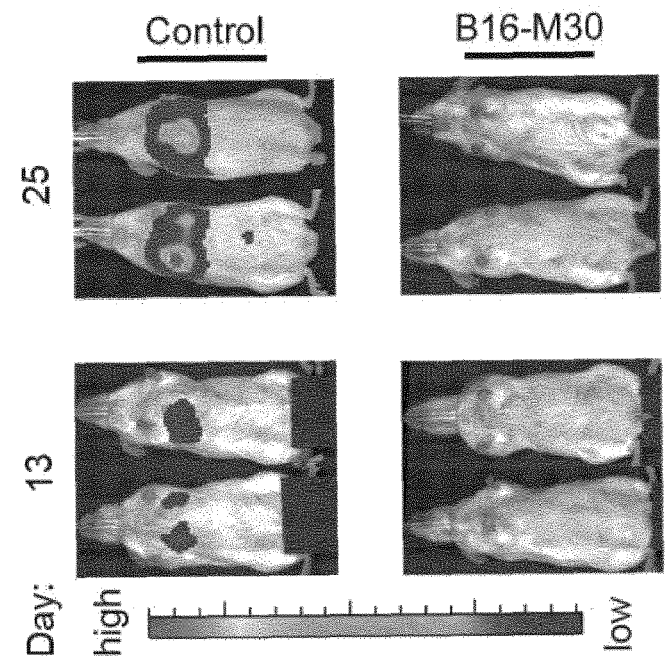
Figure 2:
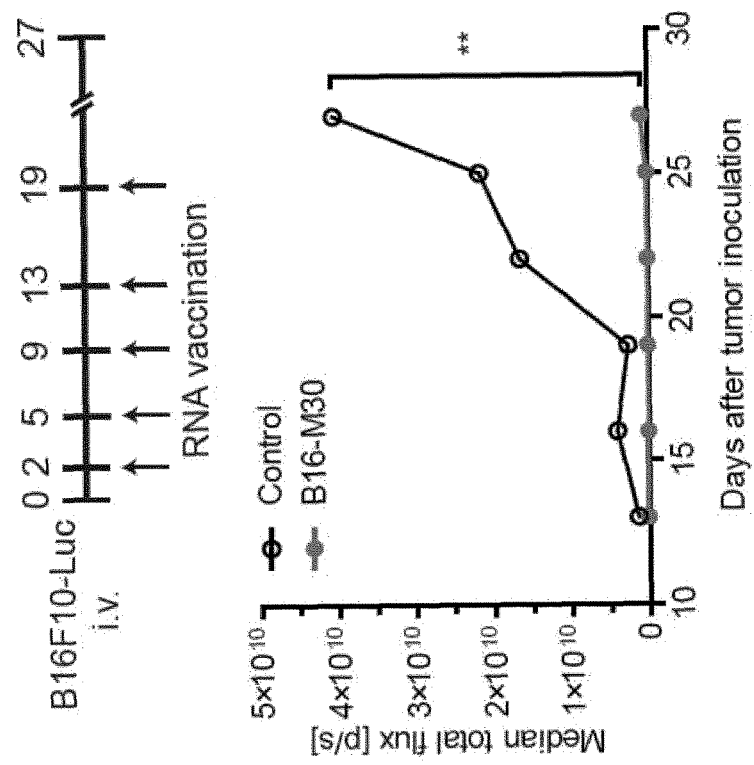
Figure 2:
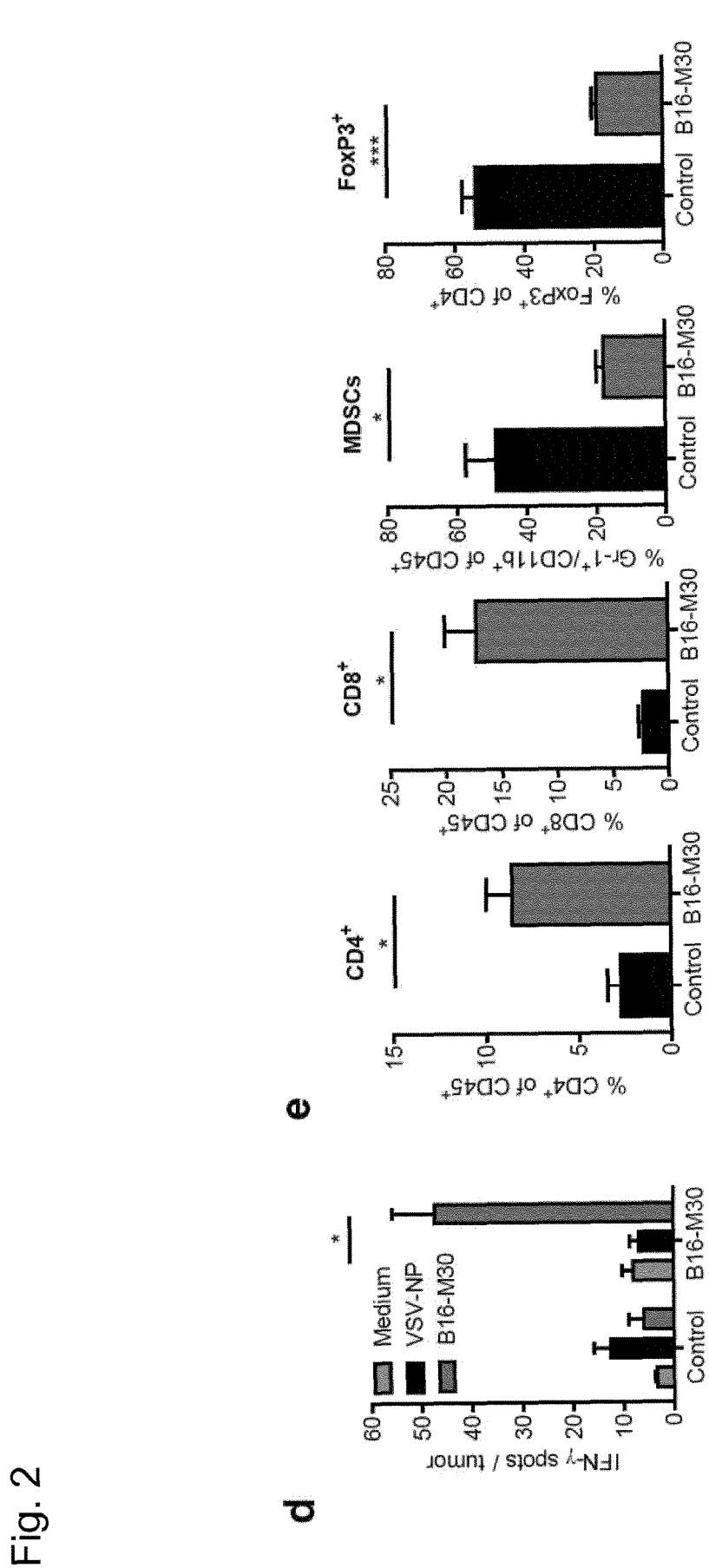

FIG. 2. Efficient tumor control and survival benefit in B16F10 melanoma by immunization with an RNA vaccine encoding a single mutated $CD4^+$ T cell epitope, a, Splenocytes of mice (n=5) vaccinated with B16-M30 RNA were tested by ELISpot for recognition of synthetic peptides. Left, the mutated (B16-M30) versus the corresponding wild type (B16-WT30) sequence. Right, definition of the minimal epitope by testing for recognition of truncated variants of B16-M30 (mean+SEM), b. The mean+SEM tumor growth (left) and survival (right) of C57BL/6 mice (n=10) inoculated subcutaneously with B16F10 tumors cells and left untreated (control) or immunized IV with B16-M30 encoding RNA (B16-M30) with or without administration of CD4 or CD8 depleting antibodies. c, B6 albino mice (n=10) developing lung metastases upon IV injection of luciferase transgenic B16F10 tumor cells (B16F10-LUC) were treated with B16-M30 encoding RNA (B16-M30) or irrelevant control RNA. Median tumor growth was determined by BLI. d, Single cell suspensions of B16F10 tumors of untreated (control, n=x) or B16-M30 RNA immunized mice (n=4) were restimulated with B16-M30 peptide, medium or irrelevant peptide (VSV-$NP_{52-59}$) and tested in an IFNγ ELISpot assay (mean+SEM). e. Flow cytometric characterization of tumor infiltrating leucocytes in B16-M30 RNA vaccinated mice. Depicted is the frequency of $CD4^+$, $CD8^+$ or $FoxP3^+$/$CD4^+$ T cells among $CD45^+$ cells and Gr-$1^+$/$CD11b^+$ cells (MDSCs) of untreated (control) or Mut30 RNA vaccinated C57BL/6 mice (n=3) inoculated subcutaneously with B16F10 tumors cells. Sequences in a: B16-M30 (SEQ ID NO: 13): DWENVSPELNSTDQP (SEQ ID NO: 82); DWE NVSPELNSTDQ (SEQ ID NO: 81); DWENVSPELNSTD (SEQ ID NO: 82); DWENVSPELNS T (SEQ ID NO: 83); DWENVSPELNS (SEQ ID NO: 84); WENVSPELN-STDQP (SEQ ID NO: 85); WENVSPELNSTD (SEQ ID NO: 86); WENVSPELNST (SEQ ID NO: 87); ENVSPELNS TDQP (SEQ ID NO: 88); NVSPELNSTDQP (SEQ ID NO: 89); VSPELNSTDQP (SEQ ID NO: 90).

Figure 3:
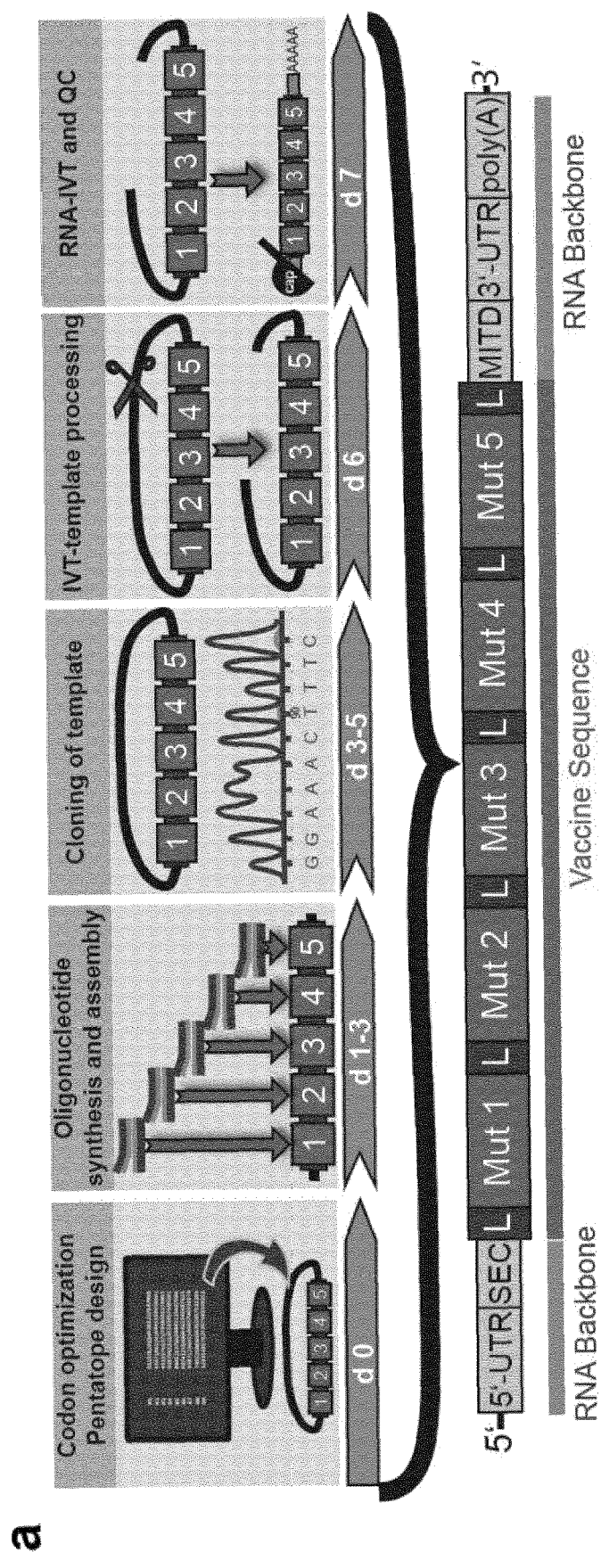
Figure 3:
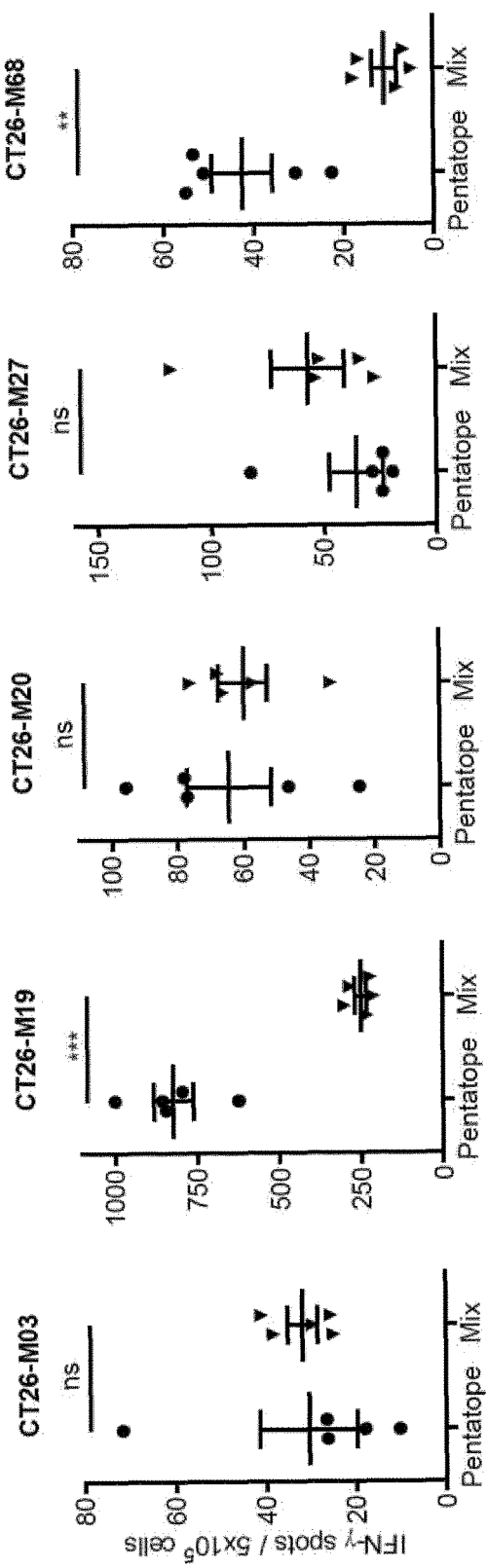
Figure 3:
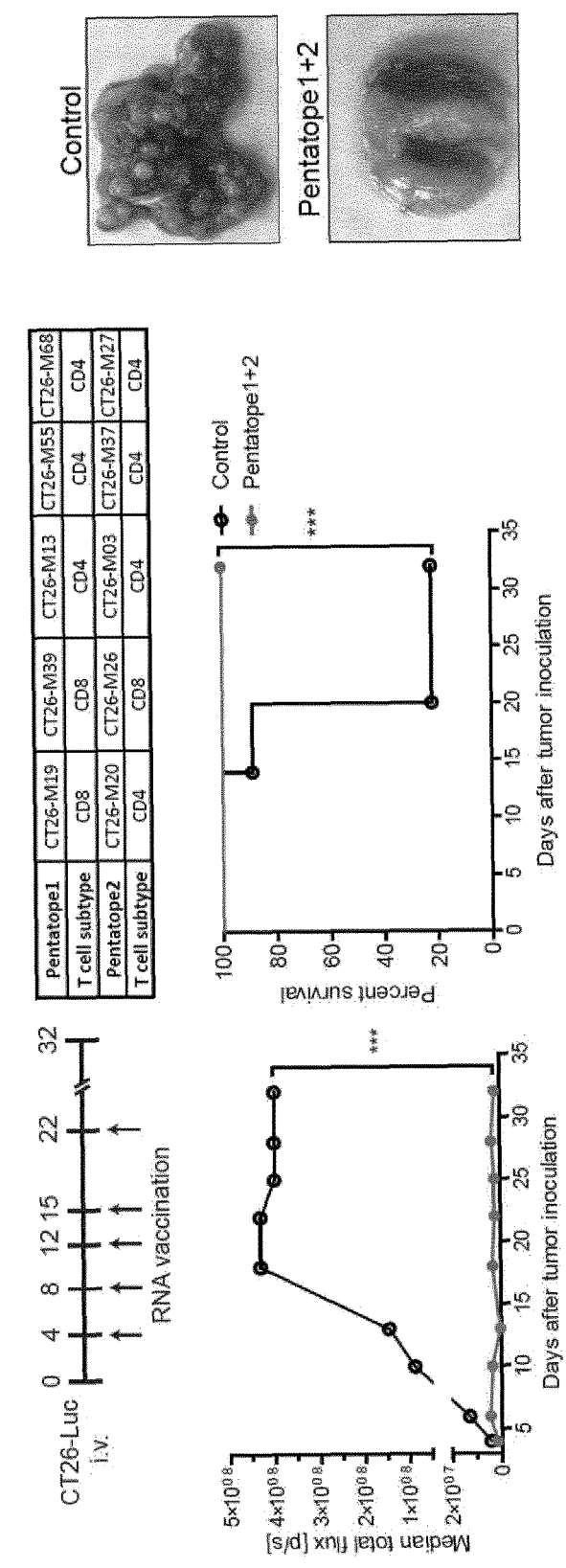
Figure 3:
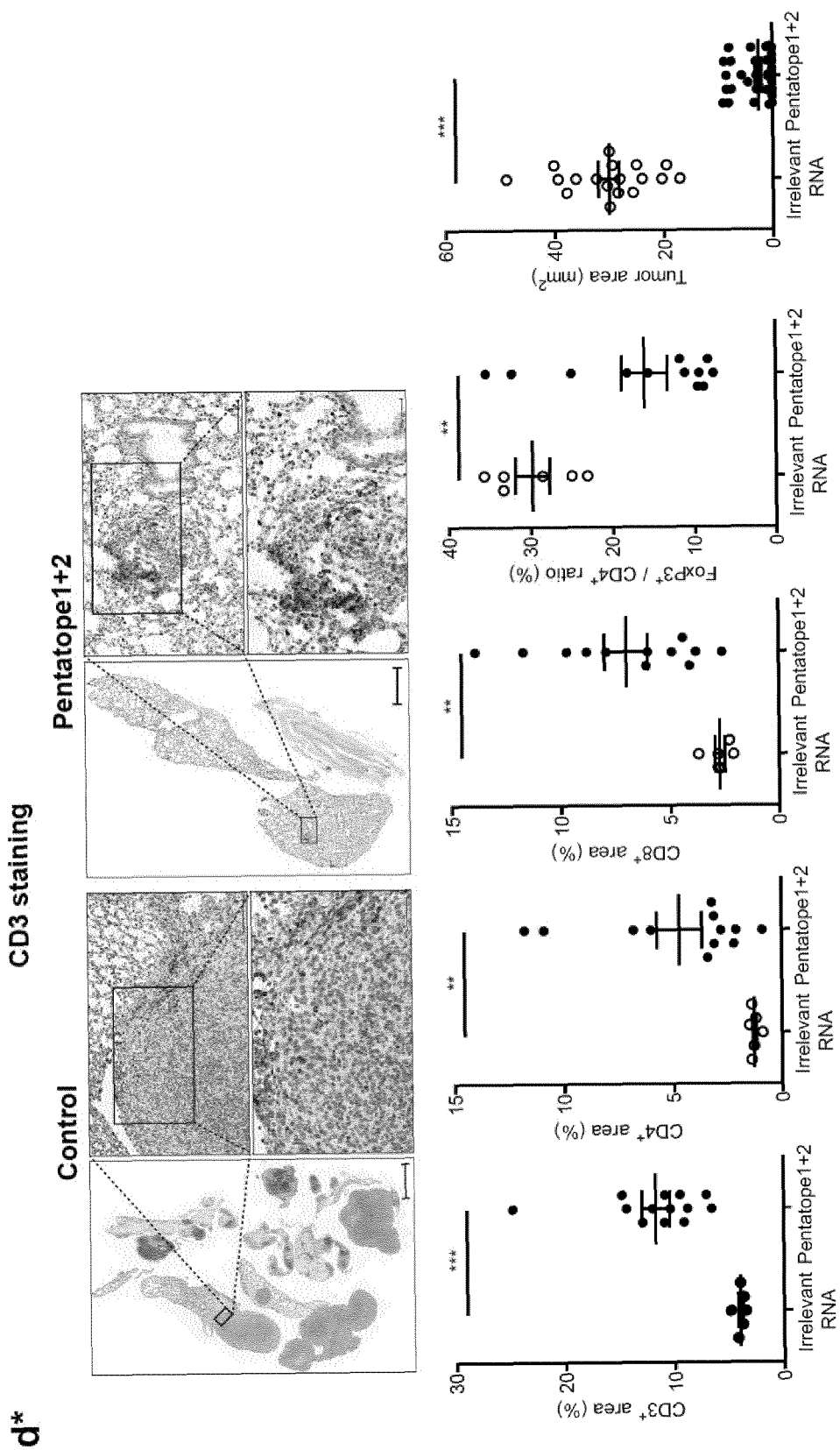

FIG. 3. Immunization with RNA pen mopes induces T cell responses against the individual mutated epitopes and confers disease control and significant survival benefit in mouse tumor models. a. Engineering of a poly-neo-epitope RNA vaccine. The RNA pentatope contains five 27mer sequences connected by gly/ser linkers inserted into the pST1-Sp-MITD-2hBgUTR-A120 backbone. (UTR, untranslated region; sp. signal peptide; MITD, MHC class I trafficking domain). b, BALB/c mice (n=5) were vaccinated either with pentatope RNA (35 μg) or the corresponding mixture of five RNA monotopes (7 μg each). T cell responses in peptide stimulated splenocytes of mice were measured ex vivo on day 19 in an IFNγ ELISpot assay (medium control subtracted mean+SEM). c, BALB/c mice (n=10) developing lung metastases upon IV injection of CT26-LUC cells were treated simultaneously with a mixture of two RNA pentatopes or left untreated (control). The median tumor growth by BLI (left), survival data (mid) and lungs from treated animals (right) are shown. d, CD3 stained tissue sections from the lungs of pentatope1+2 treated animals (upper panel). The left side of each panel shows the analyzed sections, the right side the magnifications (scale bar: scan: 1000 μm, upper pictures: 100 μm, lower pictures: 50 μm). $CD3^+$, $CD4^+$, $FoxP3^+$ and $CD8^+$ (calculated by $CD3^+$ area—$CD4^+$ area) areas in consecutive immunohistochemical lung tissue sections of control (n=6) or RNA pentatope (CD3: n=14; CD4, CD8, FoxP3: n=12) treated animals were quantified and proportions of tumor were calculated. The right figure depicts a comparison of tumor area in sections of control (n=18) and Pentatope1+2 (n=39) treated animals (tumor free animals of pentatope1+2 treatment group were excluded). Depicted are mean±SEM. Sequences in a ("Cloning of template"): GGAAACTTTC (SEQ ID NO: 105).

Figure 4:
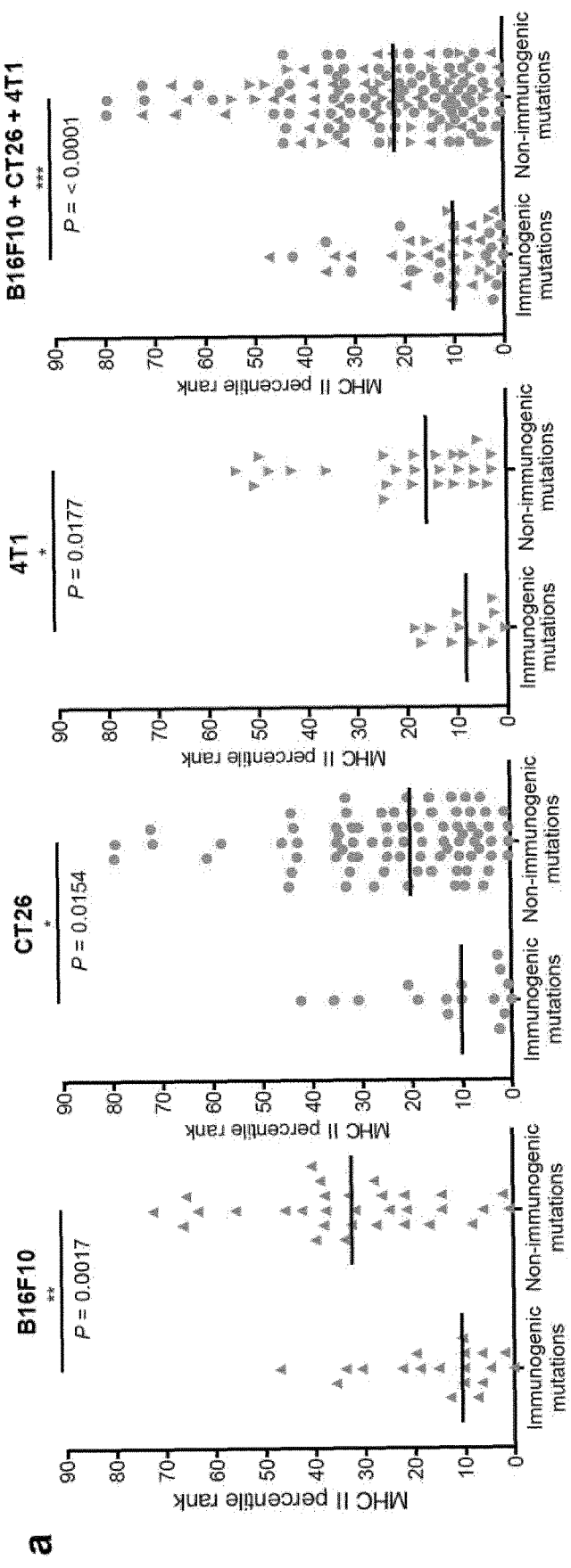
Figure 4:
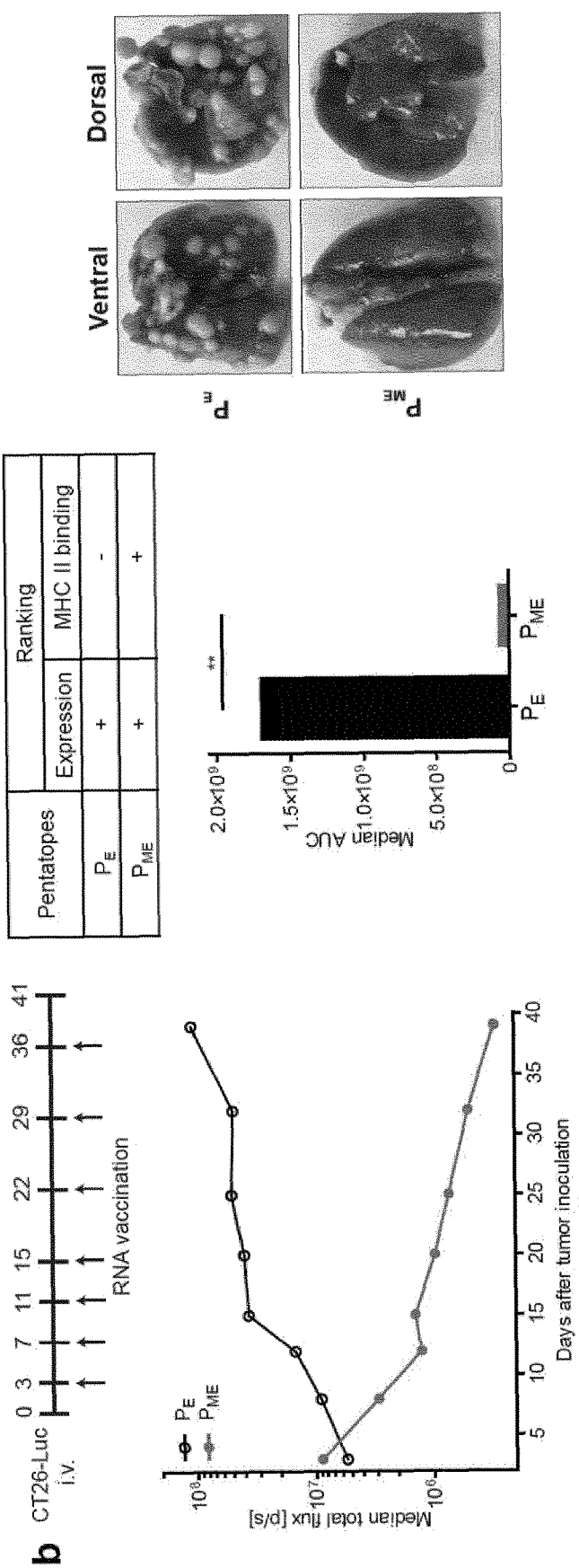
Figure 4:
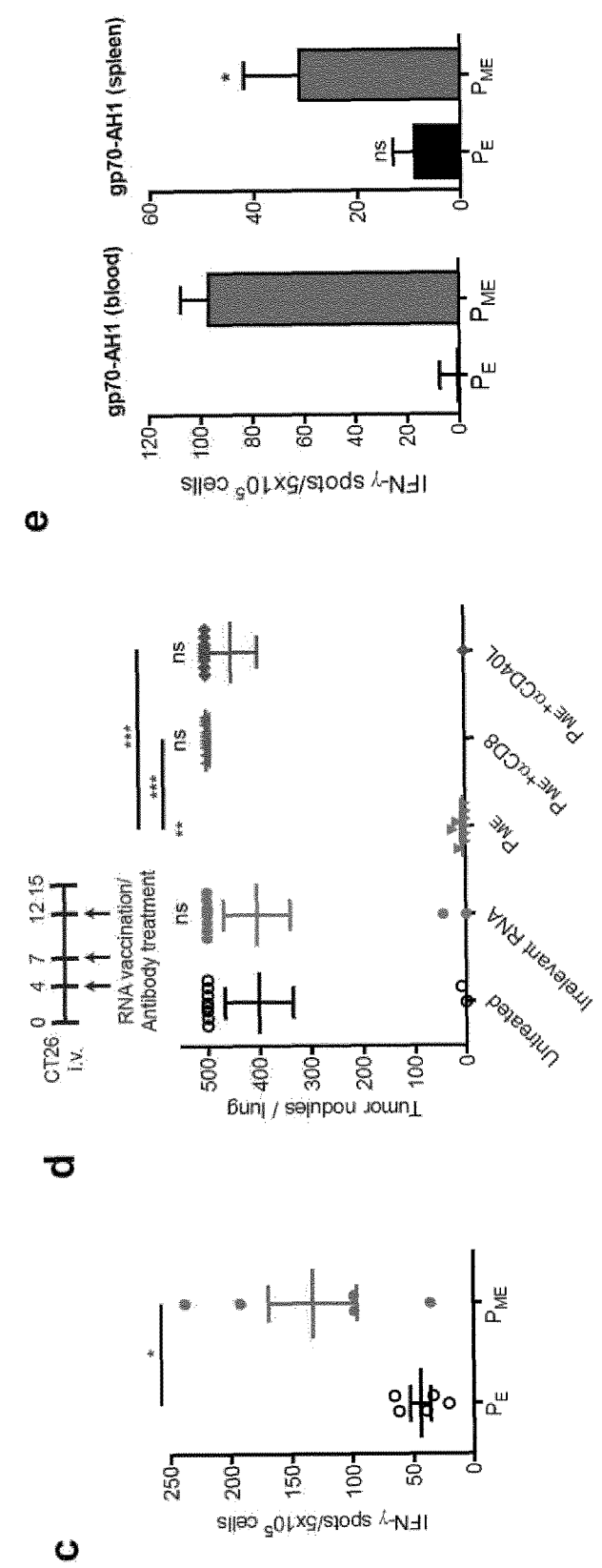
Figure 4:
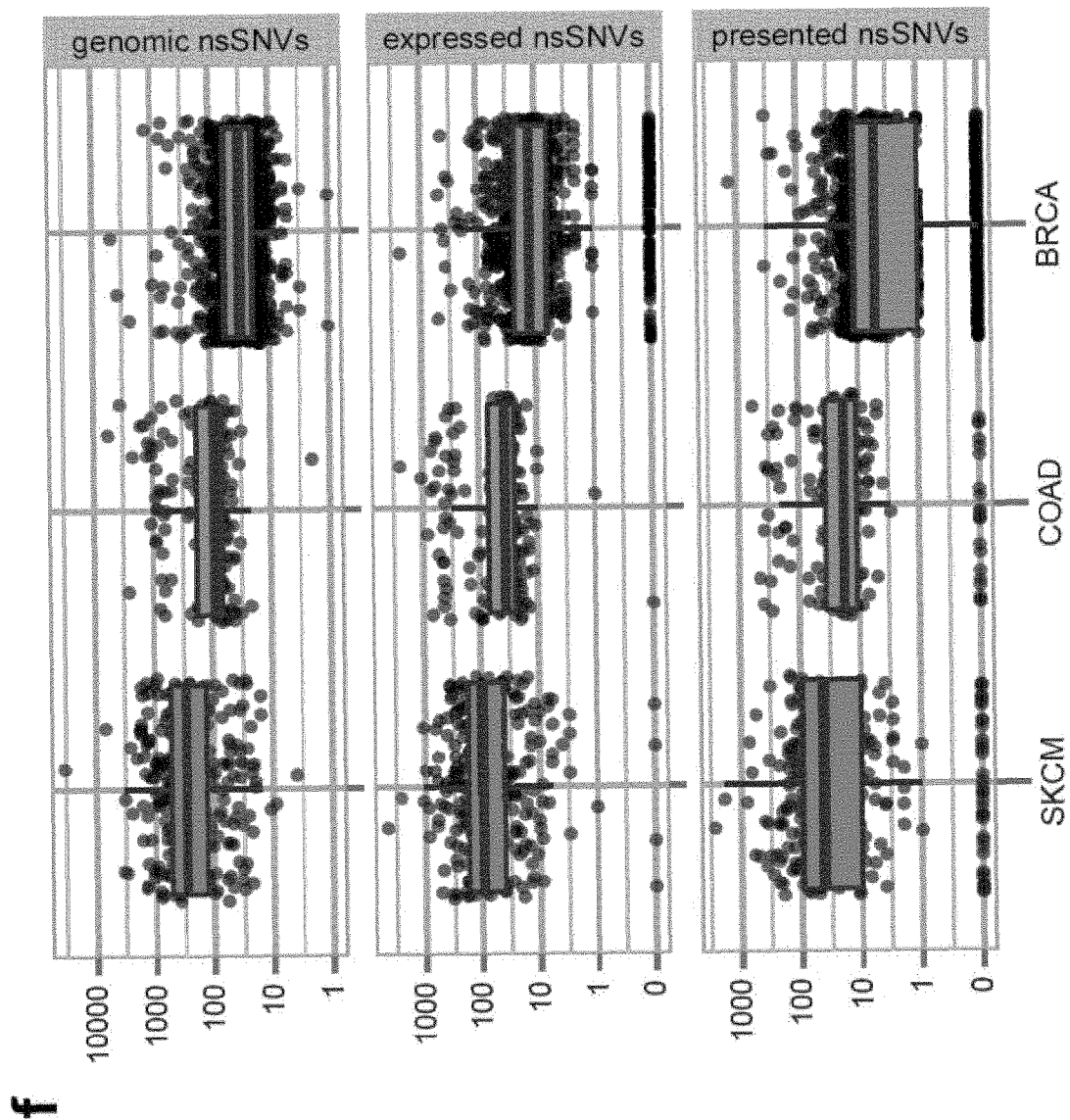

FIG. 4. RNA pentatope vaccines with mutations selected for in silico predicted favorable MHC class II binding properties and abundant expression confer potent antitumor control. a, Comparison of MHC II binding scores of immunogenic and non-immunogenic mutations (medians shown). b, Mutations with high expression levels were selected with ('ME' mutations) or without ('E' mutations) considering MHC class II binding score. See also Table 4. Ten mutations out of each category represented by two pentatopes each were used for vaccination of CT26-LUC lung tumor bearing mice. Tumor growth curves (left), area under the curve (mid) and ink treated lungs (right) are shown. c, Mice (5 per group) were analyzed for T cell responses against the vaccinated pentatopes by restimulation with RNA electroporated syngeneic BMDC in an IFNγ ELISpot assay. Each dot represents the mean spot count of one mouse subtracted by an irrelevant RNA control (mean±SEM). d, Tumor nodules per lung of BALB/c mice (n=10) inoculated IV with CT26 tumor cells and left untreated or injected with irrelevant RNA, pentatope1, pentatope2 or CT26-M19 RNA. e, T cell responses against $gp70_{423-431}$ (gp70-AH1) were determined via IFNγ ELISpot assay in blood (pooled from 5 mice, day 20 after tumor inoculation) and spleen (n=5). (Background (no peptide control) subtracted mean±SEM depicted). f, Somatic mutation and RNA-Seq data for individual human cancer samples (black dots) from The Cancer Genome Alias (TCGA) was employed to identify genomic (upper panel) and expressed (mid panel) non-synonymous single nucleotide variations (nsSNVs). (lower panel) Neo-epitopes predicted to bind to the patients' HLA-DRB1 alleles (percentile rank<10%) are shown (SKCM, skin cutaneous melanoma; COAD, colon adenocarcinoma; BRCA, breast invasive carcinoma).

Figure 5:
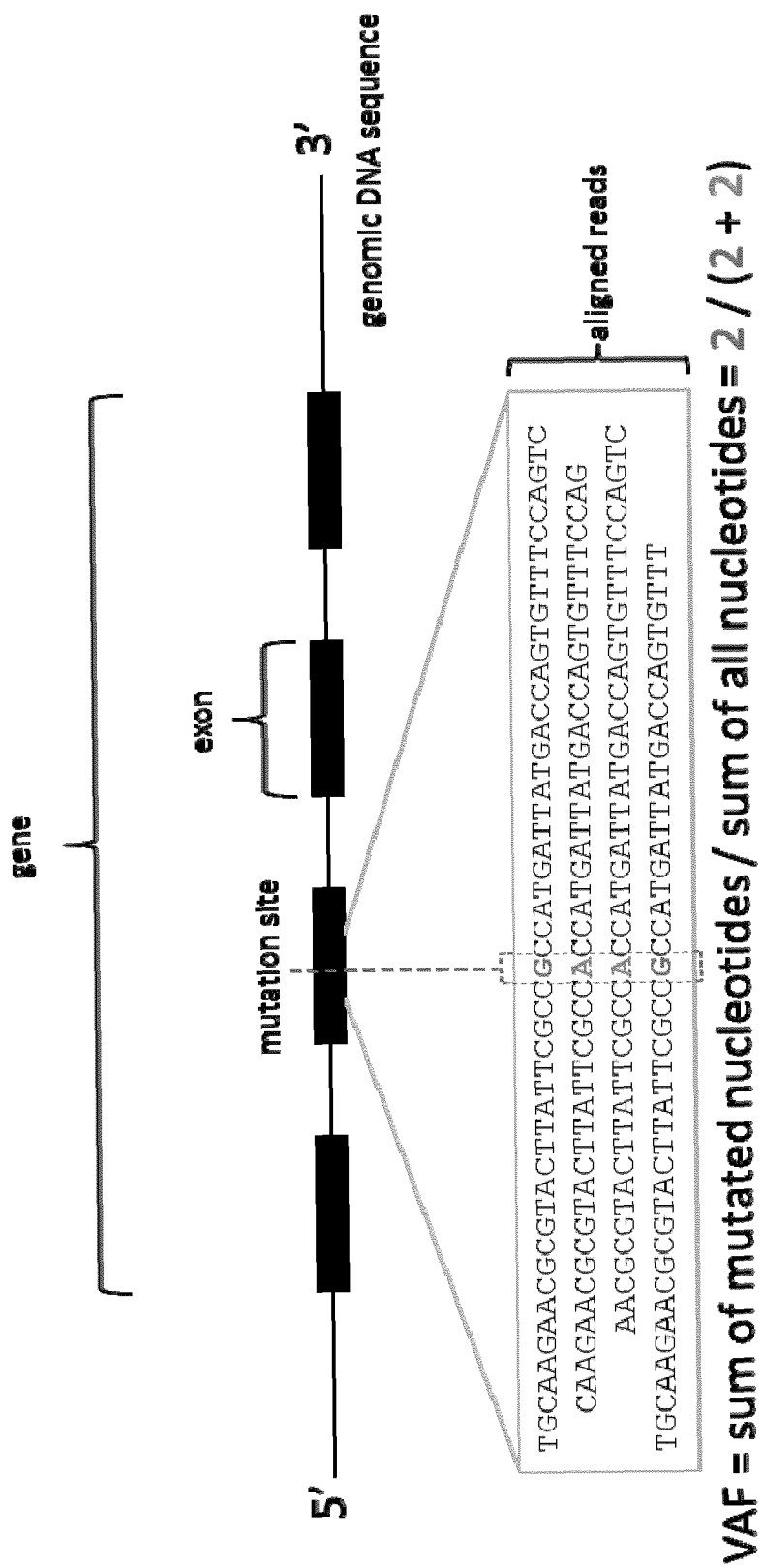

FIG. 5: Calculation of variant allele frequency (VAF). The figure shows an idealized gene as a combination of exons on a piece of genomic DNA (upper part) and example read sequences aligned to this locus (lower part, in a higher zoom level). The site of the mutation event ("mutation site") is shown by a dashed line (upper part) or box (lower part). The mutant nucleotides are colored red, the wild type nucleotides are colored green. Also the sums of those nucleotides in the VAF formula are colored accordingly. Sequences in a: TGCAAGAACGCGT ACTTATTCGCCGCCATGAT-TATGACCAGTGTTTCCAGTC (SEQ ID NO: 101); CAAGAA CGCGTACTTATTCGCCACCATGAT-TATGACCAGTGTTTCCAG (SEQ ID NO: 102); AAC GCGTACTTATTCGCCACCATGAT-TATGACCAGTGTTTCCAGTC (SEQ ID NO: 103); TG CAAGAACGCGTACTTATTCGCCGCCATGAT-TATGACCAGTGTTT (SEQ ID NO: 104).

Figure 6:
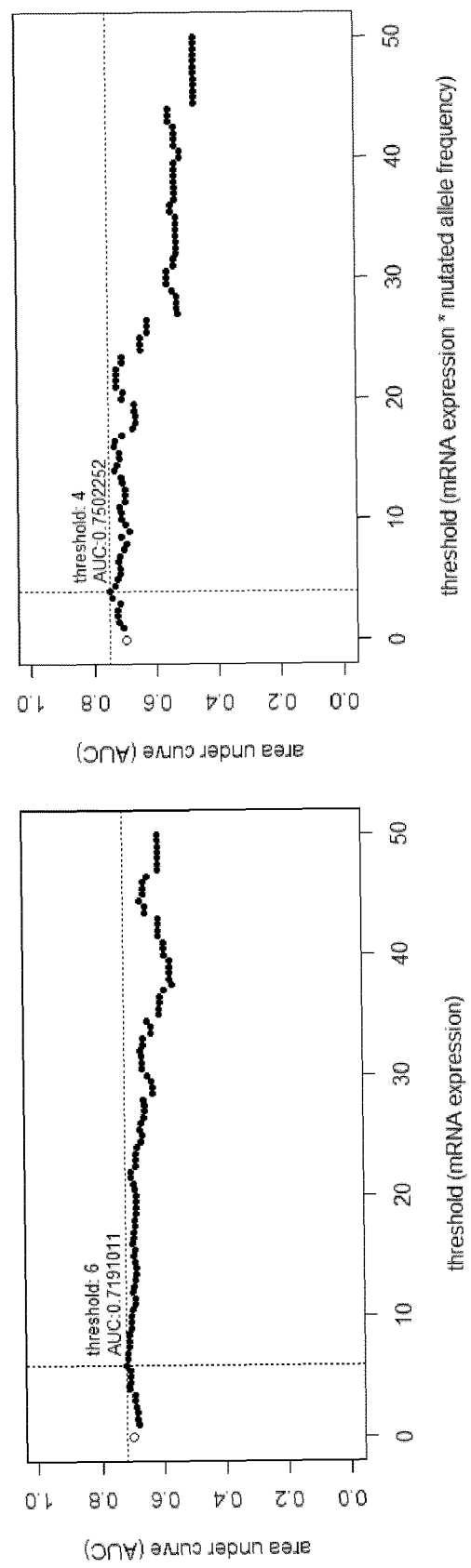

FIG. 6: Influence of the expression of mutated allele on the prediction performance of MHC II-scores. 185 selected mutations from the murine tumor models 4T1, CT26 and B16F10 were tested for their antigenicity. The predictive performance of the calculated MHC II-scores was deduced from the area under the receiver operating characteristic curve (AUC, open circle). This value was subsequently recalculated after applying different thresholds for the total mRNA expression (left panel) and the expression of the mutated allele (right panel, mRNA expression*mutated allele frequency, closed circles). The maximum AUC values are indicated. The expression of the mutated allele contributes more to the improvement of the prediction performance.

Figure 7:
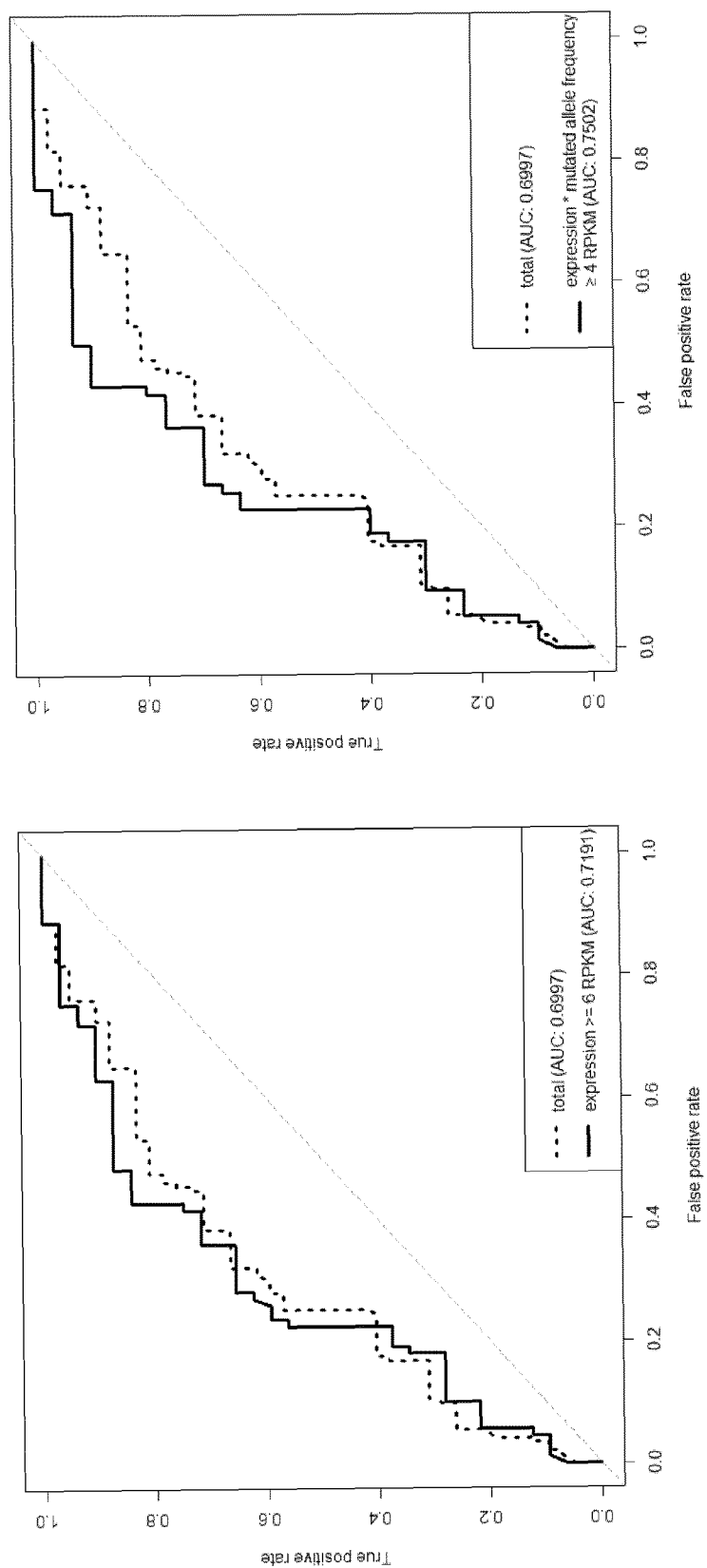

FIG. 7: Comparison of receiver operating characteristic (ROC) curves with and without threshold on the expression. The ROC curves indicate the performance of the antigenicity prediction for all 185 selected mutations from the murine tumor models 4T1, CT26 and B16F10 (dotted curves) and for those mutations, for which the mRNA expression was ≥6 RPKM (left panel, solid curve) or the expression of the mutated allele was ≥4 RPKM (right panel, solid curve). The selected thresholds achieved the maximum AUC values (see FIG. 6).

EXAMPLES

The techniques and methods used herein are described herein or carried out in a manner known per se and as described, for example, in Sambrook et al., Molecular Cloning: A Laboratory Manual. $2^{nd}$ Edition (1989) Cold Spring Harbor Laboratory Press. Cold Spring Harbor, N.Y. All methods including the use of kits and reagents are carried out according to the manufacturers' information unless specifically indicated.

Example 1: Materials and Methods

Samples. Female 8-12 week old C57BL/6, BALB/c mice (Janvier Labs) and C57BL/6BrdCrHsd-Tyr$^c$ mice (B6 albino, Harlan) were kept in accordance with federal policies on animal research at the University of Mainz. B16F10 melanoma cell line, CT26 colon carcinoma cell line and 4T1-luc2-tdtomato (4T1-Luc) cells were purchased in 2010, 2011 and 2011 respectively (ATCC CRL-6475 lot #58078645. ATCC CRL-2638 lot #58494154, Caliper 125669 lot #101648) and maintained as suggested by the supplier. Firefly luciferase expressing CT26-Luc and B16F10-Luc cells were lentivirally transduced. Master and working cell banks were generated, of which third and fourth passages were used for tumor experiments.

Next generation sequencing and data processing was described previously (Castle. J. C., et al., Cancer Res 72, 1081 (2012); Castle, J. C, et al., BMC Genomics 15, 190 (2014)). In brief, exome capture from mouse tumor cells and tail tissue samples of BALB/c or C57BL/6 mice were sequenced in triplicate (4T1-Luc in duplicate). Oligo(dT) based RNA sequencing libraries for gene expression profiling were prepared in triplicate. Libraries were sequenced on an Illumina HiSeq2000 to generate 50 nucleotide single-end (B16F10) or 100 nucleotide paired-end (CT26, 4T1-Luc) reads, respectively. Gene expression values were determined by counting reads overlapping transcript exons and junctions, and normalizing to RPKM expression units (Reads which map per kilobase of transcript length per million mapped reads). Mutation expression was determined by normalization of mutated RNA reads to the total mapped read counts multiplied by 100 million (normalized variant read counts; NVRC).

Mutation selection, validation and prioritization was described previously (Castle, J. C., el al., Cancer Res 72, 1081 (2012); Castle, J. C., et al., BMC Genomics 15, 190 (2014); Lower, M., et al., PLoS Comput Biol 8, e1002714 (2012)). Mutations to be pursued were selected based on following criteria: (i) present in the respective tumor cell line sequencing triplicates and absent in the corresponding healthy tissue sample triplicates, (ii) occur in a RefSeq transcript, and (iii) cause non-synonymous changes. Further criteria were occurrence in expressed genes of tumor cell lines (median RPKM across replicates). For validation, mutations were amplified from DNA of B16F10, CT26 or 4T1-Luc cells and C57BU6 or BALB/c tail tissue and subjected to Sanger sequencing. DNA-derived mutations were classified as validated if confirmed by either Sanger sequencing or the RNASeq reads. No confirmation via Sanger sequencing and immunogenicity testing was performed for experiments shown in FIG. 4. For experiments shown in FIG. 1 mutated epitopes were prioritized according to their predicted MHC class I binding based on the consensus method (version 2.5) of the Immune Epitope Database (Vita, R., et al., Nucleic Acids Res 38, D854-D862 (2010)). Mutations targeted in the experiment shown in FIG. 4b-e were selected based on either their expression (NVRC) alone or together with their predicted MHC class II peptide binding capability (IEDB consensus method version 2.5). Retrospective analysis of MHC II binding prediction shown in FIG. 4a was determined with IEDB consensus method version 2.12. For analysis of mutations in human tumors. DNA sequencing data of skin cutaneous melanoma (SKCM, n=308), colon adenocarcinoma (COAD, n=192) or breast invasive carcinoma (BRCA, n=872) retrieved from The Cancer Genome Atlas (TCGA) (august 2014) was filtered to obtain genomic non-synonymous point mutations (nsSNVs). RNASeq data (TCGA) of tumor samples with identified genomic mutations was used to define expressed nsSNVs. In order to predict MHC II binding expressed neo-epitopes seq2HLA was employed to identify the patients' 4-digit HLA class II (HLA-DQA1, HLA-DQB1, HLA-DRB1) type. The IEDB consensus binding prediction (version 2.12) was used to predict MHC class II binding from a 27mer peptide and the patients HLA-DRB1 alleles. As recommended from IEDB, neo-eptiopes with a percentile rank below 10% were considered as binders.

Synthetic RNA and synthetic peptides. Identified non-synonymous mutations were studied in the context of the respective 27mer amino acid epitope with the mutated amino acid in the center (position 14). Either of these mutated peptides were synthesized together with control peptides (vesiculo-stomatitis virus nucleo-protein (VSV-$NP_{52-59}$), gp70-AH1 (gp70$_{432-431}$) and tyrosinase-related protein 2 (Trp2$_{180-188}$) by JPT Peptide Technologies GmbH. Alternatively, sequences encoding mutated 27mer peptides were cloned into the pST1-Sp-MITD-2hBgUTR-A120 backbone (Holtkamp, S., et al., Blood 108, 4009 (2006)) featuring sequence elements for pharmacologically optimized synthetic RNA in terms of translation efficiency and MHC class I/II processing of epitopes either as monotones or as pentatopes fused to each other by sequences encoding 10 amino acid long glycine-serine linker in between. Linearization of these plasmid constructs, in vitro translation (IVT) of these templates and purification are described in detail elsewhere (Holtkamp, S., et al., Blood 108, 4009 (2006)).

Mouse Models.

For experiments investigating the immunogenicity of mutated epitopes age-matched female C57BL/6 or BALB/c mice were vaccinated on day 0, 3, 7 and 14 (immunization with RNA) or day 0 and 7 (immunization with peptide), the read out was performed five to six days after the last immunization. Vaccination was performed cither by retro-orbital injection of 200 µl (20 µg per mutation for B16F10, 40 µg per mutation for CT26) RNA complexed with anionic lipids (manuscript in preparation) or subcutaneous injection of 100 µg synthetic peptide and 50 µg poly (I:C) formulated in PBS (200 µL total volume) into the lateral flank. Two mutations per mouse were tested (n=5 for B16F10, n=3 for CT26). For confirmation of immunogenic mutations and subtyping, mice were vaccinated against a single mutation (n=5).

For therapeutic tumor experiments C57BL/6 mice were inoculated subcutaneously with $1\times10^5$ B16F10 melanoma cells into the right flank and randomly distributed into treatment groups. Tumor volume was measured unblinded with a caliper and calculated using the formula $(A\times B^2)/2$ (A as the largest and B the smallest diameter of the tumor). In lung metastasis experiments $5\times10^5$ CT26-Luc or $2\times10^5$ CT26 cells were injected into the tail vein of BALB/c mice or $1.5\times10^5$ B16F10-Luc tumor cells into B6 albino mice to obtain lung tumors. Tumor growth of luciferase transgenic cells was traced unblinded by bioluminescence imaging after i.p. injection of an aqueous solution of D-luciferin (250 µl, 1.6 mg, BD Bioscience) on an IVIS Lumina (Caliper Life Sciences). Five minutes after injection emitted photons were quantified. In vivo bioluminescence in regions of interest (ROI) were quantified as total flux (photons/sec) using IVIS Living Image 4.0 software. Mice were randomized based on their total flux values (ANOVA-P method, Daniel's XL Toolbox V6.53). CT26 lung tumor burden was quantified unblinded after tracheal Ink (1:10 diluted in PBS) injection and fixation with Fekete's solution (5 mL 10% EtOH, 0.5 mL formalin, and 0.25 mL glacial acetic acid). In therapeutic experiments mice were administered repealed doses of either monotone (40 µg), pentatope RNA (in total 40 µg) or equimolar amounts of irrelevant RNA.

For mechanistic studies repealed doses of CD8 depleting (clone YTS191, BioXcell), CD4 depleting (clone YTS169.1, BioXcell) or CD40L blocking (clone MR1, kind gill of Prof. Stephen Schoenberger) antibodies were administered intraperitoneally as indicated in the figure (200 µg/mouse in 200 µL PBS).

Enzyme-linked immunospot (ELISpot) has been previously described (Kreiter. S., et al., Cancer Res 70, 9031 (2010)). In brief, $5\times10^5$ splenocytes were cultured over night at 37° C. in anti-INF-γ (10 µg/mL, clone AN18, Mabtech) coated Multiscreen 96-well plates (Millipore) and cytokine secretion was detected with an anti-IFN-γ antibody (1 µg/mL, clone R4-6A2, Mabtech). For stimulation either 2 µg/mL peptide was added or spleen cells were coincubated with $5\times10^4$ syngeneic bone marrow-derived dendritic cells (BMDC) transfected with RNA. For analysis of tumor infiltrating lymphocytes, single cell suspensions of lung metastasis were rested overnight to get rid of living tumor cells via plastic adherence. Viable cells were separated via density gradient centrifugation. All retrieved cells were added to the ELISpot plate. For analysis of T cell responses in peripheral blood, PBMC were isolated via density gradient centrifugation, counted and resimulated by addition of peptide and syngeneic BMDC. Subtyping of T cell responses was performed by addition of a MHC class II blocking antibody (20 µg/mL clone M5/114, BioXcell). All samples were tested in duplicates or triplicates.

Flow cytometric analysis was used to determine the subtype of mutation reactive T cells. In the presence of Brefeldin A (Sigma-Aldrich) $2\times10^6$ splenocytes were stimulated with $2\times10^5$ RNA transfected BMDC or 2 µg/mL peptide. As a positive control splenocytes were treated with phorbol 12-myristate 13-acetate (PMA, 0.5 µg/ml, Sigma-Aldrich) and Ionomycin (1 µg/ml, Sigma-Aldrich). Cells were incubated 5 h at 37° C. and subsequently stained for CD4$^+$ and CD8$^+$ cell surface marker. Cells were permeabilized and fixated using BD Cytofix/Cytoperm according to the manufacturer's protocol and thereafter stained for INF-γ, TNF-α and IL-2 cytokines (BD Biosciences). Cytokine secretion among CD4+ or CD8+ T cells in stimulated samples was compared to control samples (medium, irrelevant RNA or irrelevant peptide) in order to determine the responding T cell subtype (n=5). Tumor infiltrating leucocytes were prepared from subcutaneous B16F10 tumors as described previously (PMID: 2071934). The resulting cell suspension was stained for CD4, CD8, Gr-1 and CD11b surface marker. Intracellular FoxP3 staining was performed according to the manufacturer's protocol (Mouse Foxp3 Buffer Set, BD). Samples were acquired on a BD FACSCanto II.

Immune histochemistry. Lungs of CT26 tumor bearing mice were fixated overnight in 4% phosphate buffered formaldehyde solution (Carl Roth) and embedded in paraffin. 50 µm consecutive sections (3 per mouse) were stained for CD3 (clone SP7, Abeam), CD4 (clone 1, cat #50134-M08H, Sino Biological) and FoxP3 (polyclonal, cat #NB100-39002, Novus Biologicals) following detection by a HRP-conjugated antibody (Poly-HRP-anti-rabbit IgG, ImmunoLogic) and the corresponding peroxidase substrate (Vector Nova Red, Vector Laboratories) and counterstained with hematoxylin. CD3+, CD4+, FoxP3+ and tumor areas were captured on an Axio Scan.Z1 (Zeiss) and manually pre-defined tumor and lung regions were quantified via computerized image analysis software (Tissue Studio 3.6.1. Definiens).

Immunofluorescence staining. Cryoconserved organs were cut in 8 µm sections and attached on Superfrost slides. Sections were dried overnight at room temperature (RT) and fixed in 4% para-formaldehyde (PFA) for 10 min at RT in the dark. Sections were washed 3 times with PBS and blocked using PBS supplemented with 1% BSA, 5% mouse serum, 5% rat serum and 0.0275 Nonident for 1 h at RT in the dark. Fluorescent labeled antibodies (FoxP3, clone FJK-16s, eBioscience; CD8, clone 53-6.7, BD; CD4, clone RM4-5, BD) were diluted in staining buffer (PBS supplemented with 1% BSA, 5% mouse serum and 0.02% Nonident) and sections were stained overnight at 4° C. After washing twice with washing buffer (PBS supplemented with 1% BSA and 0.02% Nonident) and once with PBS, slides were stained for 3 min with Hoechst (Sigma), washed 3 times with PBS, once with distilled water and mounted using Mounting Medium Flouromount G (eBioscience). Immunofluorescence images were acquired using an epifluorescence microscope (Apo-Tome, Zeiss). Tumor, CD4, CD8 and FoxP3 stained areas were quantified within manually pre-defined tumor regions via computerized image analysis software (Tissue Studio 3.6.1., Definiens)

Statistics. Means were compared by using Student's t-test for two groups. For comparison of means in more than two groups one-way ANOVA with Tukey's test was applied. The area under the curve (AUC) for comparison of tumor growth dynamics was determined for single mice per group and was displayed as median. Statistical differences in medians between two groups were calculated with a nonparametric Mann-Whitney U test. Survival benefit was determined with the log-rank test. All analyses were two-tailed and carried out using GraphPad Prism 5.03. ns: $P>0.05$, *: $P \leq 0.05$, : $P \leq 0.01$, *: $P \leq 0.001$, Grubb's test was used for identification of outliers (alpha=0.05).

Example 2: MHC Class II Restricted T Cell Epitopes in Neo-Epitope Vaccines

A. Characterization or T Cell Subtypes Reactive Against Mutated Epitopes

Recently, we described a workflow for comprehensive mapping of non-synonymous mutations of the B16F10 tumor by NGS (FIG. 1a) (Castle. J. C, et al., Cancer Res 72, 1081 (2012)). Tumor-bearing C57BL/6 mice were immunized with synthetic 27mer peptides encoding the mutated epitope (mutation in position 14), resulting in T cell responses which conferred in vivo tumor control. In continuation of that work, we now characterized the T cell responses against the mutated epitopes starting with those with a high likelihood of MHC I binding. Mice were vaccinated with synthetic 27mer mutated epitope peptides (FIG. 1b upper right). Their splenocytes were tested in IFN-γELISpot to identify immunogenic mutations for further analysis of subtype and cytokine expression (FIG. 1a). About 30% of mutated epitopes were found to induce mutation reactive cytokine secreting T cells in mice (FIG. 1b). Surprisingly, responses against nearly all mutated epitopes (16/17, 95%) were of CD4+ T cell type (FIG. 1b, Table 1).

TABLE 1

Immunogenic B16F10 mutations. B16F10 mutations determined to be immunogenic upon peptide or RNA immunization as described in FIG. 1). (WT, wild type; AA#, number of mutated amino acid; Mut, Mutation)

| Mutation | Gene | Mutated sequence used for vaccination | Substitution (WT, AA#, Mut) | Reactive T cell subtype | MHC I score (best prediction) | Response after vaccination with peptide | Response after vaccination with RNA |
|---|---|---|---|---|---|---|---|
| B16-M05 | Eef2 | FVVKAYLPVNESFAFTADLRSNTGGQA (SEQ ID NO: 1) | G795A | CD4+ | 1.1 | x | |
| B16-M08 | Ddx23 | ANFESGKHKYRQTAMFTATMPPAVERL (SEQ ID NO: 2) | V602A | CD4+ | 1.3 | | x |
| B16-M12 | Gnas | TPPPEEAMPFEFNGPAQGDHSQPPLQV (SEQ ID NO: 3) | S111G | CD4+ | 1.2 | x | |
| B16-M17 | Tnpo3 | VVDRNPQFLDPVLAYLMKGLCEKPIAS (SEQ ID NO: 4) | G504A | CD4+ | 1.0 | x | |
| B16-M20 | Tubb3 | FRRKAFLHWYTGEAMDEMEFTEAESNM (SEQ ID NO: 5) | G402A | CD4+ | 1.9 | x | |
| B16-M21 | Atp11a | SSPDEVALVEGVQSLGFTYLRLKDNYM (SEQ ID NO: 6) | R552S | CD4+ | 0.1 | | x |
| B16-M22 | Asf1b | PKPDFSQLQRNILPSNPRVTRFHINWD (SEQ ID NO: 7) | A141P | CD4+ | 1.7 | x | |
| B16-M24 | Dag1 | TAVITPPTTTTKKARVSTPKPATPSTD (SEQ ID NO: 8) | P425A | CD4+ | 2.2 | x | |

TABLE 1-continued

Immunogenic B16F10 mutations. B16F10 mutations determined to be immunogenic upon peptide or RNA immunization as described in FIG. 1). (WT, wild type; AA#, number of mutated amino acid; Mut, Mutation)

| Mutation | Gene | Mutated sequence used for vaccination | Substitution (WT, AA#, Mut) | Reactive T cell subtype | MHC I score (best prediction) | Response after vaccination with peptide | Response after vaccination with RNA |
|---|---|---|---|---|---|---|---|
| B16-M25 | Plod1 | STANYNTSHLNNDVWQIFENPVDWKEK (SEQ ID NO: 9) | F530V | CD4+ | 0.1 | x | x |
| B16-M27 | Obsl1 | REGVELCPGNKYEMRRHGTTHSLVIHD (SEQ ID NO: 10) | T1764M | CD8+ | 2.3 | x | x |
| B16-M28 | Ppp1r7 | NIEGIDKLTQLKKPFLVNNKINKIENI (SEQ ID NO: 11) | L170P | CD4+ | 3.2 | x | x |
| B16-M29 | Mthfd1l | IPSGTTILNCFHDVLSGKLSGGSPGVP (SEQ ID NO: 12) | F294V | CD4+ | 1.7 | x | |
| B16-M30 | Kif18b | PSKPSFQEFVDWENVSPEINSTDQPFL (SEQ ID NO: 13) | K739N | CD4+ | 1.2 | x | x |
| B16-M33 | Pbk | DSGSPFPAAVILRDALHMARGLKYLHQ (SEQ ID NO: 14) | V145D | CD8+ | 0.1 | | x |
| B16-M36 | Tm9sf3 | CGTAFFINFIAIYHHASRAIPFGTMVA (SEQ ID NO: 15) | Y382H | CD4+ | 0.2 | x | |
| B16-M44 | Cpsf31 | EFKHIKAFDRTFANNPGPMVVFATPGM (SEQ ID NO: 16) | D314N | CD4+ | 0.5 | x | x |
| B16-M45 | Mkrn1 | ECRITSNFVIPSEYWVEEKEEKQKLIQ (SEQ ID NO: 17) | N346Y | CD4+ | 1.4 | x | |
| B16-M46 | Actn4 | NHSGLVTFQAFIDVMSRETTDTDTADQ (SEQ ID NO: 18) | F835V | CD4+ | 0.2 | x | x |
| B16-M47 | Rpl13a | GRGHLLGRLAAIVGKQVLLGRKVVVVR (SEQ ID NO: 19) | A24G | CD4+ | 0.5 | | x |
| B16-M48 | Def8 | SHCHWNDLAVIPAGVVHNWDFEPRKVS (SEQ ID NO: 20) | R255G | CD4+ | 3.8 | x | x |
| B16-M50 | Sema3b | GFSQPLRRLVLHVVSAAQAERLARAEE (SEQ ID NO: 21) | L663V | CD4+ | 2.9 | x | x |

To exclude any bias associated with a peptide-based vaccine format, this experiment was repeated using in vitro transcribed (IVT) mRNA encoding the mutated epitopes (FIG. 1c upper graph right hand side). T cell reactivities determined with these RNA monotopes were largely comparable to the data obtained with synthetic peptides (FIG. 1c, Table 1), with somewhat lower numbers of immunogenic epitopes (about 25%). Importantly, also in this setting the majority of mutation-specific immune responses (10/12, ~80%) were conferred by CD4+ T cells.

We extended our study to the chemically induced colon carcinoma model CT26 (Griswold, D. P. and Corbell, T. H., Cancer 36, 2441 (1975)) in BALB/c mice, in which we recently identified over 1680 non-synonymous mutations (Castle, J. C., et al., BMC Genomics 15, 190 (2014)). We selected 96 mutations based on their predicted MHC class I binding properties. In analogy to the B16F10 study, half of the candidates were good binders ('low score' 0.1-2.1). The other half was deliberately chosen for poor MHC I binding ('high score'>3.9). In total, about 20% of mutated epitopes were immunogenic in mice immunized with the respective RNA monotopes (FIG. 1d pie chart, Table 2). It is noteworthy that in the 'low' MHC I score subgroup a couple of CD8+ T cells inducing epitopes were identified, which was not the case in the "high" score subgroup (FIG. 1d right). This apparently did not bias against MHC class II restricted epitopes, as these were represented in similar frequency in both subgroups constituting the majority of CT26 immunogenic mutations (16/21, 80%).

TABLE 2

Immunogenic CT26 mutations. CT26 mutations determined to be immunogenic upon RNA immunization (as described in FIG. 1). (WT, wild type; AA#, number of mutated amino acid; Mut, Mutation)

| Mutation | Gene | Mutated sequence used for vaccination | Substitution (WT, AA#, Mut) | Reactive T cell subtype | MHC I score (best prediction) |
|---|---|---|---|---|---|
| CT26-M03 | Slc20a1 | DKPLRRNNSYTSYIMAICGMPLDSFRA (SEQ ID NO: 22) | T425I | CD4+ | 0.3 |
| CT26-M12 | Gpc1 | YRGANLHLEETLAGFWARLLERLFKQL (SEQ ID NO: 23) | E165G | CD8+ | 1.9 |
| CT26-M13 | Nphp3 | AGTCCEYWASRALDEEHSIGSMIQLPQ (SEQ ID NO: 24) | G234D | CD4+ | 0.1 |
| CT26-M19 | Tmem87a | QAIVRGCSMPGPWRSGRLLVSRRWSVE (SEQ ID NO: 25) | G63R | CD8+ | 0.7 |

TABLE 2-continued

Immunogenic CT26 mutations. CT26 mutations determined to be immunogenic upon RNA immunization (as described in FIG. 1). (WT, wild type; AA#, number of mutated amino acid; Mut, Mutation)

| Mutation | Gene | Mutated sequence used for vaccination | Substitution (WT, AA#, Mut) | Reactive T cell subtype | MHC I score (best prediction) |
|---|---|---|---|---|---|
| CT26-M20 | Slc4a3 | PLLPFYPPDEALEIGLELNSSALPPTE (SEQ ID NO: 26) | T373I | CD4+ | 0.0 |
| CT26-M24 | Cxcr7 | MKAFIFKYSAKTGFTKLIDASRVSETE (SEQ ID NO: 27) | L340F | CD4+ | 1.6 |
| CT26-M26 | E2f8 | VILPQAPSGPSYATYLQPAQAQMLTPP (SEQ ID NO: 28) | I522T | CD8+ | 0.1 |
| CT26-M27 | Agxt2l2 | EHIHRAGGLFVADAIQVGFGRIGKHFW (SEQ ID NO: 29) | E247A | CD4+ | 0.2 |
| CT26-M35 | Napl14 | HTPSSYIETLPKAIKRKINALKQLQVR (SEQ ID NO: 30) | V63I | CD4+ | 0.7 |
| CT26-M37 | Dhx35 | EVIQTSKYYMRDVIAIESAWLLELAPH (SEQ ID NO: 31) | T646I | CD4+ | 0.1 |
| CT26-M39 | Als2 | GYISRVTAGKDSYIALVDKNIMGYIAS (SEQ ID NO: 32) | L675I | CD8+ | 0.2 |
| CT26-M42 | Deptor | SHDSRKSTSFMSVNPSKEIKIVSAVRR (SEQ ID NO: 33) | S253N | CD4+ | 0.3 |
| CT26-M43 | Tdg | AAYKGHHYPGPGNYFWKCLFMSGLSEY (SEQ ID NO: 34) | H169Y | CD4+ | 0.3 |
| CT26-M55 | Dkk2 | EGDPCLRSSDCIDEFCCARHFWTKICK (SEQ ID NO: 35) | G192E | CD4+ | 9.7 |
| CT26-M58 | Rpap2 | CGYPLCQKKLGVISKQFYRISTKTNKV (SEQ ID NO: 36) | P113S | CD4+ | 11.3 |
| CT26-M68 | Steap2 | VTSIPSVSNALNWKEFSFIQSTLGYVA (SEQ ID NO: 37) | R388K | CD4+ | 6.8 |
| CT26-M75 | Usp26 | KTTLSHTQDSSQSLQSSSDSSKSSRCS (SEQ ID NO: 38) | S715L | n.d. | 5.8 |
| CT26-M78 | Nbea | PAPRAVLTGHDHEIVCVSVCAELGLVI (SEQ ID NO: 39) | V576I | CD4+ | 6.3 |
| CT26-M90 | Aldh18a1 | LHSGQNHLKEMAISVLEARACAAAGQS (SEQ ID NO: 40) | P154S | CD4+ | 8.3 |
| CT26-M91 | Zc3h14 | NCKYDTKCTKADCLPTHMSRRASILTP (SEQ ID NO: 41) | P497L | CD4+ | 8.8 |
| CT26-M93 | Drosha | LRSSLVNNRTQAKIAEELGMQEYAITN (SEQ ID NO: 42) | V1189I | CD4+ | 9.9 |

On a similar note, when analyzing all immune responses to RNA monotones representing all 38 mutations we identified in the 4T1 mammary carcinoma model, nearly 70% of the recognized epitopes were recognized by CD4+ T cells (data not shown; Table 3).

TABLE 4

Immunogenic 4T1 mutations. 4T1 mutations determined to be immunogenic upon RNA immunization (as described in FIG. 1). (WT, wild type; AA#, number of mutated amino acid; Mut, Mutation)

| Mutation | Gene | Mutated sequence used for vaccination | Substitution (WT, AA#, Mut) | Reactive T cell subtype |
|---|---|---|---|---|
| 4T1-M2 | Gen1 | IPHNPRVAVKTTNNLVMKNSVCLERDS (SEQ ID NO: 43) | K707N | CD4 |
| 4T1-M3 | Polr2a | LAAQSLGEPATQITLNTFHYAGVSAKN (SEQ ID NO: 44) | M1102I | CD4 |
| 4T1-M8 | Tmtc2 | QGVTVLAVSAVYDIFVFHRLKMKQILP (SEQ ID NO: 45) | V201I | CD8 |
| 4T1-M14 | Zfr | AHIRGAKHQKVVTLHTKLGKPIPSTEP (SEQ ID NO: 46) | K411T | CD4 |
| 4T1-M16 | Cep120 | ELAWEIDRKVLHQNRLQRTPIKLQCFA (SEQ ID NO: 47) | H66N | CD4 |
| 4T1-M17 | Malt1 | FLKDRLLEDKKIAVLLDEVAEDMGKCH (SEQ ID NO: 48) | T534A | CD4 |
| 4T1-M20 | Wdr11 | NDEPDLDPVQELIYDLRSQCDAIRVTK (SEQ ID NO: 49) | T340I | CD8 |
| 4T1-M22 | Kbtbd2 | DAAALQMIIAYAYRGNLAVNDSTVEQL (SEQ ID NO: 50) | T914 | CD4 |
| 4T1-M25 | Adamts9 | KDYTAAGFSSFQKLPLDLTSMQIITTD (SEQ ID NO: 51) | I623L | CD4 |

TABLE 4-continued

Immunogenic 4T1 mutations. 4T1 mutations determined to be immunogenic upon RNA immunization (as described in FIG. 1). (WT, wild type; AA#, number of mutated amino acid; Mut, Mutation)

| Mutation | Gene | Mutated sequence used for vaccination | | Substitution (WT, AA#, Mut) | Reactive T cell subtype |
|---|---|---|---|---|---|
| 4T1-M26 | Pzp | AVKEEDSLHWQRPEDVQKVKALSFYQP | (SEQ ID NO: 52) | G1199E | CD8 |
| 4T1-M27 | Gprc5a | FAICFSCLLAHALNLIKLVRGRKPLSW | (SEQ ID NO: 53) | F119L | CD8 |
| 4T1-M30 | Enho | MGAAISQGAIIAIVCNGLVGFLL | (SEQ ID NO: 54) | L101 | CD4 |
| 4T1-M31 | Dmrta2 | EKYPKTPKCARCGNHGVVSALKGHKPY | (SEQ ID NO: 55) | R73G | CD4 |
| 4T1-M32 | Rragd | SHRSCSHQTSAPSPKALAHNGTPRNAI | (SEQ ID NO: 56) | L268P | CD4 |
| 4T1-M35 | Zzz3 | KELLQFKKLKKQNLQQMQAESGFVQHV | (SEQ ID NO: 57) | K311N | CD8 |
| 4T1-M39 | Ilkap | RKGEREEMQDAHVSLNDITQECNPPSS | (SEQ ID NO: 58) | 127S | CD4 |
| 4T1-M40 | Cenpf | RVEKLQLESELNESRTECITATSQMTA | (SEQ ID NO: 59) | D1327E | CD4 |

Thus, we have found in three independent mouse tumor models on different MHC backgrounds that a considerable fraction of non-synonymous cancer mutations are immunogenic and that quite unexpectedly the immunogenic mutanome is pre-dominantly recognized by CD4$^+$ T cells.

B. MHC Class II Restricted Cancer Mutations as Vaccine Targets

To investigate whether MHC class II restricted cancer mutations are good vaccine targets in vivo, we proceeded to use synthetic RNA as vaccine format. Antigen-encoding synthetic RNA is emerging as promising vaccine technology due to its advantages including its capability to deliver more than one epitope, its selective uptake by antigen presenting cells (APC) and its intrinsic adjuvanticity (Diken, M., et al., Gene Ther 18, 702 (2011); Kreiter. S., et al., Curr Opin Immunol 23, 399 (2011); Pascolo. S., Handb Exp Pharmacol, 221 (2008); Sahin. U., et al., Nat Rev Drug Discov 13, 759 (2014); Van, L. S., et al., Hum Vaccin Immunother 9 (2013)). Our group has developed pharmacologically optimized RNA (stabilizing elements in RNA sequence and liposomal formulation), which meanwhile has reached the stage of clinical testing (NCT01684241) (Holtkamp, S., et al., Blood 108, 4009 (2006); Kreiter. S., et al., J Immunol 180, 309 (2008); Kuhn. A. N., et al. Gene Ther 17, 961 (2010)). We engineered RNA encoding B16-M30, one of the epitopes identified in the B16F10 tumor model. B16-M30 elicited strong CD4$^+$ T cell responses, which did not recognize the wild type peptide (FIG. 2a left) as the mutated amino acid was shown to be essential for T cell recognition (FIG. 2a right). When B16F10 tumor-bearing C57B176 mice were repeatedly vaccinated with the B16-Mt30 RNA monotope, tumor growth was profoundly retarded (FIG. 2b). Half of the B16-M30 RNA treated mice were still alive 120 days after tumor vaccination, while all the control RNA treated mice died within 65 days.

Similarly, repeated vaccination in a lung metastasis model with luciferase transduced B16F10 cells revealed efficient eradication of metastases with B16-M30 RNA but not control synthetic RNA in the vast majority of mice as shown by bioluminescence imaging (BLI) (FIG. 2c). Consistently, tumor infiltrating leukocytes purified from B16F10 tumors of B16-M30 RNA immunized mice showed strong reactivity against B16-M30 (FIG. 2d).

Taking together, these data establish B16-M30 as a novel major rejection antigen in B16F10 tumors. They also exemplify that immunizing with RNA encoding a single immunogenic mutated epitope may give rise to functional T cells. These cells appear to be capable to target into the cancer lesion triggering control and even cure in murine tumor models. Our findings are in agreement with recent reports supporting the pivotal role of CD4$^+$ T cell immunity in the control of cancer (Schumacher, T., et al., Nature 512, 324 (2014); Tran, E., et al., Science 344, 641 (2014)).

As the vast majority of mutations are unique to the individual patient, tapping the mutanome as a source for vaccine antigens requires an actively individualized approach (Britten, C. M., et al., Nat Biotechnol 31, 880 (2013)). In this respect, one of the major challenges is instant manufacturing of a tailored on-demand vaccine. This can be viably addressed by RNA vaccine technology. RNA manufacturing based on in vitro transcription usually takes a few days (FIG. 3a). At present, the GMP-grade material could be made ready for release within three weeks and this process is continuously being optimized to reduce the duration. On another note, though we have shown tumor eradication in mouse models with a single mutation, one would ideally prefer to combine several mutations in a poly-neo-epitope vaccine. This would allow us to address several factors that counteract the clinical success of vaccines in humans such as tumor heterogeneity and immunoediting (Gerlinger, M., et al., N Engl J Med 366, 883 12012); Koebel, C. M., et al., Nature 450, 903 (2007)).

In light of these considerations, we explored how to use our insights on immunogenic epitopes to develop a cancer vaccine concept which we call "mutanome engineered RNA immunotherapy" (MERIT) (FIG. 3a). To test this concept, we selected four MHC class II (CT26-M03, CT26-M20, CT26-M27, CT26-M68) and one MHC class I (CT26-M19) restricted mutations that were derived from the CT26 model (sec Table 2) and engineered RNA monotopes encoding each of them. In addition, a synthetic RNA pentatope was engineered encoding all five mutated epitopes connected by 10mer non-immunogenic glycine/serine linkers to avoid the generation of junctional epitopes (FIG. 3a). By immunizing naïve BALB/c mice we found that the quantity of IFN-producing T cells elicited by the pentatope was comparable to that evoked by the respective monotone for three of these mutations (FIG. 3b). However, for two of these mutations the pentatope RNA was significantly superior in robustly expanding mutations-specific T cells.

We assessed the anti-tumour efficacy of immune responses elicited by RNA pentatope vaccines in a lung metastasis model of CT26 luciferase transfectant (CT26-Luc) tumors. Tumor-bearing BALB/c mice were vaccinated repeatedly with a mixture of two RNA pentatopes (3 MHC class I and 7 class II restricted epitopes) including the mutations tested in the previous experiment. Tumor growth in vaccinated mice was significantly inhibited as measured by BLI of the lung (FIG. 3c left). At day 32 all mice in the RNA pentatope group were alive whereas 80% of the control mice had already died (FIG. 3c mid). Post mortem macroscopic (FIG. 3c right), histological (FIG. 3d right) and computerized image analysis (data not shown) of tissue sections revealed significantly lower tumor load in the vaccinated mice as compared to untreated controls. Tumor lesions of pentatope RNA vaccinated mice were briskly infiltrated with CD3$^+$ T cells, whereas the number of CD3$^+$ T cells was significantly lower in their surrounding lung tissues. Tumors of untreated controls displayed CD3$^+$ cells staining which was not much different to that of the surrounding lung tissue in terms of quantity and mainly at the tumor border but not within the tumor. (FIG. 3d).

Altogether, these findings indicate that T cells against each single epitope are elicited with a MERIT approach employing a poly-neo-epitope encoding RNA vaccine. These T cells target tumor lesions, recognize their mutated targets and result in efficient tumor control in vivo.

C. Selection of Mutations Having Anti-Tumor Immunity

One of the key questions is how to select the mutations with the highest probability of inducing efficient anti-tumor immunity. We (FIG. 1d right) and others (Matsushita, H., et al., Nature 482, 400 (2012); Robbins. P. F., et al., Nat Med 19, 747 (2013); van, R. N., el al., J Clin Oncol 31, e439-e442 (2013)) have shown that MHC class I binding scores enable enrichment for mutated epitope candidates which elicit CD8$^+$ responses and tumor rejection (Duan, F., et al., J Exp Med 211, 2231 (2014)). Our findings described above indicate that MHC class II presented mutated epitopes may even be of higher interest for a MERIT approach. In fact, a correlation analysis revealed that immunogenic mutations have a significantly belter MHC class II binding score as compared to non-immunogenic ones (FIG. 4a). Most cancers lack MHC class II expression. Effective recognition of neo-epitopes by CD4$^+$ T cells in MHC class II negative tumors should depend on release of tumor antigens to be taken up and presented by antigen presenting cells (APCs). This should be most efficient for antigens with highly abundant expression. To test this hypothesis, we implemented an algorithm combining good MHC class II binding with abundant expression of the mRNA encoding the mutated epitope. For the latter we used confirmed mutated RNA sequencing reads normalized to the overall read count (NVRC: normalized variant read counts). We ranked CT26 mutanome data with this algorithm and selected the top ten mutations ('ME' mutations in Table 4) predicted to be good MHC class II binders among the most abundant candidate epitopes (NVRC≥60). As control we chose ten mutations based on abundant expression only ('E' mutations in Table 4). Most importantly, these epitopes were used without any further pre-validation or immunogenicity testing to engineer two RNA pentatopes for each group ($P_{ME}$ and $P_E$ pentatopes). When mice with established CT26-Luc lung tumors were vaccinated with these epitopes, $P_{ME}$ as compared to $P_E$ pentatopes induced a much stronger T cell response (FIG. 4c). Established lung metastases were completely rejected in almost all mice whereas $P_E$ pentatopes were not able to confer tumor growth control (FIG. 4b).

TABLE 4

In silico prediction of CT26 mutations with abundant expression and favorable MHC class II binding properties. CT26 mutations selected for high expression with (ME) or without (E) consideration of the MCH II percentile rank (IEDB consensus version 2.5). (WT, wild type; AA#, number of mutated amino acid; Mut, Mutation )

| Mutation | Gene | Mutated sequence used for vaccination | Substitution (WT, AA#, Mut) | Expression (NVRC) | MHC II score (best prediction) |
|---|---|---|---|---|---|
| CT26-E1 | Asns | DSVVIFSGEGSDEFTQGYIYFHKAPSP (SEQ ID NO: 60) | L370F | 1428.05 | 45.45 |
| CT26-E2 | Cd24 | PQTSPTGILPTTSNSISTSEMTWKSSL (SEQ ID NO: 61) | D120N | 1150.85 | 23.76 |
| CT26-E3 | Actb | WIGGSILASLSTFHQMWISKQEYDESG (SEQ ID NO: 62) | Q353H | 974.16 | 8.30 |
| CT26-E4 | Tmbim8 | SALGSLALMIWLMTTPHSHETEQKRLG (SEQ ID NO: 63) | A73T | 825.51 | 2.96 |
| CT26-E5 | Glud1 | DLRTAAYVNAIEKIFKVYNEAGVTFT (SEQ ID NO: 64) | V546I | 619.54 | 8.01 |
| CT26-E16 | Eif4g2 | KLCLELLNVGVESNLILKGVILLIVDK (SEQ ID NO: 65) | K108N | 327.79 | 20.99 |
| CT26-E17 | Sept7 | NVHYENYRSRKLATVTYNGVDNNKNKG (SEQ ID NO: 66) | A314T | 316.98 | 6.47 |
| CT26-E18 | Fn1 | YTVSVVALHDDMENQPLIGIQSTAIPA (SEQ ID NO: 67) | S1710N | 303.62 | 17.41 |
| CT26-E19 | Brd2 | KPSTLRELERYVLACLRKKPRKPYTIR (SEQ ID NO: 68) | S703A | 301.83 | 7.86 |
| CT26-E20 | Uchl3 | KFMERDPDELRFNTIALSAA (SEQ ID NO: 69) | A224T | 301.78 | 9.75 |
| CT26-M1 | Aldh18a1 | LHSGQNHLKEMAISVLEARACAAAGQS (SEQ ID NO: 70) | P154S | 67.73 | 0.05 |
| CT26-M2 | Ubqln1 | DTLSAMSNPRAMQVLLQTQQGLQTLAT (SEQ ID NO: 71) | A62V | 84.08 | 0.24 |
| CT26-M3 | Ppp6r1 | DGQLELLAQGALDNALSSMGALHALRP (SEQ ID NO: 72) | D309N | 139.80 | 0.44 |

TABLE 4-continued

In silico prediction of CT26 mutations with abundant expression and favorable MHC class II binding properties. CT26 mutations selected for high expression with (ME) or without (E) consideration of the MCH II percentile rank (IEDB consensus version 2.5). (WT, wild type; AA#, number of mutated amino acid; Mut, Mutation )

| Mutation | Gene | Mutated sequence used for vaccination | Substitution (WT, AA#, Mut) | Expression (NVRC) | MHC II score (best prediction) |
|---|---|---|---|---|---|
| CT26-M4 | Trip12 | WKGGPVKIDPLALMQAIERYLVVRGYG (SEQ ID NO: 73) | V1328M | 83.09 | 0.49 |
| CT26-M5 | Pcdhgc3 | QDINDNNPSFPTGKMKLEISEALAPGT (SEQ ID NO: 74) | E139K | 86.16 | 0.54 |
| CT26-M6 | Cad | SDPRAAYFRQAENFMYIRMALLATVLG (SEQ ID NO: 75) | G2139D | 152.86 | 0.55 |
| CT26-M7 | Smarcd1 | MDLLAFERKLDQTVMRKRLDIQEALKP (SEQ ID NO: 76) | I161V | 125.85 | 0.60 |
| CT26-M8 | Ddx27 | ITTCLAVGGLDVKFQEAALRAAPDILI (SEQ ID NO: 77) | S297F | 61.82 | 0.62 |
| CT26-M9 | Snx5 | KARLKSKDVKLAEAHQQECCQKFEQLS (SEQ ID NO: 78) | T341A | 120.27 | 0.73 |
| CT26-M10 | Lin7c | GEVPPQKLQALQRALQSEFCNAVREVY (SEQ ID NO: 79) | V41A | 71.24 | 1.09 |

Antigen specific $T_H$ cells promote the cross-priming of tumor specific CTL responses by CD40 ligand mediated licensing of dendritic cells. This may result in antigen spread if $T_H$ cells recognize their antigen on the same APC that cross-presents an unrelated CTL epitope (Bennett, S. R., et al., Nature 393, 478 (1998); Schoenherger. S. P., et al., Nature 393, 480 (1998)). Congruently, in the blood and spleen of mice immunized with $P_{ME}$ but not $P_E$ pentatopes we detected strong CD8$^+$ T cell responses against gp70-AH1, a well characterized immunodominant CTL epitope derived from the endogenous murine leukemia virus-related cell surface antigen (FIG. 4d). This indicates that cancer neo-epitope specific $T_H$ cells, in analogy to viral neo-antigen specific T cells (Croxford, J. L., et al., Autoimmun Rev 1, 251 (2002)), may exert their anti-tumour function by antigen spreading and augmentation of CTL responses D. Summary In summary, our data indicate that MHC class II restricted T cell epitopes are abundant in the cancer mutanome and can be used to customize RNA-based poly-neo-epitope vaccines with substantial therapeutic effect in mouse tumour models.

The mechanism responsible for the high rate of CD4$^+$ T cell recognition of mutations is unclear yet. A simple explanation may be the longer and variable size of peptides presented on MHC class II molecules as compared to MHC class I epitopes increasing the likelihood that a mutation is covered by the respective peptide. T cell epitopes presented by MHC class I molecules are typically peptides between 8 and 11 amino acids in length with well-defined N- and C-termini. MHC class II molecules present longer peptides of 13-17 amino acids in length with a 9 amino acid MHC II core binding region and variable number of additional flanking amino acids both contributing to the recognition by CD4$^+$ T cells (Arnold, P. Y., et al., J Immunol 169, 739 (2002)).

While the first evidence of the spontaneous CD8$^+$ and CD4$^+$ T-cell responses directed against mutated gene-products in cancer patients was generated in the 1990s (Dubey, P., et al., J Exp Med 185, 695 (1997); Lennerz, V., et al., Proc Natl Acad Sci USA 102, 16013 (2005); Wolfel, T., et al., Science 269, 1281 (1995)), only the recent high level publications have created broad acceptance for the enormous potential of mutation-specific T cells to confer anti-tumor activity in cancer patients (Lu, Y. C., et al., J Immunol 190, 6034 (2013); Schumacher, T., et al., Nature 512, 324 (2014); Tran, E., et al., Science 344, 641 (2014)). To assess whether the principles we unraveled in the mouse models for melanoma, colon and breast cancer are true in the human setting, we analyzed mutation and RNA-Seq data in the same three human cancer types provided by The Cancer Genome Atlas (TCGA). For all three human cancer types we confirmed the abundance of mutations predicted to bind to MHC class II we revealed in mouse models (FIG. 4.e).

The MERIT approach we presented here integrates advances in the field of next generation sequencing, computational immunology and synthetic genomics and thereby provides the integrated technology for comprehensive exploitation of the neo-epitope target repertoire. Targeting multiple mutations at once may at least in theory pave the way to solve critical problems in current cancer drug development such as clonal heterogeneity and antigen escape (Kroemer, G. and Zitvogel, L., Oncoimmunology 1, 579 (2012); Mittal, D., et al., Curr Opin Immunol 27, 16 (2014)).

Meanwhile, based on this study and our prior work clinical translation has been initiated and a first-in-concept trial in melanoma patients (Castle, J. C., el al., Cancer Res 72, 1081 (2012); Castle, J. C., et al., Sci Rep 4, 4743 (2014); Lower, M., et al., PLoS Comput Biol 8, e1002714 (2012)) is actively recruiting (NCT02035956) and confirms that "just in time" production of a poly-neo-epitope mRNA cancer vaccine is in fact feasible.

Example 3: Selection of Mutations Having Anti-Tumor Immunity

For selecting/ranking amino acid sequence modifications one may proceed as follows:

1. Within a given list of non-synonymous point mutations, compute a peptide sequence which has the mutated amino acid in the middle and is flanked by up to 13 amino acids on the N and C-terminal end, respectively; this will be called 27mer in the following text (the length for each flanking sequence may be smaller than 13 amino acids when the mutation is close to the N or C-terminus of the whole protein)

2. Compute MHC class II binding prediction consensus scores (e.g. using the IEDB T-cell prediction tools [Wang P. et al. (2010) BMC Bioinformatics. 11:568. PMID: 21092157. http://tools.immuneepitope.org/mhcii/]) for each overlapping 15 nt long subsequence of each 27mer; the best (=lowest) score is assigned to the whole 27mer
3. Compute the expression (preferably in RPKM units [Ali Mortazavi, et al. (2008) Nature Methods 5, 621-628]) of the genes to which the 27mers are associated
4. Compute the variant allele frequency (VAF) of each mutation in the RNA:
   input are short read alignments of an RNA-Seq experiment done with the same tumor sample as used for mutation detection
   look up the alignments and reads overlapping the mutation site
   tally the nucleotides mapped to the mutation site using the reads aggregated a step before
   compute the sum of mutant-allele nucleotides divided by the sum of all nucleotides mapped to the genomic site of the mutation (FIG. 5)
5. Multiply the respective gene expression with the VAF to get the mutation expression (preferably in RPKM units)
6. Rank all 27mers by the MHC binding score (as computed in step 2, lowest score is best) and remove 27mers with an associated mutation expression of less than a given threshold Application to Murine Data Set:

For testing the algorithm, 185 mutations were selected from the murine tumor models 4T1, CT26 and B16F10 were tested for their antigenicity. Then we first tried to test the influence of the level of gene and mutation expression on the predictive performance of the algorithm (FIG. 6). Here we can observe that the maximum area under the curve of the receiver operating characteristic (ROC AUC [Fawcett T., Pattern Recogn Lett. 2006; 27:861-874. doi: 10.1016/j.patree.2005.10.010]) is higher when the mutation expression is filtered instead of the gene expression (FIG. 6 left (gene expression) vs. right (mutation expression) plot). FIG. 7 shows the ROC curves for the optimum thresholds, indicating a pronounced influence of the mutation expression for binders with only a mediocre relative binding affinity (FIG. 7, right panel, values between a false positive rate of about 0.3 and 0.6).

The invention claimed is:

1. A method of treatment, the method comprising steps of:
   (i) identifying in a cancer patient one or more modified peptides comprising one or more amino acid modifications present in a modified protein relative to a parent protein, wherein said one or more modified peptides are each a fragment of the modified protein and include one or more amino acid modifications, each modified peptide characterized as immunogenic or more immunogenic by a computer-based analytical process comprising steps of:
      (a) determining its MHC class II binding ability, and assigning a binding score that indicates its likelihood of binding to one or more MHC class II molecules;
      (b) determining expression level of the protein to which each amino acid modification is associated and frequency of a variant allele encoding the one or more amino acid modifications or the respective modified peptide ("variant allele frequency"), and assigning an expression score for such expression and frequency; and
      (c) identifying the modified peptide as immunogenic or more immunogenic when the binding score satisfies a first pre-determined threshold indicating binding to the one or more MHC class II molecules, and the expression score satisfies a second pre-determined threshold indicating high abundance of the modified peptide; and
   (ii) producing a vaccine comprising a polypeptide, or a nucleic acid encoding the polypeptide, wherein the polypeptide comprises the identified one or more immunogenic or more immunogenic modified peptides; and
(iii) administering the vaccine, or having the vaccine be administered, to the cancer patient.

2. The method of claim 1, wherein the modified peptide is identified as immunogenic when (i) the binding score indicates a probability of MHC class II binding above a given threshold, and (ii) the expression score indicates abundance of the modified peptide above a given threshold.

3. The method of claim 1, wherein the steps (a) and (b) are performed on two or more different amino acid modifications.

4. The method of claim 3, wherein the different amino acid modifications are present in the same modified protein.

5. The method of claim 3, wherein the different amino acid modifications are present in different modified proteins.

6. The method of claim 3 further comprising a step of comparing the binding and/or expression scores of said two or more different amino acid modifications.

7. The method of claim 6, wherein the binding and/or expression scores of said two or more different modifications are compared by ranking the different amino acid modifications by their binding scores and removing, from a pool of characterized immunogenic amino acid modification candidates, an amino acid modification that has an expression or abundance less than a given threshold.

8. The method of claim 1, which comprises performing step a) on two or more different modified peptides comprising the same one or more amino acid modifications.

9. The method of claim 8, wherein the two or more different modified peptides comprising the same one or more amino acid modifications comprise different fragments of a modified protein, said different fragments comprising the same one or more amino acid modifications present in the modified protein.

10. The method of claim 8, wherein the two or more different modified peptides comprising the same one or more amino acid modifications comprise different potential MHC class II binding fragments of a modified protein, said fragments comprising the same one or more amino acid modifications present in the modified protein.

11. The method of claim 8, further comprising selecting as a characterized immunogenic peptide a modified peptide from the two or more different modified peptides comprising the same one or more amino acid modifications that has a binding score indicative of a probability or a highest probability for binding to one or more MHC class II molecules.

12. The method of claim 8, wherein the two or more different modified peptides comprising the same one or more amino acid modifications differ in (i) length, (ii) position, or (iii) both length and position of the one or more amino acid modifications.

13. The method of claim 1, wherein one or both of the expression level of the protein to which the modification is associated and the frequency of a variant allele encoding the one or more amino acid modifications or the respective modified peptide ("variant allele frequency") is determined on an RNA level.

14. The method of claim 1, wherein the variant allele frequency is determined by dividing number of detected sequences encoding the amino acid modification at a site by number of all detected sequences encoding the site.

15. The method of claim 1, wherein the step (b) comprises:
determining expression level of (i) the parent protein and (ii) the modified protein; and
multiplying the sum of the expression level of both the parent protein and the modified protein by the variant allele frequency.

16. The method of claim 1, wherein the one or more amino acid modifications comprise a non-synonymous mutation in a protein-coding region.

17. The method of claim 1, further comprising, prior to performing steps (a) and (b), sequencing a partial or whole genome or transcriptome of (i) a cancer cell or (ii) a cancer cell and a non-cancer cell; and identifying at least one mutation in one or more protein-coding regions within the sequenced genome or transcriptome of the cancer cell, wherein the at least one mutation encodes at least one of the one or more amino acid modifications in the modified protein.

18. The method of claim 17, wherein the at least one mutation is or comprises a somatic mutation.

19. The method of claim 17, wherein the at least one mutation is or comprises a cancer-specific mutation.

20. The method of claim 1, wherein a tumor specimen from the cancer patient has been analyzed for expression or abundance of one or more modified proteins comprising the one or more amino acid modifications.

21. The method of claim 1, wherein the cancer patient has been determined to express the one or more MHC class II molecules.

* * * * *